United States Patent
Islam et al.

(10) Patent No.: US 6,211,241 B1
(45) Date of Patent: Apr. 3, 2001

(54) ARYL SULFONAMIDES AND SULFAMIDE DERIVATIVES AND USES THEREOF

(75) Inventors: Imadul Islam, Hercules, CA (US); Daljit S. Dhanoa, West Chester, PA (US); John M. Finn, Andover, MA (US); Ping Du, Mahwah, NJ (US); Charles Gluchowski, Danville, CA (US); Yoon T. Jeon, Ridgewood, NJ (US)

(73) Assignee: Synaptic Pharmaceutical Corporation, Paramus, NJ (US)

( * ) Notice: Subject to any disclaimer, the term of this patent is extended or adjusted under 35 U.S.C. 154(b) by 0 days.

(21) Appl. No.: 09/088,450

(22) Filed: Jun. 1, 1998

Related U.S. Application Data

(63) Continuation of application No. PCT/US96/19085, filed on Nov. 27, 1996, which is a continuation of application No. 08/566,104, filed on Dec. 1, 1995, now abandoned.

(51) Int. Cl.[7] .......................... A61K 31/18; C07C 303/00
(52) U.S. Cl. .................. 514/602; 514/603; 514/604; 564/84; 564/85; 564/86; 564/87
(58) Field of Search ................. 564/84, 85, 86, 564/87; 514/602, 603, 604

(56) References Cited

U.S. PATENT DOCUMENTS

| | | | |
|---|---|---|---|
| 5,137,901 | * 8/1992 | Junge et al. | 514/373 |
| 5,352,705 | 10/1994 | Deanna et al. | 514/630 |
| 5,455,258 | 10/1995 | Macpherson et al. | 514/357 |
| 5,506,258 | 4/1996 | Christophe et al. | 514/423 |

FOREIGN PATENT DOCUMENTS

| | | |
|---|---|---|
| 9305014 | 3/1993 | (WO) . |
| 9415930 | 7/1994 | (WO) . |

OTHER PUBLICATIONS

Bhagwat, Shripad S., et al., "Thromboxane Receptor Antagonism Combined with Thromboxane Synthase Inhibition 4. 8-[[(4–Chlorophenyl) sulfonyl]amino]-4-(3-(3-pyridinyl)propyl) octanoic Acid and Analogs" *J. Med. Chem.* (1992) 35(23): 4373–4383; and.

Titmas, Richard C., et al., "Aspects of Antibody-Catalyzed Primary Amide Hydrolysis" *Applied Biochemistry and Biotechnology* (1994) 47:277–292.

* cited by examiner

*Primary Examiner*—Barbara Badio
(74) *Attorney, Agent, or Firm*—John P. White; Cooper & Dunham LLP

(57) ABSTRACT

This invention is directed to novel aryl sulfonamide and sulfamide compounds which bind selectively to and inhibit the activity of the human Y5 receptor. This invention is also related to uses of these compounds for the treatment of feeding disorders such as obesity, anorexia nervosa, bulimia nervosa, and abnormal conditions such as sexual/reproductive disorders, depression, epileptic seizure, hypertension, cerebral hemorrhage, congestive heart failure or sleep disturbances and for the treatment of any disease in which antagonism of a Y5 receptor may be useful.

11 Claims, No Drawings

ARYL SULFONAMIDES AND SULFAMIDE DERIVATIVES AND USES THEREOF

This application is a continuation of PCT International application No. PCT/US96/19085, filed Nov. 27, 1996, designating the United States of America and a continuation of U.S. Ser. No. 08/566,104, filed Dec. 1, 1995 now abandoned.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the sequence listing and the claims.

BACKGROUND OF THE INVENTION

The peptide neurotransmitter neuropeptide Y (NPY) is a 36 amino acid member of the pancreatic polypeptide family with widespread distribution throughout the mammalian nervous system (Dumont et al., 1992). The family includes the namesake pancreatic polypeptide (PP), synthesized primarily by endocrine cells in the pancreas; peptide YY (PYY), synthesized primarily by endocrine cells in the gut; and NPY, synthesized primarily in neurons (Michel, 1991; Dumont et al., 1992; Wahlestedt and Reis, 1993). All pancreatic polypeptide family members share a compact structure involving a "PP-fold" and a conserved C-terminal hexapeptide ending in $Tyr^{36}$ (or $Y^{36}$ in the single letter code). The striking conservation of $Y^{36}$ has prompted the reference to the pancreatic polypeptides' receptors as "Y-type" receptors (Wahlestedt et al., 1987), all of which are proposed to function as seven transmembrane-spanning G protein-coupled receptors (Dumont et al., 1992).

NPY and its relatives elicit a broad range of physiological effects through activation of at least five G protein-coupled receptor subtypes known as Y1, Y2, Y3, Y4 (or PP), and the "atypical Y1". While the Y1, Y2, Y3, and Y4 (or PP) receptors were each described previously in both radioligand binding and functional assays, the "atypical Y1" receptor is unique in that its classification is based solely on feeding behavior induced by various peptides including NPY.

The role of NPY in normal and abnormal eating behavior, and the ability to interfere with NPY-dependent pathways as a means to appetite and weight control, are areas of great interest in pharmacological and pharmaceutical research (Sahu and Kalra, 1993; Dryden et al., 1994). NPY is considered to be the most powerful stimulant of feeding behavior yet described (Clark et al., 1984; Levine and Morley, 1984; Stanley and Leibowitz, 1984). The stimulation of feeding behavior by NPY is thought to occur primarily through activation of the hypothalamic "atypical Y1" receptor. For example, direct injection of NPY into the hypothalamus of satiated rats can increase food intake up to 10-fold over a 4-hour period (Stanley et al., 1992). Similar studies using other peptides has resulted in a pharmacologic profile for the "atypical Y1" receptor according to the rank order of potencies of peptides in stimulating feeding behavior as follows: $NPY_{2-36} \geq NPY \sim PYY \sim [Leu^{31}, Pro^{34}]NPY > NPY_{13-36}$ (Kalra et al., 1991; Stanley et al., 1992). The profile is similar to that of a Y1-like receptor except for the anomalous ability of $NPY_{2-36}$ to stimulate food intake with potency equivalent or better than that of NPY. A subsequent report in *J. Med. Chem.* by Balasubramaniam and co-workers (1994) showed that feeding can be regulated by $[D-Trp^{32}]NPY$. While this peptide was presented as an NPY antagonist, the published data at least in part support a stimulatory effect of $[D-Trp^{32}]NPY$ on feeding. In contrast to other NPY receptor subtypes, the "feeding" receptor has never been characterized for peptide binding affinity in radioligand binding assays. The fact that a single receptor could be responsible for the feeding response has been impossible to validate in the absence of an isolated receptor protein; the possibility exists, for example, that the feeding response could be a composite profile of Y1 and Y2 subtypes.

This problem has been addressed by cloning rat and human cDNAs which encode a single receptor protein, referred to herein as Y5, whose pharmacologic profile links it to the "atypical Y1" receptor. The identification and characterization by applicants of a single molecular entity which explains the "atypical Y1" receptor allows the design of selective drugs which modulate feeding behavior. It is important to note, though, that any credible means of studying or modifying NPY-dependent feeding behavior must necessarily be highly selective, as NPY interacts with multiple receptor subtypes, as noted above (Dumont et al., 1992).

As used in this invention, the term "antagonist" refers to a compound which decreases the activity of a receptor. In the case of a G-protein coupled receptor, activation may be measured using any appropriate second messenger system which is coupled to the receptor in a cell or tissue in which the receptor is expressed. Some specific but by no means limiting examples of well-known second messenger systems are adenylate cyclase, intracellular calcium mobilization, ion channel activation, guanylate cyclase, and inositol phospholipid hydrolysis. Conversely, the term "agonist" refers to a compound which increases the activity of a receptor.

In order to test compounds for selective binding to the human Y5 receptor the cloned cDNAs encoding both the human and rat Y2 and Y4 (or PP) receptors have been used. The human and rat Y5 receptors were disclosed in PCT International Application No. PCT/US95/15646, published Jun. 6, 1996, and filed as a continuation in part of U.S. Ser. No. 08/349,025, filed Dec. 2, 1994, the contents of which are hereby incorporated by reference into this application. The human and rat Y2 receptors were disclosed in PCT International Application US95/01469, published Aug. 10, 1995, as WO 95/21245, and filed as a continuation-in-part of U.S. Ser. No. 08/192,288, filed Feb. 3, 1994, the contents of which are hereby incorporated by reference into this application. The human and rat Y4 receptors were disclosed in PCT International Application PCT/US94/14436, published Jul. 6, 1995, as WO 95/17906, and filed as a continuation-in-part of U.S. Ser. No. 08/176,412, filed Dec. 28, 1993, the contents of which are hereby incorporated by reference into this application. The Y1 receptor has been cloned from a variety of species including human, rat and mouse (Larhammar et al, 1992; Herzog et al, 1992; Eva et al, 1990; Eva et al, 1992).

The synthesis of novel aryl sulfonamide and sulfamide compounds are disclosed which bind selectively to the cloned human Y5 receptor compared to the other cloned human NPY receptors, and inhibit the activation of the cloned human Y5 receptor as measured in in vitro assays. The in vitro receptor binding and activation assays described hereinafter were performed using various cultured cell lines, each transfected with and expressing only a single Y-type receptor. In addition, the compounds of the present invention were shown to inhibit in animals either NPY-induced feeding behavior or feeding behavior exhibited by food-deprived animals.

This invention is also directed to the treatment of feeding disorders such as obesity and bulimia nervosa using the compounds described herein. In addition, the compounds of the present invention may also be used to treat abnormal conditions such as sexual/reproductive disorders, depression, epileptic seizure, hypertension, cerebral hemorrhage, congestive heart failure or sleep disturbances, or any condition in which antagonism of a Y5 receptor may be useful.

SUMMARY OF THE INVENTION

This invention is directed to novel aryl sulfonamide and sulfamide compounds which bind selectively to and inhibit the activity of the human Y5 receptor. This invention is also related to uses of these compounds for the treatment of feeding disorders such as obesity, anorexia nervosa, bulimia nervosa, and abnormal conditions such as sexual/reproductive disorders, depression, epileptic seizure, hypertension, cerebral hemorrhage, congestive heart failure or sleep disturbances and for the treatment of any disease in which antagonism of a Y5 receptor may be useful.

DETAILED DESCRIPTION OF THE INVENTION

The present invention is directed to compounds having the structures:

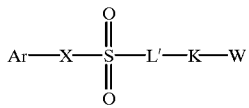

wherein Ar is

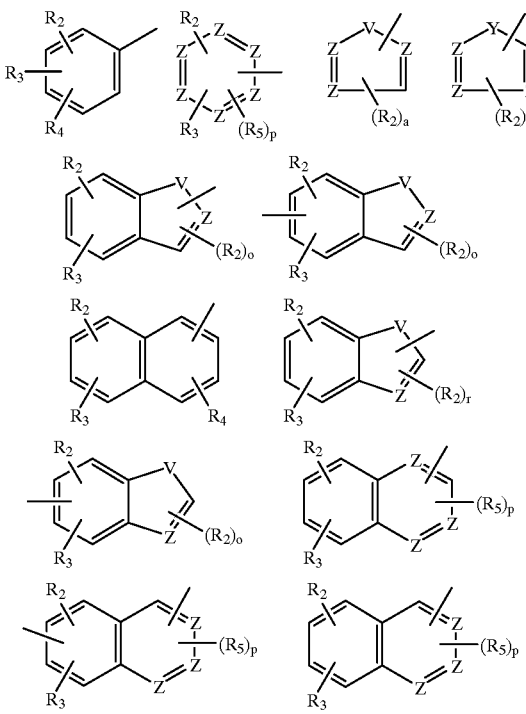

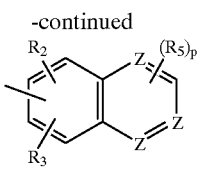

wherein each Z is independently N or C;

wherein each Y is independently N or C;

wherein p is an integer from 0 to 2;

wherein o is an integer from 0 to 1 and a is an integer from 0 to 3;

wherein V is S, O, N, or $NR_5$;

wherein X is a single bond or —NH—;

wherein each $R_2$ is independently H; F; Cl; Br; I; $NO_2$; OH; $C_1$–$C_4$ alkyl; $C_2$–$C_4$ alkenyl; $C_1$–$C_4$ alkoxy; $C_1$–$C_4$ hydroxyalkyl; $C_1$–$C_4$ methoxyalkyl; $C_1$–$C_4$ monohaloalkyl; $C_1$–$C_4$ polyhaloalkyl; $N(R_5)_2$; $NHCOR_5$; $N(COR_5)_2$; $NHCO_2R_5$; $NHCONHR_5$; $NHSO_2R_5$; $N(SO_2R_5)_2$; $CO_2R_5$; $CON(R_5)_2$; $SO_2N(R_5)_2$; phenoxy; phenyl; pyridyl; thiophenyl; naphthyl; phthalimide; $C_5$–$C_7$ lactam, $C_5$–$C_7$ cyclic imide, $C_5$–$C_7$ cyclic amino; wherein the phthalimide, lactam, cyclic imide, or cyclic amine is linked by nitrogen; and wherein the phenoxy, phenyl, pyridyl, thiophenyl, naphthyl, phthalimide, lactam, cyclic imide, or cyclic amine is substituted with H, F, Cl, Br, I, $CF_3$, $C_1$–$C_4$ alkyl, $C_1$–$C_4$ alkoxy, $C_1$–$C_4$ alkylthio, or $NO_2$;

wherein each $R_3$ is independently H; F; Cl; Br; I; $NO_2$; OH; $C_1$–$C_4$ alkyl; $C_2$–$C_4$ alkenyl; $C_1$–$C_4$ alkoxy; $C_1$–$C_4$ hydroxyalkyl; $C_1$–$C_4$ methoxyalkyl; $C_1$–$C_4$ monohaloalkyl; $C_1$–$C_4$ polyhaloalkyl; $N(R_5)_2$; $NHCOR_5$; $N(COR_5)_2$; $NHCO_2R_5$; $NHCONHR_5$; $NHSO_2R_5$; $N(SO_2R_5)_2$; $CO_2R_5$; $CON(R_5)_2$; $SO_2N(R_5)_2$; or $R_2$ and $R_3$ present on adjacent carbon atoms can constitute $C_5$–$C_7$ cycloalkyl, $C_5$–$C_7$ heterocycloalkyl or $C_5$–$C_7$ heteroaryl;

wherein each $R_4$ is independently H; F; Cl; Br; I; $NO_2$; OH; $C_1$–$C_4$ alkyl; $C_1$–$C_4$ alkoxy; $C_1$–$C_4$ hydroxyalkyl; $C_1$–$C_4$ methoxyalkyl; $C_1$–$C_4$ monohaloalkyl; $C_1$–$C_4$ polyhaloalkyl; $N(R_5)_2$; $NHCOR_5$; $N(COR_5)_2$; $NHCO_2R_5$; $NHCONHR_5$; $NHSO_2R_5$; $N(SO_2R_5)_2$; $CO_2R_5$; $CON(R_5)_2$; or $SO_2N(R_5)_2$; P1 wherein each $R_5$ is independently H; $C_1$–$C_3$ alkyl; $C_1$–$C_3$ monohaloalkyl; or $C_1$–$C_3$ polyhaloalkyl;

wherein L' is —$NR_1$—L— or

wherein L is $C_3$–$C_9$ alkyl; $C_3$–$C_9$ alkenyl; $C_3$–$C_9$ alkynyl;

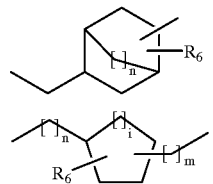

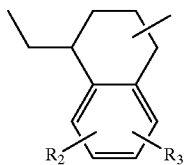

or

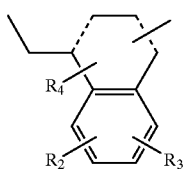

wherein $R_1$ is H; or $C_1$–$C_3$ straight chained alkyl;

wherein the alkyl, alkenyl or alkynyl is substituted with H, $OR_5$, CN, $C_1$–$C_6$ alkyl, $CH_2OR_5$, $CON(R_5)_2$, $CO_2R_5$, phenyl, pyridyl, thiophenyl or naphthyl;

wherein one dashed line is a double bond and the other dashed line is a single bond;

wherein each $R_6$ is independently H; CN; $OR_5$; $C_1$–$C_5$ alkyl; $CH_2OR_5$; $CON(R_5)_2$; $CO_2R_5$; phenyl; pyridyl; thiophenyl or naphthyl; wherein the phenyl, pyridyl, thiophenyl or naphthyl is substituted with H, F, Cl, Br, I, $CF_3$, $C_1$–$C_4$ alkyl, $C_1$–$C_4$ alkoxy, $C_1$–$C_4$ alkylthio, or $NO_2$;

wherein i is an integer from 1 to 4; wherein n is an integer from 0 to 3; wherein m is an integer from 0 to 3;

wherein K is $-CH_2-NR_{10}-CHR_7-(CH_2)_j-$; $-CH_2-NR_{10}-CO-(CH_2)_j-$; $-CH_2-NH-CO-NH-(CH_2)_j-$; $-CO-NH-CHR_7-(CH_2)_j-$; $-CH_2-NR_{10}-CO-CHR_7-(CH_2)_j$; $-CH_2-NR_{10}-CS-(CH_2)_j-$; $-CH_2-NH-CS-NH-(CH_2)_i-$; $-CS-NH-CHR_7-(CH_2)_j-$; $-CH_2-NR_{10}-CS-CHR_7-(CH_2)_j$; or $-CH_2-N=CSR_1-NH-(CH_2)_j$;

wherein j is an integer from 0 to 3;

wherein $R_7$ is H; $C_1$–$C_6$ alkyl; $CH_2OR_5$; $-(CH_2)_p NHCO_2R_5$; $(CH_2)_p NHSO_2R_5$; $CH_2N(R_{11})_2$; phenyl; pyridyl; thiophenyl; or naphthyl;

wherein W is

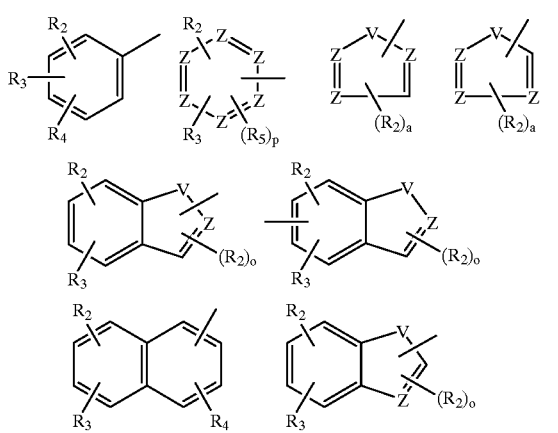

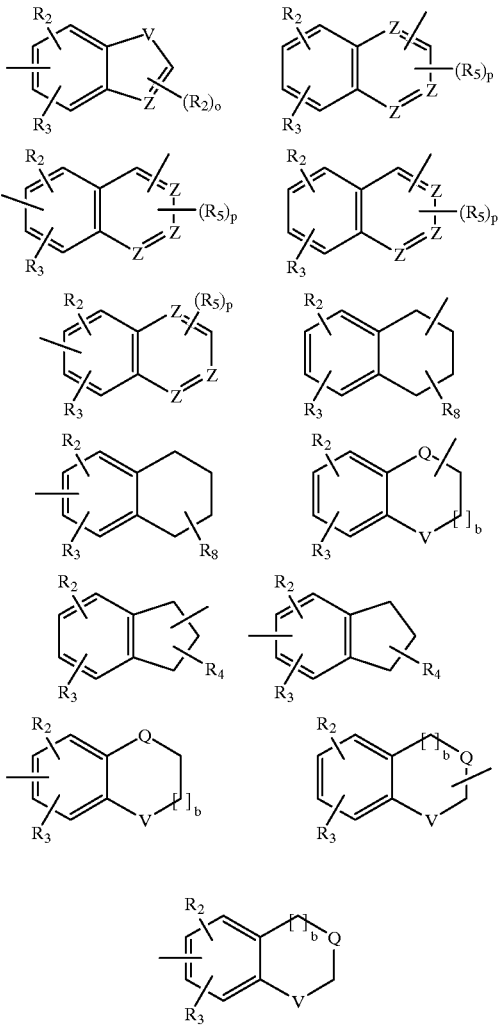

wherein Q is O; S; N; $NR_9$; or $C(R_5)_2$;

wherein b is an integer from 1 to 2;

wherein $R_8$ is independently H; F; Cl; Br; I; $NO_2$; OH; =O; $C_1$–$C_4$ alkyl; $C_1$–$C_4$ alkoxy; $C_1$–$C_4$ hydroxyalkyl; $C_1$–$C_4$ methoxyalkyl; $C_1$–$C_4$ monohaloalkyl; $C_1$–$C_4$ polyhaloalkyl; $N(R_5)_2$; $NHCOR_5$; $N(COR_5)_2$; $NHCO_2R_5$; $NHCONHR_5$; $NHSO_2R_5$; $N(SO_2R_5)_2$; $CO_2R_5$; $CON(R_5)_2$; or $SO_2N(R_5)_2$;

wherein $R_9$ is H; $C_1$–$C_3$ alkyl; $COR_5$; $CO_2R_5$; $CON(R_5)_2$;

wherein $R_{10}$ is H; or $C_1$–$C_6$ alkyl;

wherein $R_{11}$ is H; $COR_5$; $COR_{12}$; $SO_2R_5$; $SO_2R_{12}$; and wherein $R_{12}$ is phenoxy; phenyl, pyridyl; thiophenyl; or naphthyl; wherein the phenoxy, phenyl, pyridyl, thiophenyl or naphthyl is substituted with H, F, Cl, Br, I, $CF_3$, $C_1$–$C_4$ alkyl, $C_1$–$C_4$ alkoxy, $C_1$–$C_4$ alkylthio, $NO_2$, phenyl, pyridyl or thiophenyl; or a pharmaceutically acceptable salt thereof.

The invention also provides for the (+) and (−) enantiomers to the compounds described herein.

In one embodiment the invention provides for a compound as described above, where $R_1$ is H;

where L is selected from $C_3-C_9$ alkyl or

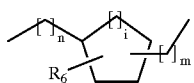

where the alkyl is substituted with H, $OR_5$, CN, $C_1-C_6$ alkyl, $CH_2OR_5$, $CON(R_5)_2$, $CO_2R_5$, phenyl, pyridyl, thiophenyl or naphthyl; and
where W is

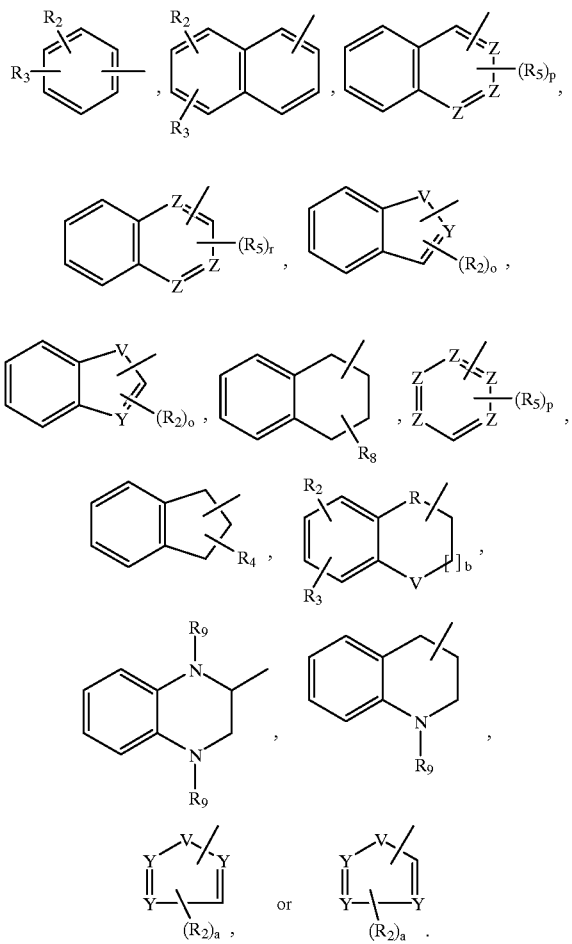

In other embodiments of the present invention, the compounds may have the structures where Ar is selected from:

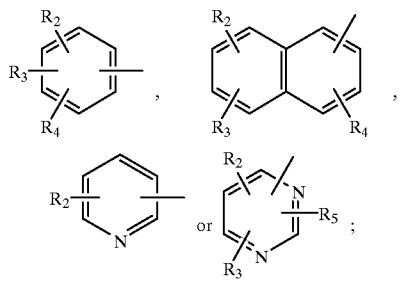

where each of $R_2$, $R_3$ and $R_4$ is independently H; F, Cl, Br or I; $NO_2$; OH; $C_1-C_4$ alkoxy; $C_1-C_4$ hydroxyalkyl; $C_1-C_4$ monohaloalkyl; $C_1-C_4$ polyhaloalkyl; or $N(R_5)_2$; where X is a single bond; where each $R_5$ is independently $C_1-C_3$ alkyl;

where L is selected from $C_5$-alkyl or $C_7$-alkyl; or

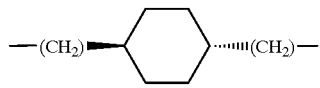

where $R_7$ is H; $CH_2OH$; or $CH_2OR_5$;
where W is

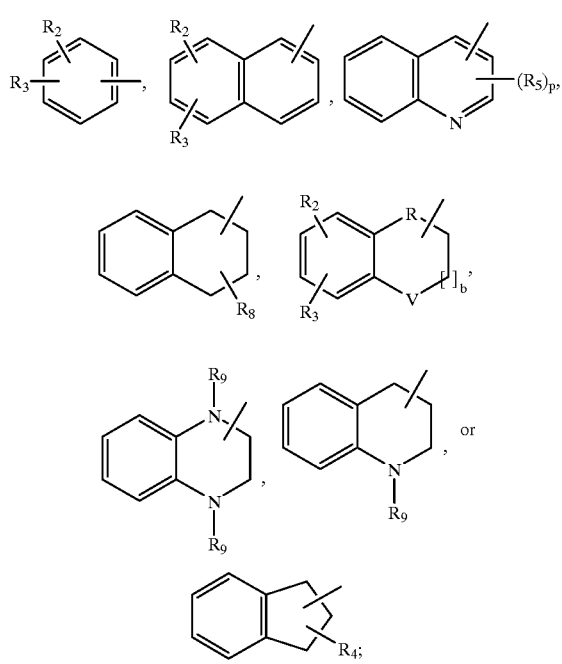

and where $R_9$ is H; or $C_1-C_3$ alkyl.

In other embodiments of the present invention Ar is selected from:

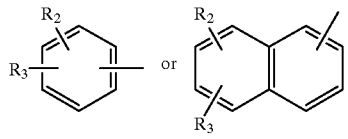

L is 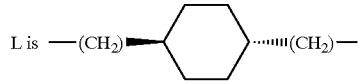

and K is $—CH_2—NR_{10}—CHR_7—(CH_2)_j—$.

Additional embodiments of the present invention include the compounds selected from the group consisting of:

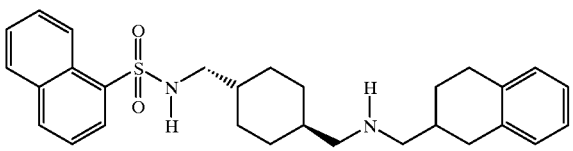

-continued

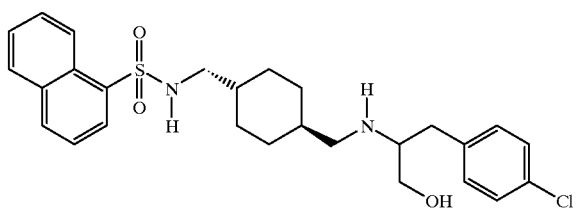

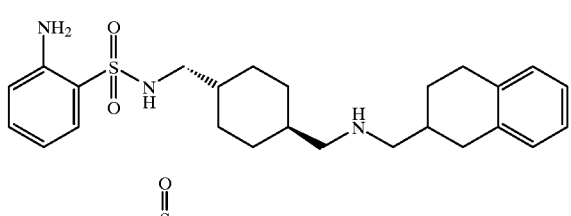

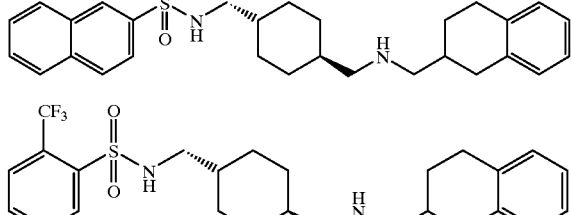

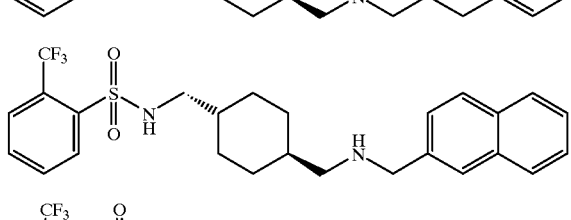

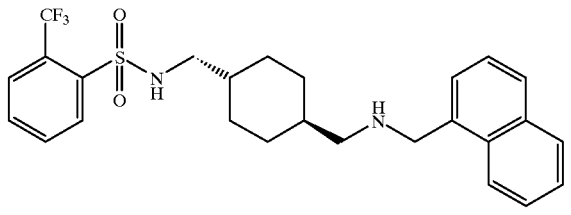

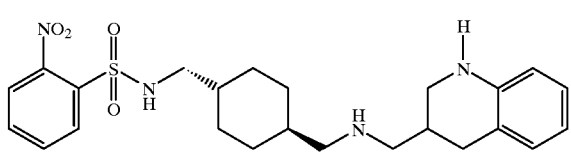

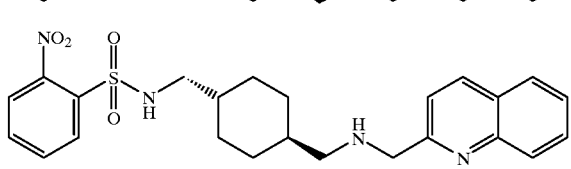

-continued

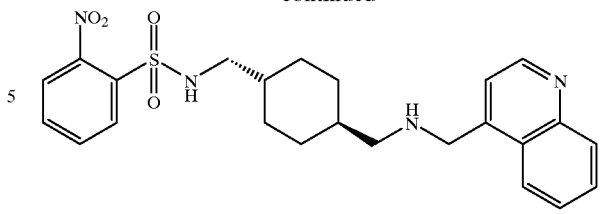

or

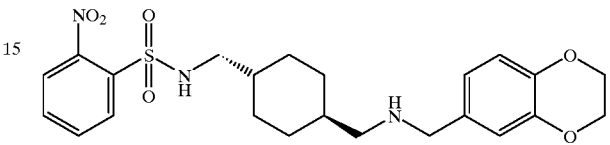

or

Additional embodiments of the present invention include those in which L is $C_5$-alkyl or $C_7$-alkyl.

In an embodiment of the invention the compounds have the structure:

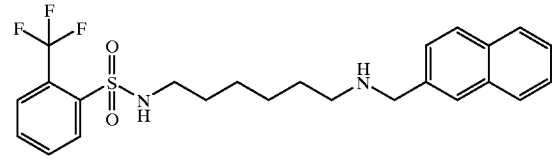

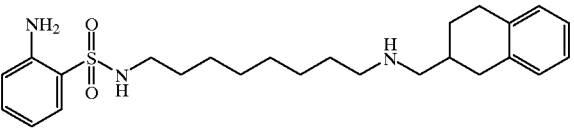

In one embodiment of the invention K is —$CH_2$—$NR_{10}$—CO—$(CH_2)_j$—.

In another embodiment of the invention the compound has the structure:

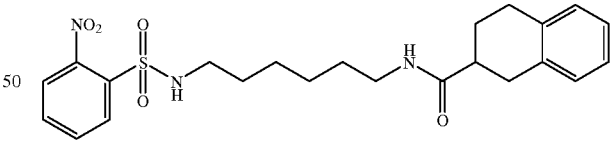

In yet another embodiment of the present invention K is —$CH_2$—NH—CO—NH—$(CH_2)_j$—.

In a further embodiment of the invention the compound has the structure:

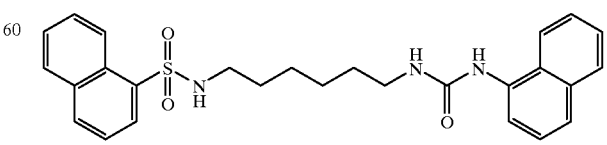

The invention also provides for a method of modifying feeding behavior of a subject which comprises administering to the subject an amount of a compound effective to decrease the consumption of food by the subject so as to thereby modify feeding behavior of the subject, where the compound has the structure:

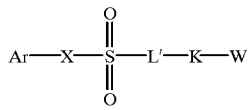

wherein Ar is

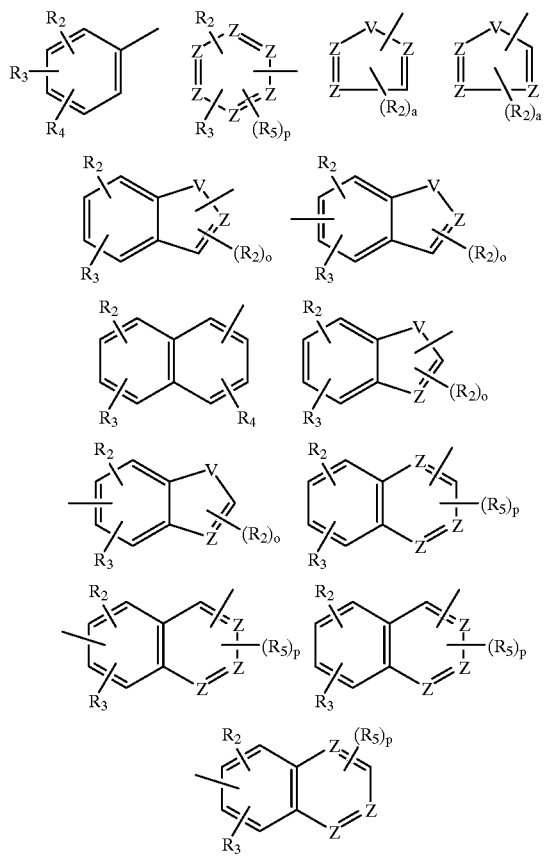

wherein each Z is independently N or C;
wherein each Y is independently N or C;
wherein p is an integer from 0 to 2;
wherein o is an integer from 0 to 1 and a is an integer from 0 to 3;
wherein V is S, O, N, or $NR_5$;
wherein X is a single bond or —NH—;
wherein each $R_2$ is independently H; F; Cl; Br; I; $NO_2$; OH; $C_1$–$C_4$ alkyl; $C_2$–$C_4$ alkenyl; $C_1$–$C_4$ alkoxy; $C_1$–$C_4$ hydroxyalkyl; $C_1$–$C_4$ methoxyalkyl; $C_1$–$C_4$ monohaloalkyl; $C_1$–$C_4$ polyhaloalkyl; $N(R_5)_2$; $NHCOR_5$; $N(COR_5)_2$; $NHCO_2R_5$; $NHCONHR_5$; $NHSO_2R_5$; $N(SO_2R_5)_2$; $CO_2R_5$; $CON(R_5)_2$; $SO_2N(R_5)_2$; phenoxy; phenyl; pyridyl; thiophenyl; naphthyl; phthalimide; $C_5$–$C_7$ lactam, $C_5$–$C_7$ cyclic imide, $C_5$–$C_7$ cyclic amino; wherein the phthalimide, lactam, cyclic imide, or cyclic amine is linked by nitrogen; and wherein the phenoxy, phenyl, pyridyl, thiophenyl, naphthyl, phthalimide, lactam, cyclic imide, or cyclic amine is substituted with H, F, Cl, Br, I, $CF_3$, $C_1$–$C_4$ alkyl, $C_1$–$C_4$ alkoxy, $C_1$–$C_4$ alkylthio, or $NO_2$;

wherein each $R_3$ is independently H; F; Cl; Br; I; $NO_2$; OH; $C_1$–$C_4$ alkyl; $C_2$–$C_4$ alkenyl; $C_1$–$C_4$ alkoxy; $C_1$–$C_4$ hydroxyalkyl; $C_1$–$C_4$ methoxyalkyl; $C_1$–$C_4$ monohaloalkyl; $C_1$–$C_4$ polyhaloalkyl; $N(R_5)_2$; $NHCOR_5$; $N(COR_5)_2$; $NHCO_2R_5$; $NHCONHR_5$; $NHSO_2R_5$; $N(SO_2R_5)_2$; $CO_2R_5$; $CON(R_5)_2$; $SO_2N(R_5)_2$; or $R_2$ and $R_3$ present on adjacent carbon atoms can constitute $C_5$–$C_7$ cycloalkyl, $C_5$–$C_7$ heterocycloalkyl or $C_5$–$C_7$ heteroaryl;

wherein each $R_4$ is independently H; F; Cl; Br; I; $NO_2$; OH; $C_1$–$C_4$ alkyl; $C_1$–$C_4$ alkoxy; $C_1$–$C_4$ hydroxyalkyl; $C_1$–$C_4$ methoxyalkyl; $C_1$–$C_4$ monohaloalkyl; $C_1$–$C_4$ polyhaloalkyl; $N(R_5)_2$; $NHCOR_5$; $N(COR_5)_2$; $NHCO_2R_5$; $NHCONHR_5$; $NHSO_2R_5$; $N(SO_2R_5)_2$; $CO_2R_5$; $CON(R_5)_2$; or $SO_2N(R_5)_2$;

wherein each $R_5$ is independently H; $C_1$–$C_3$ alkyl; $C_1$–$C_3$ monohaloalkyl; or $C_1$–$C_3$ polyhaloalkyl;

wherein L' is —$NR_1$—L— or

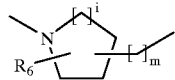

wherein L is $C_3$–$C_9$ alkyl; $C_3$–$C_9$ alkenyl; $C_3$–$C_9$ alkynyl;

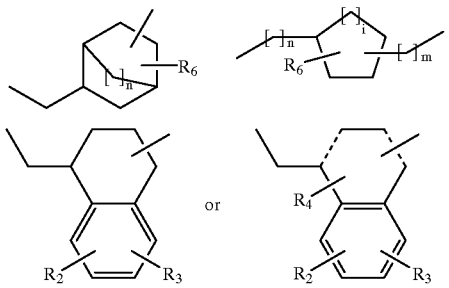

wherein $R_1$ is H; or $C_1$–$C_3$ straight chained alkyl;
wherein the alkyl, alkenyl or alkynyl is substituted with H, $OR_5$, CN, $C_1$–$C_6$ alkyl, $CH_2OR_5$, $CON(R_5)_2$, $CO_2R_5$, phenyl, pyridyl, thiophenyl or naphthyl;
wherein one dashed line is a double bond and the other dashed line is a single bond;
wherein each $R_6$ is independently H; CN; $OR_5$; $C_1$–$C_5$ alkyl; $CH_2OR_5$; $CON(R_5)_2$; $CO_2R_5$; phenyl; pyridyl; thiophenyl or naphthyl; wherein the phenyl, pyridyl, thiophenyl or naphthyl is substituted with H, F, Cl, Br, I, $CF_3$, $C_1$–$C_4$ alkyl, $C_1$–$C_4$ alkoxy, $C_1$–$C_4$ alkylthio, or $NO_2$;
wherein i is an integer from 1 to 4; wherein n is an integer from 0 to 3; wherein m is an integer from 0 to 3;
wherein K is —$CH_2$—$NR_{10}$—$CHR_7$—$(CH_2)_j$—; —$CH_2$—$NR_{10}$—CO—$(CH_2)_j$—; —$CH_2$—NH—CO—NH—$(CH_2)_j$—; —CO—NH—$CHR_7$—$(CH_2)_j$—; —$CH_2$—$NR_{10}$—CO—$CHR_7$—$(CH_2)_j$; —$CH_2$—$NR_{10}$—CS—$(CH_2)_j$—; —$CH_2$—NH—CS—NH—$(CH_2)_i$—; —CS—NH—$CHR_7$—$(CH_2)_j$—; —$CH_2$—$NR_{10}$—CS—$CHR_7$—$(CH_2)_j$; or —$CH_2$—N=$CSR_1$—NH—$(CH_2)_j$;
wherein j is an integer from 0 to 3;

wherein $R_7$ is H; $C_1$–$C_6$ alkyl; $CH_2OR_5$; $(CH_2)_p$NHCO$_2$R$_5$; $(CH_2)_p$NHSO$_2$R$_5$; $CH_2N(R_{11})_2$; phenyl; pyridyl; thiophenyl; or naphthyl;

wherein W is

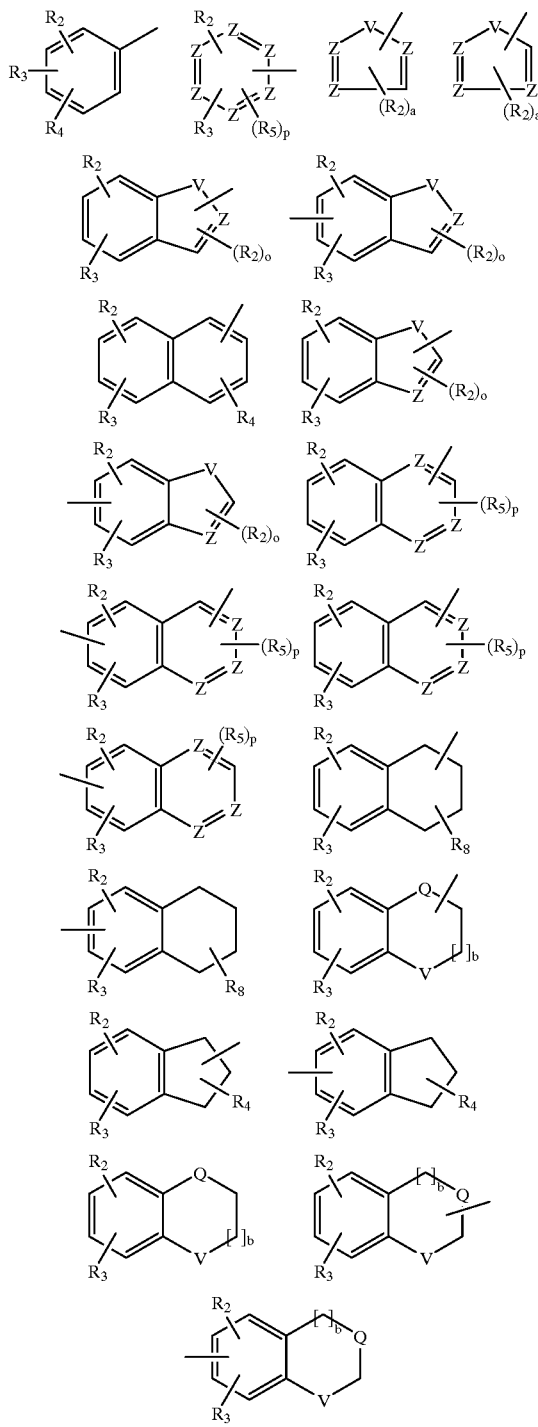

wherein Q is O; S; N; NR$_9$; or C(R$_5$)$_2$;
wherein b is an integer from 1 to 2;
wherein $R_8$ is independently H; F; Cl; Br; I; NO$_2$; OH; =O; $C_1$–$C_4$ alkyl; $C_1$–$C_4$ alkoxy; $C_1$–$C_4$ hydroxyalkyl; $C_1$–$C_4$ methoxyalkyl; $C_1$–$C_4$ monohaloalkyl; $C_1$–$C_4$ polyhaloalkyl; N(R$_5$)$_2$; NHCOR$_5$; N(COR$_5$)$_2$; NHCO$_2$R$_5$; NHCONHR$_5$; NHSO$_2$R$_5$; N(SO$_2$R$_5$)$_2$; CO$_2$R$_5$; CON(R$_5$)$_2$; or SO$_2$N(R$_5$)$_2$;

wherein $R_9$ is H; $C_1$–$C_3$ alkyl; COR$_5$; CO$_2$R$_5$; CON(R$_5$)$_2$;
wherein $R_{10}$ is H; or $C_1$–$C_6$ alkyl;
wherein $R_{11}$ is H; COR$_5$; COR$_{12}$; SO$_2$R$_5$; SO$_2$R$_{12}$; and
wherein $R_{12}$ is phenoxy; phenyl, pyridyl; thiophenyl; or naphthyl; wherein the phenoxy, phenyl, pyridyl, thiophenyl or naphthyl is substituted with H, F, Cl, Br, I, CF$_3$, $C_1$–$C_4$ alkyl, $C_1$–$C_4$ alkoxy, $C_1$–$C_4$ alkylthio, NO$_2$, phenyl, pyridyl or thiophenyl; or a pharmaceutically acceptable salt thereof.

In one embodiment of the method described above the subject is a vertebrate, a mammal, a human or a canine. In another embodiment the compound is administered in combination with food.

The invention also provides for a method of modifying feeding behavior where the compound has the structure:

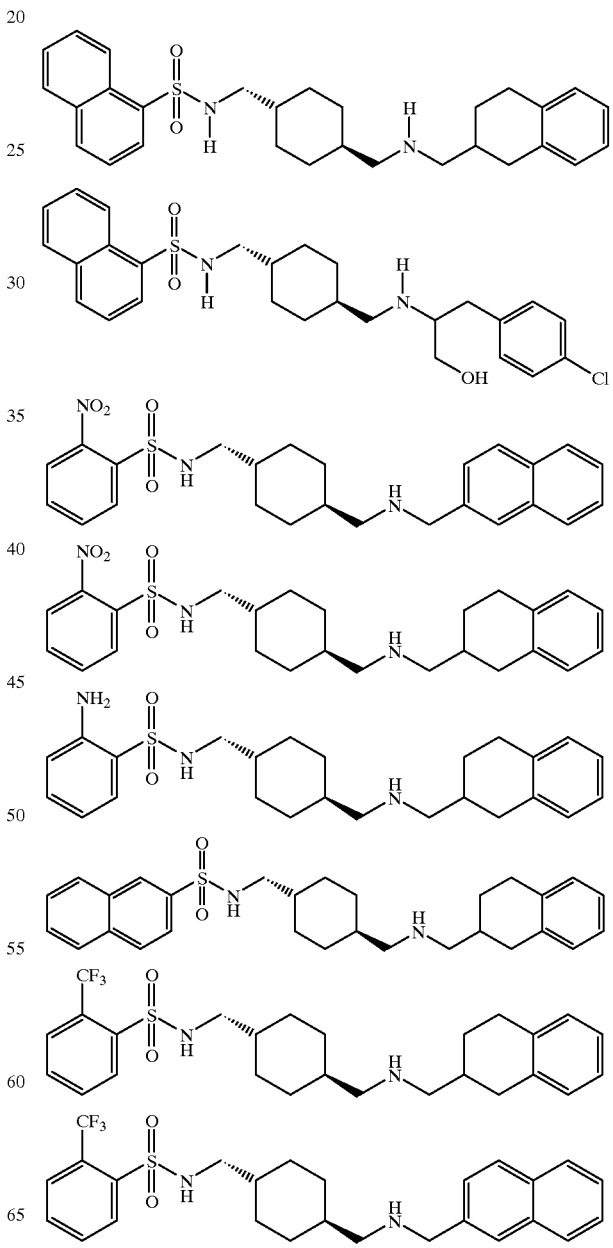

-continued

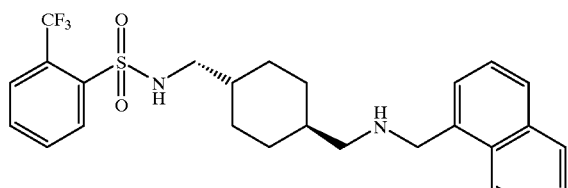

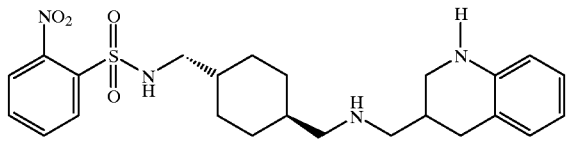

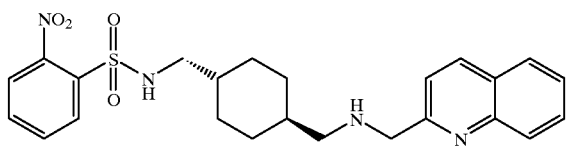

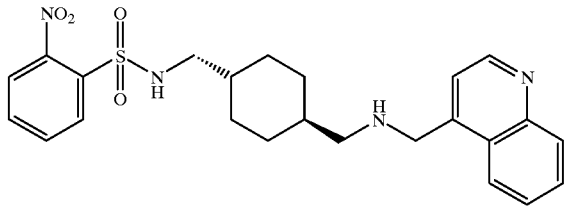

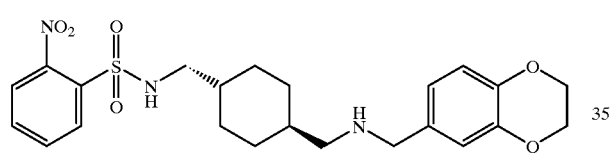

The invention further provides a method of treating a feeding disorder in a subject which comprises administering to the subject an amount of a compound effective to decrease consumption of food by the subject, where the compound has the structure:

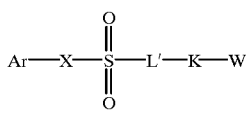

wherein Ar is

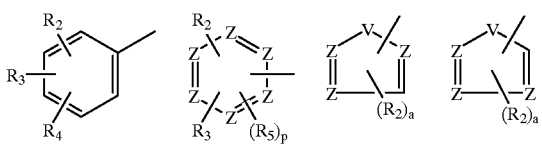

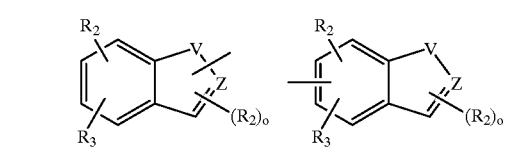

-continued

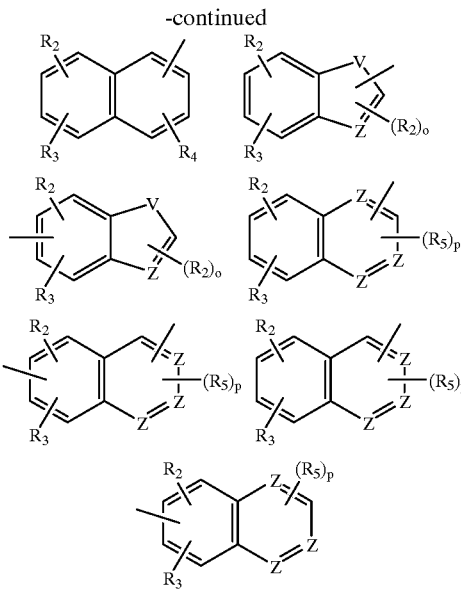

wherein each Z is independently N or C;

wherein each Y is independently N or C;

wherein p is an integer from 0 to 2;

wherein o is an integer from 0 to 1 and a is an integer from 0 to 3;

wherein V is S, O, N, or $NR_5$;

wherein X is a single bond or —NH—;

wherein each $R_2$ is independently H; F; Cl; Br; I; $NO_2$; OH; $C_1$–$C_4$ alkyl; $C_2$–$C_4$ alkenyl; $C_1$–$C_4$ alkoxy; $C_1$–$C_4$ hydroxyalkyl; $C_1$–$C_4$ methoxyalkyl; $C_1$–$C_4$ monohaloalkyl; $C_1$–$C_4$ polyhaloalkyl; $N(R_5)_2$; $NHCOR_5$; $N(COR_5)_2$; $NHCO_2R_5$; $NHCONHR_5$; $NHSO_2R_5$; $N(SO_2R_5)_2$; $CO_2R_5$; $CON(R_5)_2$; $SO_2N(R_5)_2$; phenoxy; phenyl; pyridyl; thiophenyl; naphthyl; phthalimide; $C_5$–$C_7$ lactam, $C_5$–$C_7$ cyclic imide, $C_5$–$C_7$ cyclic amino; wherein the phthalimide, lactam, cyclic imide, or cyclic amine is linked by nitrogen; and wherein the phenoxy, phenyl, pyridyl, thiophenyl, naphthyl, phthalimide, lactam, cyclic imide, or cyclic amine is substituted with H, F, Cl, Br, I, $CF_3$, $C_1$–$C_4$ alkyl, $C_1$–$C_4$ alkoxy, $C_1$–$C_4$ alkylthio, or $NO_2$;

wherein each $R_3$ is independently H; F; Cl; Br; I; $NO_2$; OH; $C_1$–$C_4$ alkyl; $C_2$–$C_4$ alkenyl; $C_1$–$C_4$ alkoxy; $C_1$–$C_4$ hydroxyalkyl; $C_1$–$C_4$ methoxyalkyl; $C_1$–$C_4$ monohaloalkyl; $C_1$–$C_4$ polyhaloalkyl; $N(R_5)_2$; $NHCOR_5$; $N(COR_5)_2$; $NHCO_2R_5$; $NHCONHR_5$; $NHSO_2R_5$; $N(SO_2R_5)_2$; $CO_2R_5$; $CON(R_5)_2$; $SO_2N(R_5)_2$; or $R_2$ and $R_3$ present on adjacent carbon atoms can constitute $C_5$–$C_7$ cycloalkyl, $C_5$–$C_7$ heterocycloalkyl or $C_5$–$C_7$ heteroaryl;

wherein each $R_4$ is independently H; F; Cl; Br; I; $NO_2$; OH; $C_1$–$C_4$ alkyl; $C_1$–$C_4$ alkoxy; $C_1$–$C_4$ hydroxyalkyl; $C_1$–$C_4$ methoxyalkyl; $C_1$–$C_4$ monohaloalkyl; $C_1$–$C_4$ polyhaloalkyl; $N(R_5)_2$; $NHCOR_5$; $N(COR_5)_2$; $NHCO_2R_5$; $NHCONHR_5$; $NHSO_2R_5$; $N(SO_2R_5)_2$; $CO_2R_5$; $CON(R_5)_2$; or $SO_2N(R_5)_2$;

wherein each $R_5$ is independently H; $C_1$–$C_3$ alkyl; $C_1$–$C_3$ monohaloalkyl; or $C_1$–$C_3$ polyhaloalkyl;

wherein L' is —NR$_1$—L— or

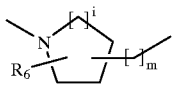

wherein L is C$_3$–C$_9$ alkyl; C$_3$–C$_9$ alkenyl; C$_3$–C$_9$ alkynyl;

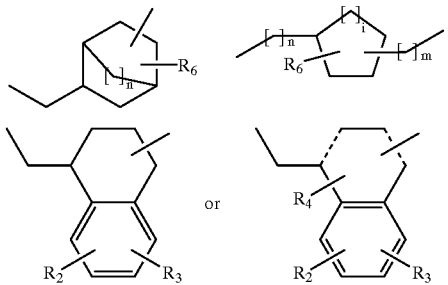

or wherein R$_1$ is H; or C$_1$–C$_3$ straight chained alkyl;
wherein the alkyl, alkenyl or alkynyl is substituted with H, OR$_5$, CN, C$_1$–C$_6$ alkyl, CH$_2$OR$_5$, CON(R$_5$)$_2$, CO$_2$R$_5$, phenyl, pyridyl, thiophenyl or naphthyl;
wherein one dashed line is a double bond and the other dashed line is a single bond;
wherein each R$_6$ is independently H; CN; OR$_5$; C$_1$–C$_5$ alkyl; CH$_2$OR$_5$; CON(R$_5$)$_2$; CO$_2$R$_5$; phenyl; pyridyl; thiophenyl or naphthyl; wherein the phenyl, pyridyl, thiophenyl or naphthyl is substituted with H, F, Cl, Br, I, CF$_3$, C$_1$–C$_4$ alkyl, C$_1$–C$_4$ alkoxy, C$_1$–C$_4$ alkylthio, or NO$_2$;
wherein i is an integer from 1 to 4; wherein n is an integer from 0 to 3; wherein m is an integer from 0 to 3;
wherein K is —CH$_2$—NR$_{10}$—CHR$_7$—(CH$_2$)$_j$—; —CH$_2$—NR$_{10}$—CO—(CH$_2$)$_j$—; —CH$_2$—NH—CO—NH—(CH$_2$)$_j$—; —CO—NH—CHR$_7$—(CH$_2$)$_j$—; —CH$_2$—NR$_{10}$—CO—CHR$_7$—(CH$_2$)$_j$; —CH$_2$—NR$_{10}$—CS—(CH$_2$)$_j$—; —CH$_2$—NH—CS—NH—(CH$_2$)$_j$—; —CS—NH— CHR$_7$—(CH$_2$)$_j$—; or —CH$_2$—NR$_{10}$—CS—CHR$_7$—(CH$_2$)$_j$; or —CH$_2$—N=CSR$_1$—NH—(CH$_2$)$_j$ ;
wherein j is an integer from 0 to 3;
wherein R$_7$ is H; C$_1$–C$_6$ alkyl; CH$_2$OR$_5$; (CH$_2$)$_p$NHCO$_2$R$_5$; (CH$_2$)$_p$NHSO$_2$R$_5$; CH$_2$N(R$_{11}$)$_2$; phenyl; pyridyl; thiophenyl; or naphthyl;
wherein W is

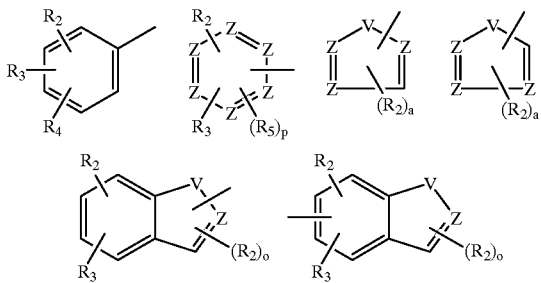

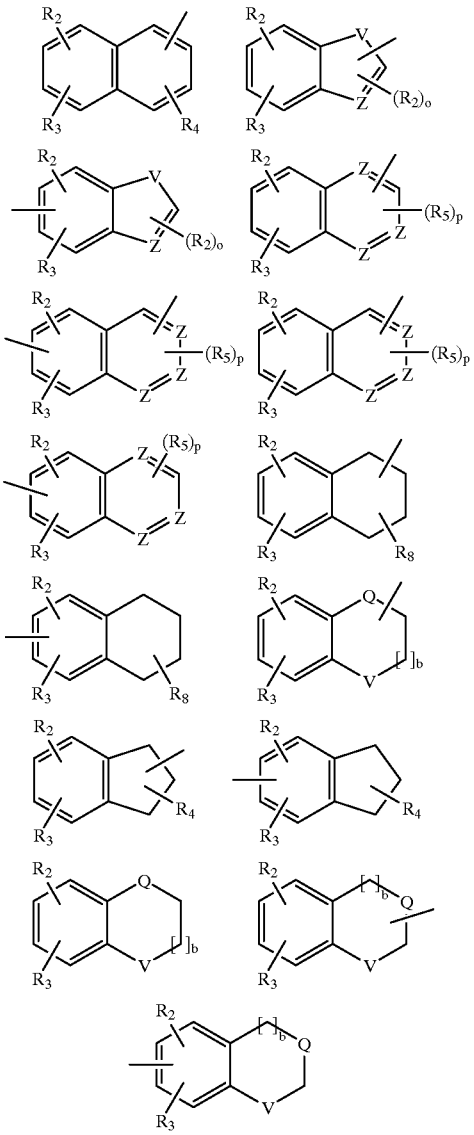

wherein Q is O; S; N; NR$_9$; or C(R$_5$)$_2$;
wherein b is an integer from 1 to 2;
wherein R$_8$ is independently H; F; Cl; Br; I; NO$_2$; OH; =O; C$_1$–C$_4$ alkyl; C$_1$–C$_4$ alkoxy; C$_1$–C$_4$ hydroxyalkyl; C$_1$–C$_4$ methoxyalkyl; C$_1$–C$_4$ monohaloalkyl; C$_1$–C$_4$ polyhaloalkyl; N(R$_5$)$_2$; NHCOR$_5$; N(COR$_5$)$_2$; NHCO$_2$R$_5$; NHCONHR$_5$; NHSO$_2$R$_5$; N(SO$_2$R$_5$)$_2$; CO$_2$R$_5$; CON(R$_5$)$_2$; or SO$_2$N(R$_5$)$_2$;
wherein R$_9$ is H; C$_1$–C$_3$ alkyl; COR$_5$; CO$_2$R$_5$; CON(R$_5$)$_2$;
wherein R$_{10}$ is H; or C$_1$–C$_6$ alkyl;
wherein R$_{11}$ is H; COR$_5$; COR$_{12}$; SO$_2$R$_5$; SO$_2$R$_{12}$; and
wherein R$_{12}$ is phenoxy; phenyl, pyridyl; thiophenyl; or naphthyl; wherein the phenoxy, phenyl, pyridyl, thiophenyl or naphthyl is substituted with H, F, Cl, Br, I, CF$_3$, C$_1$–C$_4$ alkyl, C$_1$–C$_4$ alkoxy, C$_1$–C$_4$ alkylthio, NO$_2$, phenyl, pyridyl or thiophenyl; or a pharmaceutically acceptable salt thereof.

In an embodiment of the present invention the feeding disorder may be obesity or bulimia. In another embodiment of the present invention the subject is a vertebrate, a mammal, a human or a canine. The invention also provides for the decrease in the consumption of food by the subject by the compound inhibiting the activity of the subject's Y5 receptor.

The invention further provides a method of treating a feeding disorder in a subject which comprises administering to the subject an amount of one of the following compounds:

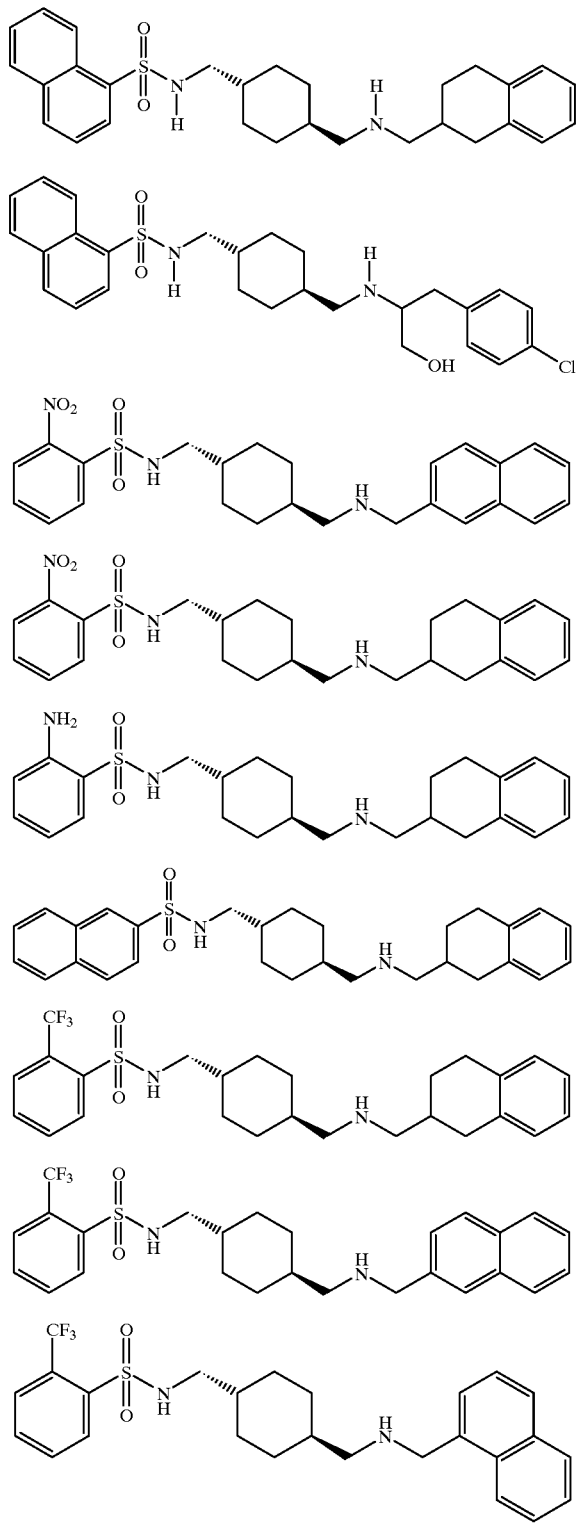

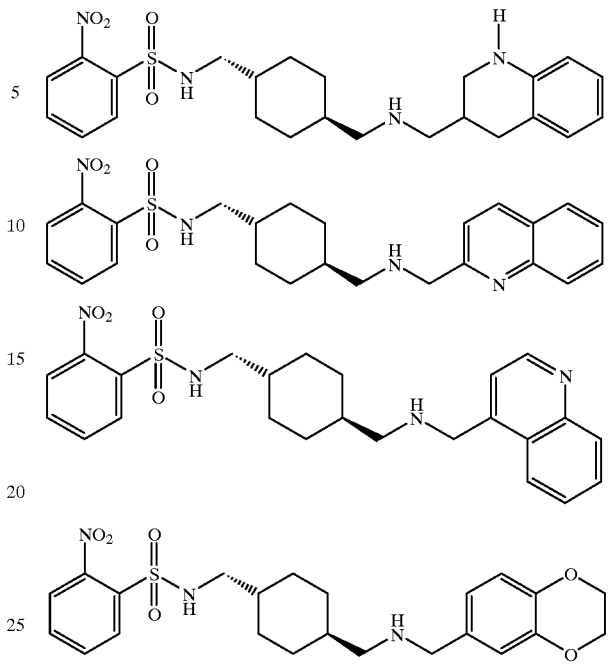

This invention also provides a method for treating a disorder in a subject which is alleviated by administering to the subject an amount of a compound described herein which is a Y5 receptor antagonist.

This invention additionally provides a method of treating obesity in a subject which comprises administering to the subject an amount of a Y5 receptor antagonist compound described herein.

This invention additionally provides a method of treating non-feeding disorders in a subject which comprises administering to the subject an amount of a compound described herein which is a Y5 receptor antagonist.

This invention further provides that any of the methods for treating may comprise administering to the subject a plurality of compounds described herein.

The invention also provides for the (−) and (+) enantiomers of the compounds of the subject application described herein. Included in this invention are pharmaceutically acceptable salts and complexes of all of the compounds described herein. The salts include but are not limited to the acids and bases listed herein. The following inorganic acids; hydrochloric acid, hydrofluoric acid, hydrobromic acid, hydroiodic acid, sulfuric acid and boric acid. The organic acids; acetic acid, trifluoroacetic acid, formic acid, oxalic acid, malonic acid, succinic acid, fumaric acid, tartaric acid, maleic acid, citric acid, methanesulfonic acid, trifluoromethanesulfonic acid, benzoic acid, glycolic acid, lactic acid and mandelic acid. The following inorganic bases; ammonia, hydroxyethylamine and hydrazine. The following organic bases; methylamine, ethylamine, propylamine, dimethylamine, diethylamine, trimethylamine, triethylamine, ethylenediamine, hydroxyethylamine, morpholine, piperazine and guanidine. This invention further provides for the hydrates and polymorphs of all of the compounds described herein.

This invention further provides for the metabolites and precursors of the compounds of the present invention. The in vivo actions of numerous enzymes responsible for the generation of metabolites of pharmaceutical compounds are well-known in the art. For example, ethers may be modified to alcohols, or esters may be modified by esterases to yield acids as products. Knowledge of the activities of endogenous enzymes also allows the design of precursors or prodrugs of the compounds of the present invention, which when administered to a subject, such as a vertebrate or a human, are expected to yield metabolites which include the compounds of the present invention. For example, secondary amines may be modified by various substituents, such as methyl, alkanoyl, aroyl, or alkyl or aryl carbamates may be formed, which are expected to yield the compounds of the present invention when acted upon in vivo by endogenous enzymes. Such modifications are intended only as illustrative examples, and are not intended to limit the scope of the present invention, as such modifications and techniques therefor are well-known in the art.

The invention also provides a pharmaceutical composition comprising a therapeutically effective amount of the compounds described above and a pharmaceutically acceptable carrier. In the subject invention a "therapeutically effective amount" is any amount of a compound which, when administered to a subject suffering from a disease against which the compounds are effective, causes reduction, remission, or regression of the disease. In one embodiment the therapeutically effective amount is an amount from about 0.01 mg per subject per day to about 500 mg per subject per day, preferably from about 0.1 mg per subject per day to about 60 mg per subject per day and most preferably from about 1 mg per subject per day to about 20 mg per subject per day. In the practice of this invention the "pharmaceutically acceptable carrier" is any physiological carrier known to those of ordinary skill in the art useful in formulating pharmaceutical compositions.

In another embodiment the pharmaceutical carrier may be a liquid and the pharmaceutical composition would be in the form of a solution. In yet another embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. Sterile liquid carriers can also be utilized for intranasal administration, for example with the use of a pressurized composition, or for inhalatory administration. The liquid carrier for pressurized compositions can be halogenated hydrocarbon or other pharmaceutically acceptable propellant.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The compound can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

One skilled in the art will readily appreciate that appropriate biological assays will be used to determine the therapeutic potential of the claimed compounds for treating the above noted disorders.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Synthetic Methods

The compounds of the present invention may be synthesized according to the methods described in Schemes 1–4, as described herein. It is generally preferred that the respective product of each process step, as described hereinbelow, is separated and/or isolated prior to its use as starting material for subsequent steps. Separation and isolation can be effect by any suitable purification procedure such as, for example, evaporation, crystallization, column chromatography, thin layer chromatography, distillation, etc. While preferred reactants have been identified herein, it is further contemplated that the present invention would include chemical equivalents to each reactant specifically enumerated in this disclosure.

Temperatures are given in degrees Centigrade (° C.). The structure of final products, intermediates and starting materials is confirmed by standard analytical methods, e.g., microanalysis and spectroscopic characteristics (e.g. MS, IR, NMR). Unless otherwise specified, chromatography is carried out using silica gel. Flash chromatography refers to medium pressure column chromatography according to Still et al., J. Org. Chem. 43, 2921 (1978).

Scheme 1

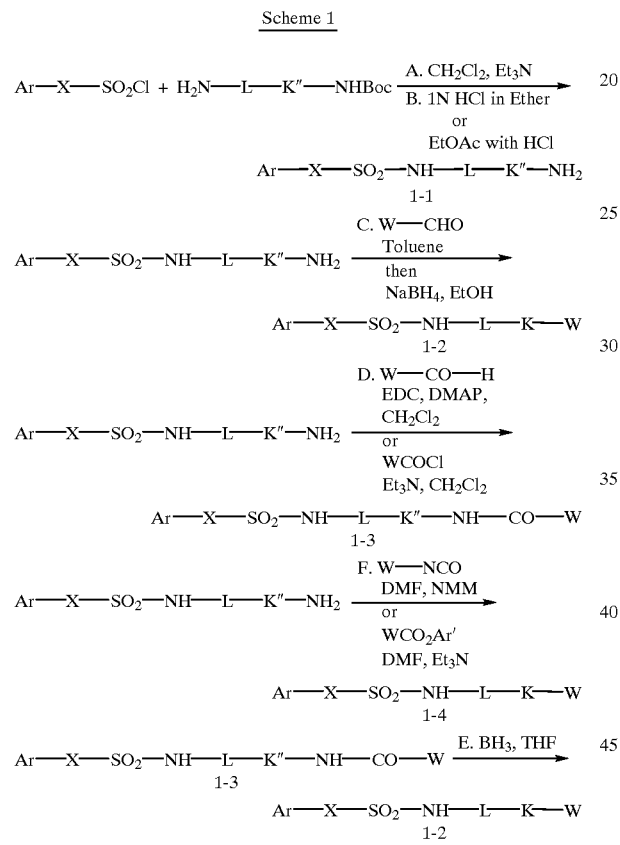

Scheme 2

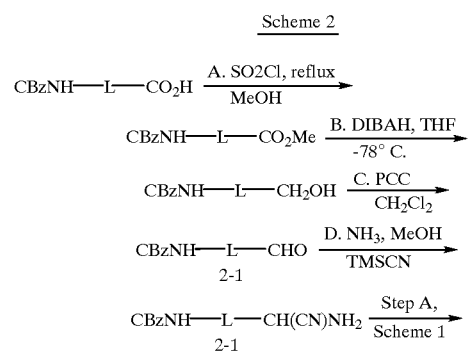

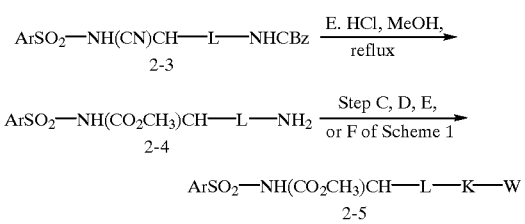

Scheme 3

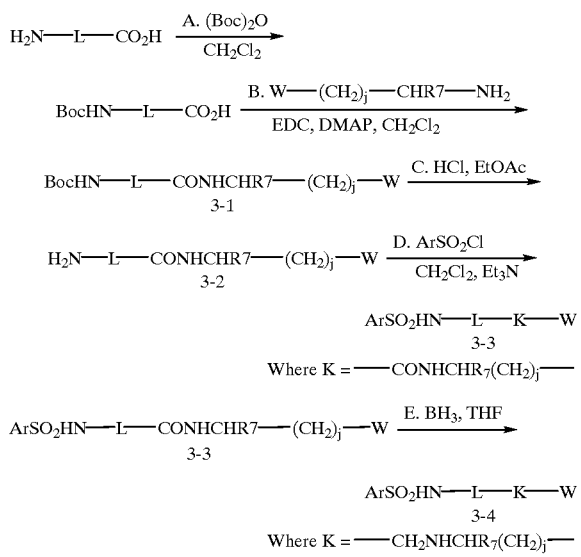

Scheme 4

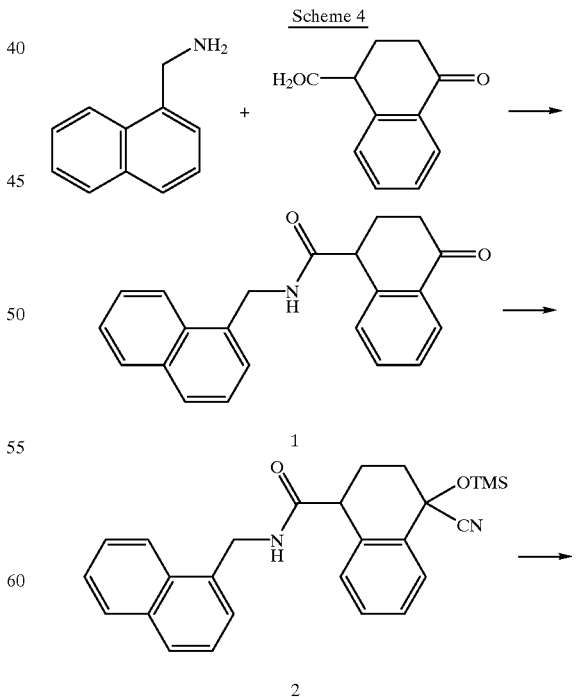

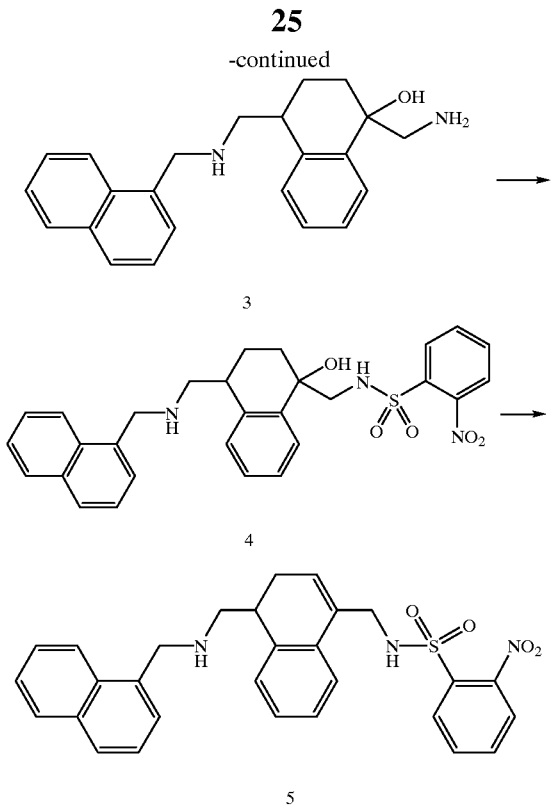

Synthesis of Compounds According to Scheme 1

Preparation of the compounds of the present invention having the structure shown in Formula 1-2, Scheme 1, was carried out using well-known methodology for the preparation of a sulfonamide or sulfamide from an amine. Preferably the appropriate arylsulfonyl or arylsulfamoyl halide, preferably the chloride (i.e., Ar—X—SO$_2$Cl), is reacted with a monoprotected linear or cyclic alkylamine (Krapcho and Kuell, *Synth. Comm.* 20(16):2559–2564, 1990) comprising H$_2$N—L—K", where K" comprises methylene, in the presence of a base such as a tertiary amine, e.g., triethylamine, dimethylaminopyridine, pyridine or the like, in an appropriate solvent (e.g. CHCl$_3$, CH$_2$Cl$_2$) as shown in Scheme 1, step A, followed by deprotection of the resulting amine as shown in Scheme 1, Step B, all under mild conditions (typically room temperature), to yield the deprotected amine of Formula 1-1. Alternatively, the primary amine H$_2$N—L may be replaced with a secondary amine wherein L comprises a piperidine. The arylsulfonyl or arylsulfamoyl halides are either known in the art or can be prepared according to methods well known in the art.

The deprotected amine may be converted to the product amine of Formula 1-2 by either a single step or two step reductive amination with an aryl substituted aldehyde W—CHO as shown in Scheme 1, Step C, in the presence of a solvent such as toluene or dioxane, at elevated temperature, followed by reduction using sodium borohydride in a solvent such as ethanol. The K" amine and the aldehyde carbon attached to W together form K in the product.

Compounds of Formula 1-3 in Scheme 1, wherein R$_1$ is H and j=0 and K comprises an amide, may be synthesized from the compound of Formula 1-1 by amidation using suitable methods such as those taught in "The Peptides," Vol. 1 (Gross and Meinehofer, Eds. Acaemic Press, N.Y., 1979). For example, the compound of Formula 1-1 may be treated with a carboxylic acid derivative of W in the presence of 1-(3-dimethylaminopropyl)-3-ethylcarbodiimide hydrochloride (EDC) and dimethylaminopyridine (DMAP) in a suitable solvent such as CH$_2$Cl$_2$ as shown in Scheme 1, Step D, at room temperature in an inert atmosphere of argon or nitrogen, to yield the amide compound of Formula 1-3. As in the previous method, the K" amine and the carboxylic acid carbon attached to W together form K in the product.

Alternatively, the compound of Formula 1-3 may be synthesized by acylation of the amine of Formula 1-1 using the acid chloride of W, i.e., WCOCl or W(CH$_2$)$_j$COCl where j is an integer from 1 to 3, in a solvent such as CH$_2$Cl$_2$ and a suitable tertiary amine such as triethylamine, at room temperature. Again, the K" amine and the acid chloride carbon attached to W together form K in the product.

This method also provides an alternative path to the compounds of Formula 1-2 by reduction of the amide of Formula 1-3 using borane-tetrahydorfuran (THF) complex, in THF as shown in Scheme 1, Step E, at elevated temperature in an inert atmosphere.

Compounds of Formula 1-4 in Scheme 1 where K comprises a ureido moiety may be synthesized by urea formation between the the compound of Formula 1-1 and a substituted aryl isocyanate or aryl carbamate, as shown in Scheme 1, Step F, in a suitable solvent and a suitable tertiary amine such as triethylamine and N-methylmorpholine, at room temperature in an inert atmosphere. The ureido moiety comprising K is formed between the K" amine and the isocyanate (or isothiocyanate) attached to W, or between K" and the carbamate derivative of W. Alternatively, compounds containing a thiourea moiety instead of a urea moiety may be synthesized similarly by simply replacing the aryl isocyanate described above with an aryl isothiocyanate.

Suitable aryl carbamates may be of the form WCO$_2$Ar' where W is for example

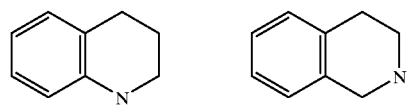

and Ar' may be for example 4-nitrophenyl.

Synthesis of the Compounds of Table 1

As an illustrative example of the synthesis of the compounds shown in Table 1, the synthesis of Example 1 from Table 1, is provided below:

N-[6{(Naphthalen-2-ylmethyl) -amino}-hexyl]-2-nitrobenzenesulfonamide

Step A, Scheme 1

[6-(2-Nitrobenzenesulfonylamino)-hexyl]-carbamic acid t-butyl Ester

To a stirred solution of N-Boc 1,6-diaminohexane hydrochloride (1.51 g, 6 mmol) and triethyle amine (1.31 g, 13 mmol) in 50 mL methylene chloride was added 2-Nitrobenzenesulfonyl chloride (1.326 g, 6 mmol). The reaction mixture was stirred for 6 h at room temperature, quenched with brine, and extracted with methylene chloride (2×50 mL). The organic layer was washed with brine (a saturated solution of sodium chloride in water, unless otherwise specified), dried over anhydrous sodium sulfate, and concentrated in vacuo to yield the titled compound as yellow oil (2.1 g, 87%).

Step B, Scheme 1

N-(6-Aminohexyl)-2-nitrobenzenesulfonamideHydrochloride

To a stirred solution of [6-(2-Nitrobenzenesulfonylamino)-hexyl]-carbamic acid t-butyl ester (2.0 g, 4.9 mmol) in 25 mL of methylene chloride at room temperature was added 3 mL of saturated HCl solution in ethyl acetate and stirred for 4 h. The precipitated solid was filtered to yield the titled compound as white solid (1.58 g, 95%); mp 161–162° C.

Step C, Scheme 1

N-[6{(Naphthalen-2-ylmethyl)-amino}-hexyl]-2-nitrobenzenesulfonamide

A mixture of N-(6-Aminohexyl)-2-nitrobenzenesulfonamide hydrochloride (0.67 g, 2.0 mmol) and 2-naphthaldehyde (0.32 g, 2.1 mmol) in 75 mL of toluene was refluxed using a Dean Stark trap for 20 h. The reaction mixture was concentrated in vacuo. The residue was dissolved in ethanol (40 mL) and sodium borohyride (0.020 g, 6.0 mmol) was added. After the reaction was complete (6 h), the solvent was evaporated and residue taken up in 30 mL of saturated sodium chloride solution and extracted with ethyl acetate (3×40 mL), washed with saturated sodium chloride solution, dried over sodium sulfate and concentrated to afford an oil. The oil was flash chromatographed over silica gel to afford the titled compound (0.16 g, 37%) which was converted into hydrochloride salt (mp 169° C.).

An example of the use of the alternative path to the compounds of Formula 1-2 by reduction of the amide of Formula 1-3 using borane-THF complex as previously described for Scheme 1, Step E, is provided for Example 15 of Table 1, as follows:

N-[6{(1,2,3,4-tetrahydronaphthalen-2-ylmethyl)-amino}-hexyl]-2-aminobenzenesulfonamide To a solution of 1,2,3,4-tetrahydro-2-naphthalencarboxylic acid[6-(2-nitrobenzenesulfonylamino)-hexyl]-amide (0.090 g, 0.19 mmol) in tetrahydrofuran (5 mL) cooled to 0° C. was added 2 mL 1M solution of borane:THF complex and the reaction mixture was refluxed for 12 h. The reaction mixture was cooled in an ice bath and quenched with 2 mL of 1N HCl. The reaction mixture was neutralized with 10% aqueous sodium hydroxide solution and extracted with ethyl acetate (3×25 mL). The organic phase was washed with brine, dried over sodium sulfate, and evaporated in vacuo to afford an oil which was purified by preparative TLC to afford the titled compound (0.06 g, 70%); hydrochloride salt mp (162–163° C.).

Using appropriately substituted starting materials, the other Examples shown in Table 1 were synthesized as described above, with the exception of Example 52. The compound of Example 52 in Table 1 was synthesized similarly, except that before deprotection of the amine of Formula 1-1 in Scheme 1 Step B, the sulfonyl nitrogen was alkylated with methyl iodide in dimethylformamide at room temperature to afford the N-methylated sulfonamide product (Sato et al., 1995), which was subsequently deprotected as in Scheme 1, Step B, for use in the remainder of Scheme 1.

Other n-alkyl derivatives may be prepared similarly, using an n-alkyl halide in an inert solvent such as dimethylformamide as described above.

TABLE 1

| No. | Ar | X | $R_1$ | L | K | W | mp | Analysis |
|---|---|---|---|---|---|---|---|---|
| 1 | 2-nitrophenyl | — | H | —$(CH_2)_5$— | $CH_2NHCH_2$ | 2-naphthyl | 169 | $C_{23}H_{26}N_3O_4S$ + HCl + 0.05 $CHCl_3$ |
| 2 | 2-naphthyl | — | H | —$(CH_2)_5$— | $CH_2NHCH_2$ | 2-naphthyl | 174 | $C_{27}H_{30}N_2O_2S$ + HCl |
| 3 | 2-naphthyl | — | H | —$(CH_2)_4$— | $CH_2NHCH_2$ | 2-naphthyl | 194–5 | $C_{26}H_{28}N_2O_4S$ + HCl + 0.04 $CHCl_3$ |
| 4 | 1-naphthyl | — | H | —$(CH_2)_5$— | $CH_2NHCH_2$ | 1-naphthyl | 190–1 | $C_{27}H_{30}N_2O_2S$ + HCl |

TABLE 1-continued

| No. | Ar | X | R₁ | L | K | W | mp | Analysis |
|---|---|---|---|---|---|---|---|---|
| 5 | 4-propylphenyl | — | H | —(CH$_2$)$_5$— | CH$_2$NHCH$_2$ | 2-naphthyl | 149–50 | |
| 6 | 2-(CF$_3$)phenyl | — | H | —(CH$_2$)$_5$— | CH$_2$NHCH$_2$ | 2-naphthyl | 158 | C$_{24}$H$_{27}$N$_2$O$_2$SF$_3$ + HCl |
| 7 | 2-fluorophenyl | — | H | —(CH$_2$)$_5$— | CH$_2$NHCH$_2$ | 2-naphthyl | 111–12 | — |
| 8 | 2-nitrophenyl | — | H | —(CH$_2$)$_5$— | CH$_2$NHCH$_2$ | 3,4-dimethoxyphenyl | 139 | C$_{21}$H$_{29}$N$_3$O$_6$S + HCl + 0.1H$_2$O |
| 9 | 3-(CF$_3$)phenyl | — | H | —(CH$_2$)$_5$— | CH$_2$NHCH$_2$ | 2-naphthyl | 172–4 | C$_{24}$H$_{27}$N$_2$O$_2$SF$_3$ + HCl |
| 10 | 2-(CF$_3$)phenyl | — | H | —(CH$_2$)$_5$— | CH$_2$NHCH$_2$ | 1-naphthyl | 167 | C$_{24}$H$_{28}$N$_2$O$_2$SF$_3$ + HCl |
| 11 | 1-naphthyl | — | H | —(CH$_2$)$_5$— | CH$_2$NHCH$_2$ | 2-naphthyl | 139–40 | C$_{27}$H$_{31}$N$_2$O$_2$S + HCl |
| 12 | phenyl | — | H | —(CH$_2$)$_5$— | CH$_2$NHCH$_2$ | 2-naphthyl | 194–6 | C$_{23}$H$_{26}$N$_2$O$_2$S + HCl |
| 13 | 2-(methoxycarbonyl)phenyl | — | H | —(CH$_2$)$_5$— | CH$_2$NHCH$_2$ | 2-naphthyl | 119–20 | C$_{25}$H$_{30}$N$_2$O$_4$S + HCl |

TABLE 1-continued
| No. | Ar | X | R₁ | L | K | W | mp | Analysis |
|---|---|---|---|---|---|---|---|---|
| 14 | 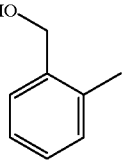 | — | H | —(CH₂)₅— | CH₂NHCH₂ | 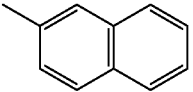 | 120–1 | C₂₄H₃₀N₂O₃S + HCl |
| 15 | 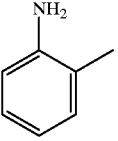 | — | H | —(CH₂)₅— | CH₂NHCH₂ | 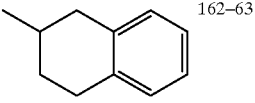 | 162–63 | C₂₃H₃₂N₃O₂S + 2.0 HCl |
| 16 | 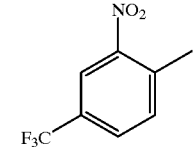 | — | H | —(CH₂)₅— | CH₂NHCH₂ | 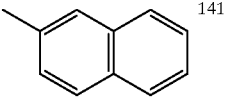 | 141 | C₂₄H₃₆N₃O₄S + HCl + 0.1CH₂Cl₂ |
| 17 | 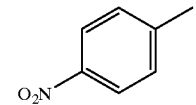 | — | H | —(CH₂)₅— | CH₂NHCH₂ | 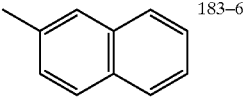 | 183–6 | C₂₃H₂₇N₃O₄S + HCl |
| 18 | 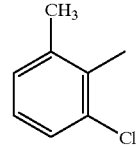 | — | H | —(CH₂)₅— | CH₂NHCH₂ | 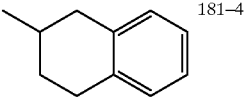 | 181–4 | |
| 19 | 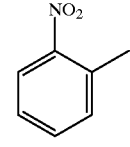 | — | H | —(CH₂)₇— | CH₂NHCH₂ | 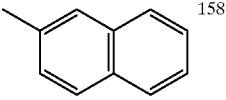 | 158 | C₂₆H₃₁N₃O₄S + HCl |
| 20 | 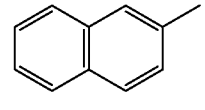 | — | H | —(CH₂)₇— | CH₂NHCH₂ | 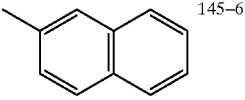 | 145–6 | C₂₉H₃₄N₂O₂S + HCl |
| 21 | 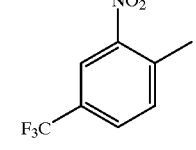 | — | H | —(CH₂)₇— | CH₂NHCH₂ | 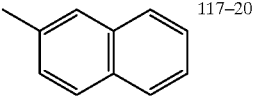 | 117–20 | C₂₆H₃₀N₃O₄SF₃ + HCl |
| 22 | 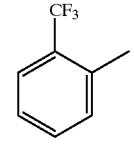 | — | H | —(CH₂)₇— | CH₂NHCH₂ | 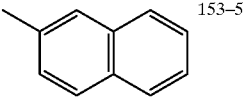 | 153–5 | C₂₅H₃₃N₃O₂SF₃ + HCl |

TABLE 1-continued

| No. | Ar | X | R₁ | L | K | W | mp | Analysis |
|---|---|---|---|---|---|---|---|---|
| 23 | 2-methylaniline (o-NH₂) | — | H | —(CH₂)₇— | CH₂NHCH₂ | 2-naphthyl | 166–8 | $C_{25}H_{33}N_3O_2S$ + 2.0 HCl |
| 24 | 2-(hydroxymethyl)phenyl | — | H | —(CH₂)₇— | CH₂NHCH₂ | 2-naphthyl | 120–2 | $C_{26}H_{34}N_2O_3S$ + HCl + 0.05 CHCl₃ |
| 25 | 2-methylnitrobenzene (o-NO₂) | — | H | —(CH₂)₇— | CH₂NHCH₂ | 2-tetralinyl | 134–6 | $C_{25}H_{35}N_3O_4S$ + HCl |
| 26 | 2-methylaniline (o-NH₂) | — | H | —(CH₂)₇— | CH₂NHCH₂ | 2-tetralinyl | 129–31 | $C_{25}H_{37}N_3O_2S$ + 2.0 HCl |
| 27 | 2-(hydroxymethyl)phenyl | — | H | —(CH₂)₇— | CH₂NHCH₂ | 2-tetralinyl | 113–4 | $C_{26}H_{38}N_3O_3S$ + HCl + 0.1 CHCl₃ |
| 28 | 2-naphthyl | — | H | trans-4-ethylcyclohexyl | CH₂NHCH₂ | 2-naphthyl | 250–1 | $C_{29}H_{32}N_3O_2S$ + HCl |
| 29 | 2-naphthyl | — | H | trans-4-ethylcyclohexyl | CH₂NHCH₂ | 1-naphthyl | 195 | $C_{29}H_{31}N_2O_2S$ + HCl + 0.25 H₂O |
| 30 | 1-naphthyl | — | H | trans-4-ethylcyclohexyl | CH₂NHCH₂ | 1-naphthyl | 172 | $C_{29}H_{32}N_2O_2S$ + HCl + 0.25 CH₂Cl₂ |
| 31 | 2-naphthyl | — | H | trans-4-ethylcyclohexyl | CH₂NHCH₂ | 2-tetralinyl | 210 | $C_{29}H_{36}N_2O_2S$ + HCl |

TABLE 1-continued

| No. | Ar | X | R₁ | L | K | W | mp | Analysis |
|---|---|---|---|---|---|---|---|---|
| 32 | 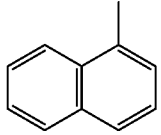 | — | H | 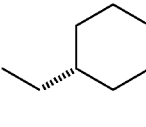 | CH₂NHCH₂ | 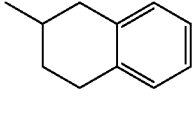 | 220 | C₂₉H₃₆N₂O₂S + HCl + 0.15 CH₂Cl₂ |
| 33 | 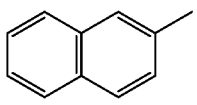 | — | H | 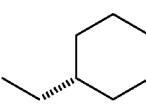 | CH₂NHCH₂ | 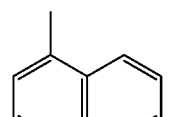 | 201 | C₂₉H₃₂N₂O₂S + HCl + 0.3 CHCl₃ |
| 34 | 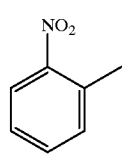 | — | H | 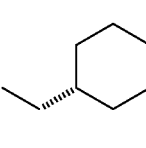 | CH₂NHCH₂ | 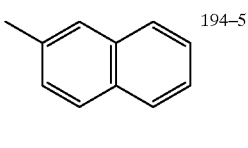 | 194–5 | C₂₅H₂₉N₃O₄S + HCl + 0.1 CHCl₃ |
| 35 | 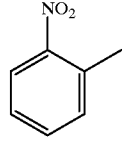 | — | H | 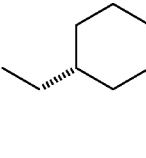 | CH₂NHCH₂ | 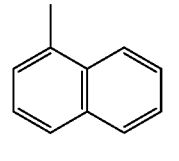 | Hygroscopic | C₂₅H₂₉N₃O₄S + HCl + 0.2 C₆H₁₄ |
| 36 | 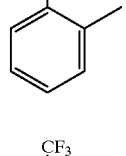 | — | H | 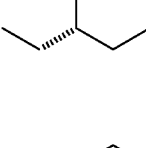 | CH₂NHCH₂ | 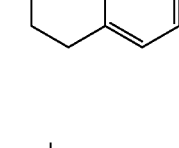 | 200–2 | C₂₅H₃₃N₃O₄S + HCl |
| 37 | 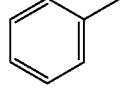 | — | H | 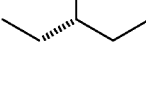 | CH₂NHCH₂ | 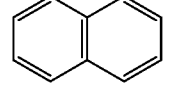 | 216–7 | C₂₆H₂₉N₂O₂SF₃ + HCl |
| 38 | 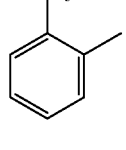 | — | H | 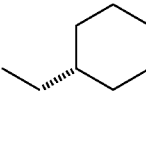 | CH₂NHCH₂ | 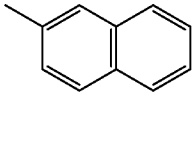 | 171–4 | C₂₆H₂₉N₂O₂SF₃ + HCl + 0.075 CHCl₃ |
| 39 | 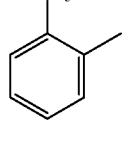 | — | H | 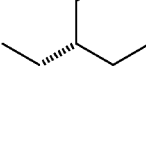 | CH₂NHCH₂ | 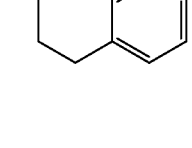 | 75–8 | C₂₆H₃₃N₂O₂SF₃ + HCl + 0.05 CHCl₃ |
| 40 | 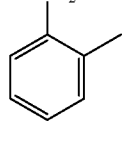 | — | H | 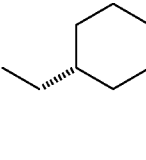 | CH₂NHCH₂ | 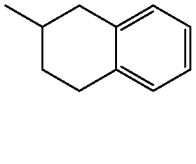 | 175–7 | C₂₆H₃₅N₃O₂S + 2 HCl + 0.8 Et₂O |

TABLE 1-continued
| No. | Ar | X | R₁ | L | K | W | mp | Analysis |
|---|---|---|---|---|---|---|---|---|
| 41 | 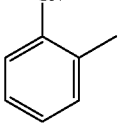 | — | H | 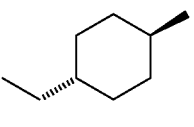 | CH₂NHCH₂ | 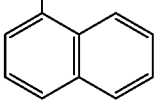 | Hygroscopic | C₂₆H₂₉N₃O₂S + HCl |
| 42 | 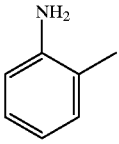 | — | H | 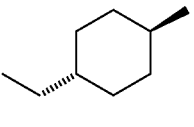 | CH₂NHCH₂ | 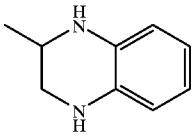 | 118–20 | C₂₆H₂₉N₃O₂S + 2.6 HCl |
| 43 | 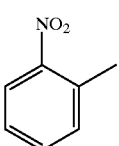 | — | H | 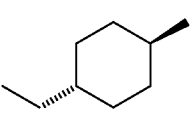 | CH₂NHCH₂ | 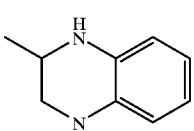 | 115 dec | C₂₃H₃₁N₆O₄S + 2.4 HCl |
| 44 | 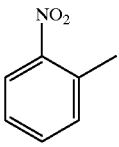 | — | H | 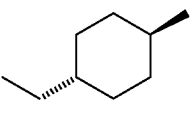 | CH₂NHCH₂ | 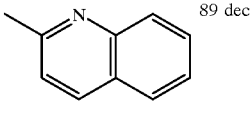 | 89 dec | C₂₄H₂₈N₄O₄S + 2 HCl |
| 45 | 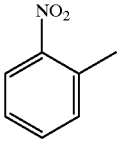 | — | H | 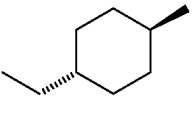 | CH₂NHCH₂ | 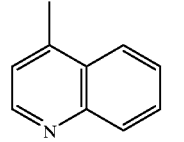 | 104–6 | C₂₄H₂₈N₄O₄S + 2 HCl + 0.25 CHCl₃ |
| 46 | 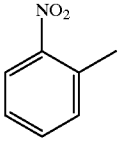 | — | H | 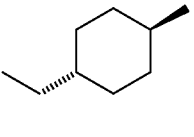 | CH₂NHCH₂ | 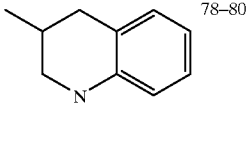 | 78–80 | C₂₄H₃₂N₄O₄S + 2 HCl + 0.65 CHCl₃ |
| 47 | 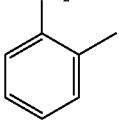 | — | H | 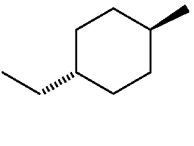 | CH₂NHCH₂ | 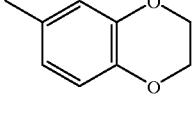 | 249–51 | C₂₃H₂₉N₃O₆S + HCl + 0.1 CHCl₃ |
| 48 | 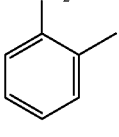 | — | H | 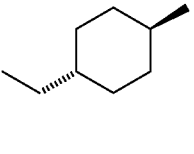 | CH₂NHCH₂ | 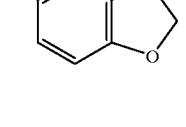 | 220–21 | C₂₂H₂₇N₃O₆S + HCl + 0.05 CHCl₃ |
| 49 | 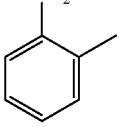 | — | H | 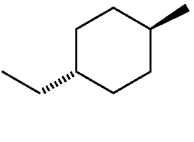 | CH₂NHCH₂ | 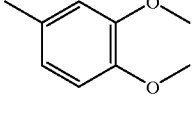 | 62–5 | C₂₃H₃₁N₃O₆S + HCl + 0.5 CHCl₃ |

TABLE 1-continued

| No. | Ar | X | R₁ | L | K | W | mp | Analysis |
|-----|----|----|----|---|---|---|----|----------|
| 50 | 2-NO₂, methyl-phenyl | — | H | cyclohexyl | CH₂NHCH₂ | 2-hydroxy-2-methyl-indane | 196–7 | $C_{24}H_{31}N_3O_5S$ + HCl |
| 51 | 2-NO₂, methyl-phenyl | — | H | cyclohexyl | CH₂NHCH₂ | 4-methyl-1-hydroxy-tetrahydronaphthalene | 57 | $C_{25}H_{33}N_3O_5S$ + HCl + 0.13 CHCl₃ |
| 52 | 2-naphthyl | — | CH₃ | cyclohexyl | CH₂NHCH₂ | 2-methyl-naphthyl | 235–6 | $C_{30}H_{34}N_2O_2S$ + HCl |

Synthesis of the Compounds of Table 2

As an illustrative example of the synthesis of the compounds shown in Table 2 as shown in Scheme 1, Step D, the synthesis of Example 53 from Table 2, is provided below:

1,2,3,4-Tetrahydro-2-naphthalencarboxylic Acid[6-(2-nitrobenzenesulfonylamino)-hexyl]-amide Step D, Scheme 1

1,2,3,4-Tetrahydro-2-naphthalencarboxylic Acid[6-(2-nitrobenzenesulfonylamino)-hexyl]-amide A mixture of N-(6-aminohexyl)-2-nitrobenzenesulfonamide hydrochloride (0.2 g, 0.58 mmol), EDC (0.252 g, 1.31 mmol), and DMAP (0.14 g, 1.21 mmol) in methylene chloride (30 mL) was stirred at room temperature for 0.5 h. 1,2,3,4-tetrahydronaphthalen-2-carboxylic acid (0.114 g, 0.65 mmol) was added to the reaction mixture and stirred at room temperature until the completion of the reaction (determined by TLC). The reaction mixture was washed with saturated ammonium chloride (3×30 mL), dried over sodium sulfate and concentrated in vacuo. The residue was flash chromatographed over silica gel to afford an oil (0.25 g, 93%).

Other compounds of Formula 1-3, as shown in Table 2, were synthesized using the methods described above, except for Examples 59 and 63. Example 59 was synthesized as shown in Scheme 1, except for the use of sulfamyl chloride starting material Ar—NH—SO₂Cl instead of the sulfonyl chloride Ar—SO₂Cl (Benson and Spillane, Chem, Rev. 80:151–186, 1980).

Example 63 of Table 2 was synthesized from the compound of Example 53 of Table 2 by reduction of the aryl nitro moiety using tin chloride in HCl/Acetic acid/H₂O at room temperature, to afford the amino aryl derivative (such as in Example 56, Table 2), which was then sulfonylated with alkyl sulfonyl chloride to afford the bis-sulfonylated compound of Example 63 as follows:

1,2,3,4-Tetrahydro-2-naphthalencarboxylic acid[6-{2-(bismethanesulfonylaminobenzenesulfonylamino)}-hexyl]-amide (a) 1,2,3,4-Tetrahydro-2-naphthalencarboxylic acid [6-(2-aminobenzenesulfonylamino)-hexyl]-amide To a solution of 1,2,3,4-Tetrahydro-2-naphthalencarboxylic acid[6-(2-nitrobenzenesulfonylamino)-hexyl]-amide (0.54 g, 1.17 mmol) in 5 mL of glacial acetic acid stirred at 0° C. was added a solution of tin chloride (1.32 g, 5.88 mmol)in 5 mL conc. HCl and 1 mL of water. The reaction mixture was warmed to room temperature and stirred for 3 h and poured over crushed ice (50 g). The reaction mixture was neutralized with 10% sodium hydroxide and extracted with chloroform (5×50 mL), dried over sodium sulfate and concentrated to afford yellow oil (0.48 g, 95%).

(b) 1,2,3,4-Tetrahydro-2-naphthalencarboxylic acid [6-{2-(bismethanesulfonylaminobenzenesulfonylamino)}-hexyl]-amide To a solution of 1,2,3,4-tetrahydro-2-naphthalencarboxylic acid[6-(2-aminobenzenesulfonylamino)-hexyl]-amide (0.075 g, 0.17 mmol) in chloroform (3 mL), and triethylamine (0.1 g, 1 mmol)stirred at 0° C. was added methane sulfonyl chloride (30 mL, 0.35 mmol) and the reaction mixture was stirred at room temperature for 3 h. Solvent was evaporated and purifications by preparative TLC afforded the titled compound as white solid (0.1 g, 97%); mp 70° C.

The amine of Example 56, Table 2, further may be acylated in the same manner as above in Example 63 but using suitable alkyl acyl chlorides instead of an alkyl sulfonyl chloride.

TABLE 2

| No. | Ar | X | R₁ | L | K | W | mp | Analysis |
|---|---|---|---|---|---|---|---|---|
| 53 | 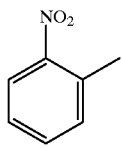 | — | H | —(CH₂)₅— | CH₂NHCO | 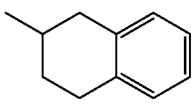 | Oil | C₂₃H₂₉N₃O₅S + 0.35CH₂Cl₂ |
| 54 | 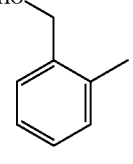 | — | H | —(CH₂)₅— | CH₂NHCO | 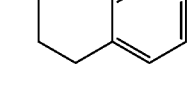 | Oil | C₂₄H₃₂N₂O₄S + 0.6 CHCl₃ |
| 55 | 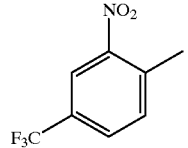 | — | H | —(CH₂)₅— | CH₂NHCO | 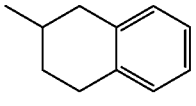 | Oil | C₂₄H₂₆N₃O₅SF₃ + 0.2 C₆H₁₄ |
| 56 | 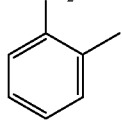 | — | H | —(CH₂)₅— | CH₂NHCO | 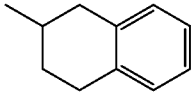 | 72–4 | C₂₃H₃₁N₃O₃S + 0.25 CH₂Cl₂ |
| 57 | 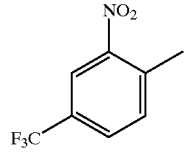 | — | H | —(CH₂)₅— | CH₂NHCO | 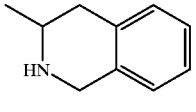 | 132 | C₂₃H₂₆N₄O₅SF₃ + HCl + 0.05 CHCl₃ |
| 58 | 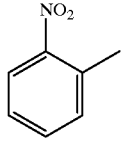 | — | H | —(CH₂)₅— | CH₂NHCO | 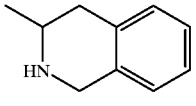 | 98 | C₂₂H₂₉N₄O₅S + HCl + 0.1 CHCl₃ |
| 59 | 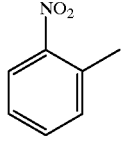 | NH | H | —(CH₂)₄— | CH₂NHCO | 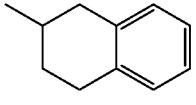 | Oil | C₂₂H₂₉N₄O₅S + 0.35 CH₂Cl₂ |
| 60 | 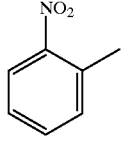 | — | H | —(CH₂)₅— | CH₂NHCO | 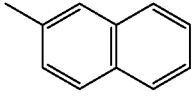 | Oil | C₂₃H₂₅N₃O₅S |
| 61 | 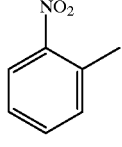 | — | H | —(CH₂)₅— | CH₂NHCO | 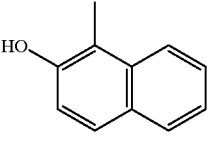 | 105 | C₂₃H₂₅N₃O₅S |

TABLE 2-continued
| No. | Ar | X | $R_1$ | L | K | W | mp | Analysis |
|---|---|---|---|---|---|---|---|---|
| 62 | 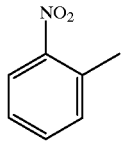 | — | H | —(CH$_2$)$_7$— | CH$_2$NHCO | 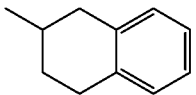 | Oil | $C_{25}H_{33}N_3O_5S$ + 0.15 CHCl$_3$ |
| 63 | 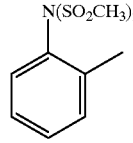 | — | H | —(CH$_2$)$_5$— | CH$_2$NHCO | 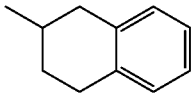 | 70 | $C_{25}H_{35}N_3O_7S_3$ |
| 64 | 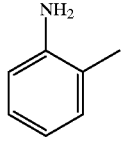 | — | H | 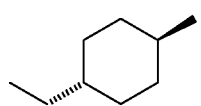 | CH$_2$NHCO | 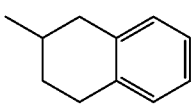 | 194–7 | $C_{25}H_{33}N_3O_3S$ + HCl + 0.2 CHCl$_3$ |
| 65 | 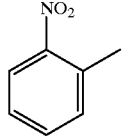 | — | H | 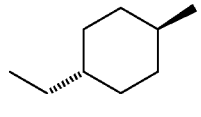 | CH$_2$NHCO | 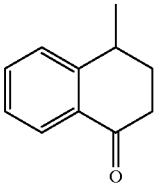 | 78–80 | $C_{25}H_{39}N_3O_6S$ + HCl + 0.3 CHCl$_3$ |
| 66 | 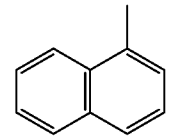 | — | H | 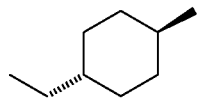 | CH$_2$NHCO | 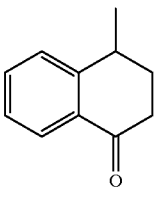 | 86–87 | $C_{29}H_{32}N_2O_4S$ + HCl + 0.35 CHCl$_3$ |
| 67 | 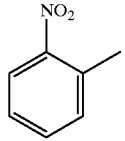 | — | H | 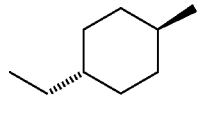 | CH$_2$NHCO | 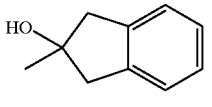 | 59–61 | $C_{29}H_{32}N_2O_4S$ + 0.2 CHCl$_3$ |
| 68 | 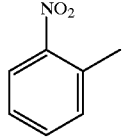 | — | H | 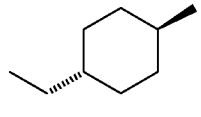 | CH$_2$NHCO | 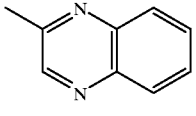 | 150–3 | $C_{23}H_{25}N_5O_5S$ + 0.25 CHCl$_3$ |
| 69 | 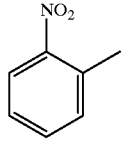 | — | H | 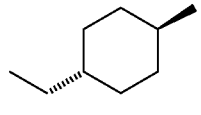 | CH$_2$NHCO | 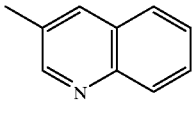 | 62–4 | $C_{24}H_{26}N_4O_5S$ + 0.3 CHCl$_3$ |

TABLE 2-continued

| No. | Ar | X | $R_1$ | L | K | W | mp | Analysis |
|---|---|---|---|---|---|---|---|---|
| 70 | 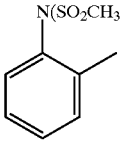 | — | H | 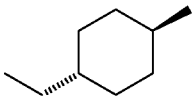 | $CH_2NHCO$ | 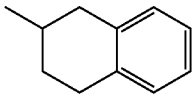 | 85–7 | $C_{27}H_{37}N_3O_7S_3$ + 0.25 $CHCl_3$ |

Synthesis of the compounds of Table 3

As an illustrative example of the synthesis of the compounds shown in Table 3 and Table 3a, as shown in Scheme 1, Step F, the synthesis of Example 71 from Table 3, is provided below:

Synthesis of Naphthalene-1-sulfonic acid{6-[3-(1-naphthyl)-uriedo]-hexyl}-amide

Step F, Scheme 1

To a solution of N-(6-aminohexyl)-1-naphthalenesulfonamide hydrochloride(0.1 g, 0.29 mmol) in 3 mL dimethylformamide and 50 mL N-methyl morpholine was added 1-naphthalene isocynate(68 μL, 0.4 mmol). The reaction mixture was stirred at room temperature for 6 h. Solvent was evaporated in vacuo and residue was purified by preparative TLC to afford white solid(110 mg, 79%); mp 105–106° C.

An example of the synthesis of a compound of Formula 1-4 in Scheme 1, using an aryl carbamate as previously described, is provided for Example 74 of Table 3, as follows:

3, 4-Dihydroquinoline-1-carboxylic acid[6-(2-trifluoromethylbenzenesulfonylamino)-hexyl]amide (a) 3, 4-Dihydro-2H-quinoline-1-carboxylic acid 4-nitrophenyl ester To a solution of tetrahydroisoquinoline (3.99 g, 30 mmol) in triethyl amine(6 g, 60 mmol) and dichloromethane(150 mL) cooled in ice bath was added p-nitrophenyl chloroformate (6.06 g, 30 mmol) drop wise over a period of 1 h. The reaction mixture was srirred at room temperature for 3 h and then washed with water (3×100 mL), dried over sodium sulfate and concentrated to afford an oil which was triturated with ether:hexane to afford the titled compound as yellow solid (5.9 g, 65%).

(b) 3, 4-Dihydroquinoline-1-carboxylic acid[6-(2-trifluoromethylbenzenesulfonylamino)-hexyl]amide:

To a solution of N-(6-Aminohexyl)-2-trifluoromethylbenzene sulfonamide Hydrochloride( 0.1 g, 0.27 mmol) dimethyl formamide (3 mL) and triethylamine (0.1 g, 1 mmol) was added 3, 4-Dihydro-2H-quinoline-1-carboxylic acid 4-nitrophenyl ester (0.09 g, 0.3 mmol) and the reaction mixture was stirred at room temperature for 4 h. Solvent was evaporated and purification by preparative TLC afford the titled compound as an oil (0.08 g, 61%).

Synthesis of the compounds of Table 3a

As illustrative examples of the synthesis of the compounds of Table 3a, as shown in Scheme 1, Step F, the syntheses of Examples 80–82 and 87 is provided below:

Example 80

1-[1-(Naphthalene-1-sulfonyl) -piperidine-4-ylmethyl]-3-naphthalene-1-ylmethylthiourea 1-Naphthalene-1-ylmethyl-3-piperidine-4-ylmethylthiourea To a solution of 1-naphthalenemethylisothiocyanate (2.8 g, 13.6 mmol) in 100 ml of MeOH-THF solution (1:1 mixture) was added 4-aminomethylpiperidine (3.1 ml, 27.0 mmol) in a portion and the resulting solution was stirred at reflux for 12 h. The reaction mixture was concentrated in vacuo, yielding oily mixture which was subjected to column chromatography (10% MeOH/CHCl₃) to yield 2.3 g (48%) of the desired product as an oil.

1-[-(Naphthalene-1-sulfonyl)-piperidine-4-ylmethyl]-3-naphthalene-1-ylmethylthiourea To a solution of the amine (0.34 g, 1.1 mmol) in 10 ml of pyridine was added 1-naphthalenesulfonyl chloride (0.30 ml, 1.3 mmol) in a portion and the resulting mixture was stirred at 25° C. for 12 h. The reaction mixture was subjected to column chromatography (50% Hexane/EtOAc) to yield 0.21 g (38%) of the desired product as yellow solid, which was recrystallized from EtOAc to provide 0.15 g of the product as white solid: mp 83–85° C.; Anal. Cal. For $C_{28}H_{29}N_3O_2S_2$ requires C, 66.77; H, 5.80; N, 8.34. Found: C, 64.32; H, 5.89; N, 8.27.

Example 81

2-methyl-1-[1-(naphthalene-1-sulfonyl)piperidine-4-ylmethyl]-3-naphthalene-1-ylmethylisothiourea To a solution of the thiourea of Example 80 (0.11 g, 0.32 mmol) in MeOH was added MeI (0.5 ml, 8.1 mmol) in a portion and the resulting mixture was stirred at 25° C. for 12 h. The reaction mixture was concentrated in vacuo, yielding a solid which was recrystallized from EtOH to yield 0.11 g (53%) of the desired product as white solid: mp 111–113° C.; Anal. Cal. For $C_{29}H_{31}N_3O_2S_2$. 1.0 HI requires C, 54.04; H, 4.89; N, 6.52. Found: C, 52.97; H, 5.01; N, 6.47.

Example 82

1-[1-(Naphthalene-1-sulfonyl)-piperidine-4-ylmethyl]-3-naphthalene-1-ylmethylurea 1-Naphthalene-1-ylmethyl-3-piperidine-4-ylmethylurea To a solution of 1-naphthalenemethylcyanate (1.1 g, 6.0 mmol) in 50 ml of CHCl₃ was added 4-aminomethylpiperidine (0.9 ml, 7.8 mmol) in a portion and the resulting solution was stirred at reflux for 12 h. The reaction mixture was concentrated in vacuo, yielding oily mixture which was purified on column chromatography (5% MeOH/CHCl₃) to yield the desired product 1.6 g (89%) of the desired product as an oil.

1-[1-(Naphthalene-1-sulfonyl)-piperidine-4-ylmethyl]-3-naphthalene-1-ylmethylurea To a solution of the amine (0.60 g, 2.0 mmol) in 30 ml of pyridine was added 1-naphthalenesulfonyl chloride (0.60 ml, 2.7 mmol) in a portion and the resulting mixture was stirred at 25° C. for 12 h. The reaction mixture was subjected to column chromatography (CHCl₃, neat) to yield 0.63 g (65%) of the desired product as light yellow solid, which was recrystallized from EtOAc to provide 0.37 g of the product as white solid: mp 103–104° C.; Anal. Cal. For $C_{28}H_{29}N_3O_3S$ requires C, 64.97; H, 5.99; N, 8.62. Found: C, 66.03; H, 5.83; N, 8.49.

Example 87

1-Naphthalene-1-ylmethyl-3-[1-(2-trifluoromethylbenzenesulfonyl)-pyrrolidin-3-yl]-urea

1-(Naphthalene-1-sulfonyl)-pyrrolidin-3-ylamine

To a solution of 1-naphthalenesulfonyl chloride (1.0 g, 5.4 mmol) in 50 ml of CH₂Cl₂ with 2 ml of trimethylamine was added 3-t-butoxycarbonylpyrrolidine (1.5 g, 6.5 mmol) in a portion and the resulting solution was stirred at reflux for 48 h. Reaction mixture was concentrated in vacuo, yielding oily mixture which was partioned between 100 ml of EtOAc and NaHCO₃ sat'd aqueous solution. Organic layer was separated, dried over Na₂SO₄ and concentrated in vacuo to provide an oil, which was redissolved in 20 ml of CH₂Cl₂. Toward this solution was added 1 ml of trifluoroacetic acid and the resulting solution was stirred for 2 h at 25° C. Reaction mixture was concentrated in vacuo, providing a brown oil, which was dissolved in EtOAc and washed with aqueous NaOH. organic layer was concentrated in vacuo to yield an oil which was subjected to column chromatography (30% MeOH/CHCl₃) to provide 0.17 g (23%) of the desired product.

1-Naphthalene-1-ylmethyl-3-[1-(2-trifluoromethyl-benzenesulfonyl)-pyrrolidin-3-yl]-urea The amine (37 mg, 0.12 mmol) and naphthalene-1-ylmethyl-carbamic acid 4-nitro-phenyl ester (61 mg, 0.19 mmol) in 5 ml of CH₂Cl₂ was stirred at 25° C. for 12 h . The reaction mixture was subjected to column chromatography (2% MeOH/CHCl₃) to yield 42 mg (74%) of the desired product as light yellow solid: mp 117–119° C.; Anal. Cal. For $C_{23}H_{22}F_3N_3O_3S$ requires C, 57.85; H, 4.64; N, 8.80. Found: C, 56.16; H, 4.71; N, 8.67.

Additional compounds may be synthesized by substitution of appropriate starting materials, and are not intended to be limited to those compounds shown in Table 3a.

Other compounds of Formula 1–4, as shown in Table 3 and Table 3a, were synthesized using the methods described above, using appropriately substituted starting materials.

TABLE 3

| No. | Ar | X | R₁ | L | K | W | mp | Analysis |
|---|---|---|---|---|---|---|---|---|
| 71 | 1-naphthyl | — | H | —(CH₂)₅— | CH₂NHCONH | 1-naphthyl | 105–06 | $C_{27}H_{29}N_3O_3S$ |
| 72 | 2-naphthyl | — | H | —(CH₂)₅— | CH₂NHCONH | 2-NO₂-phenyl | 115 | $C_{23}H_{26}N_4O_5S$ |
| 73 | 2-(hydroxymethyl)phenyl | — | H | —(CH₂)₅— | CH₂NHCONH | 1-naphthyl | Oil | $C_{24}H_{29}N_3O_4S$ + 0.5 CHCl₃ |
| 74 | 2-CF₃-phenyl | — | H | —(CH₂)₅— | CH₂NHCO | 1,2,3,4-tetrahydroquinolin-1-yl | Oil | $C_{23}H_{28}N_3O_3S$ |

TABLE 3a

| No. | Ar | X | L | K | W | mp | |
|---|---|---|---|---|---|---|---|
| 81 | 1-methylnaphthalene | — | 1-methyl-4-ethylpiperidine | S-methyl isothiourea (N-methyl, N'-ethyl) | 1-methylnaphthalene | 111–113 | $C_{29}H_{31}N_3O_2S$ + HI |
| 80 | 1-methylnaphthalene | — | 1-methyl-4-ethylpiperidine | N-methyl-N'-ethyl thiourea | 1-methylnaphthalene | 83–85 | $C_{28}H_{29}N_3O_2S_2$ |
| 82 | 1-methylnaphthalene | — | 1-methyl-4-ethylpiperidine | N-methyl-N'-ethyl urea | 1-methylnaphthalene | 104–106 | $C_{28}H_{29}N_3O_3S$ |
| 83 | 1-methylnaphthalene | — | 1-methyl-4-ethylpiperidine | N-methyl-N'-ethyl thiourea | methylenedioxyphenyl | 176–178 | $C_{25}H_{27}N_3O_4S_2$ |
| 84 | 2-methylnaphthalene | — | 1-methyl-4-ethylpiperidine | N-methyl-N'-ethyl thiourea | methylenedioxyphenyl | 199–201 | $C_{25}H_{27}N_3O_4S_2$ |
| 85 | 2-methyl-(trifluoromethyl)phenyl | — | 1-methyl-4-ethylpiperidine | N-methyl-N'-ethyl urea | 1-methylnaphthalene | 94–97 | $C_{25}H_{26}F_3N_3O_3S$ |
| 86 | 2-methyl-(trifluoromethyl)phenyl | — | 1-methyl-4-ethylpiperidine | N-methyl-N'-ethyl thiourea | 1-methylnaphthalene | 88–90 | $C_{25}H_{26}F_3N_3O_2S_2$ |
| 87 | 2-methyl-(trifluoromethyl)phenyl | — | 1-methyl-3-methylpyrrolidine | N-methyl-N'-ethyl urea | 1-methylnaphthalene | 117–119 | $C_{23}H_{22}F_3N_3O_3S$ |
| 88 | 2-methyl-nitrophenyl | — | 1-methyl-4-ethylpiperidine | N-methyl-N'-ethyl urea | 1-methylnaphthalene | 162–164 | $C_{24}H_{26}N_4O_5S$ |

Synthesis of compounds of Scheme 2

Compounds in which L is substituted may be produced according to Scheme 2. The carbobenzyloxy-protected amino acid derivative of L may be esterified by thionyl chloride and methanol as shown in Scheme 2, Step A, and the ester subsequently reduced by diisobutylaluminum hydride in THF as shown in Scheme 2, Step B, at −78° C., to yield alcohol, which is then oxidized by pyridinium chlorochromate in Scheme 2, Step C, in a suitable solvent such as $CH_2Cl_2$, to afford an aldehyde of Formula 2-1. The aldehyde may be treated with ammonia, and then trimethylsilylcyanide (Chakraborty, et al. Tet. Lett. 32(51):7597–7600, 1991) as shown in Scheme 2, Step D, in a suitable solvent such as methanol, to yield the compound of Formula 2-2. The compound of Formula 2-2 may be subjected to sulfonylation as described above in Scheme 1, Step A, to yield the compound of Formula 2-3. The cyano moiety of the compound of Formula 2-3 may be esterified and deblocked to afford compounds of Formula 2-4; or if desired, the compound of Formula 2-3 may be further reduced, or hydrolyzed as appropriate to yield substituted compounds other than those shown in Formula 2-5, which compounds may be further used in any of Steps C, D, E, or F of Scheme 1.

An example of the synthesis of a compound of Formula 2-5 is the synthesis of compound 79:

7-[Naphthalen-2-ylmethyl)-amino]-2-(2-nitrobenzenesulfonylamino)-heptanoic acid methyl ester (a) Step A, Scheme 2

6-Benzyloxycarbonylamino-hexanoic Acid Methyl Ester:

To a solution of 6-benzyloxycarbonylamino-hexanoic acid (10 g, 38 mmol) in methanol (200 mL) at room temperature was added thionyl chloride (11 g, 95 mmol). The reaction mixture was then refluxed for 16 h. The solvent was concentrated in vacuo, the residue was dissolved in ethyl acetate (200 mL) and washed with brine (3×150 mL), dried over anhydrous magnesium sulfate, and concentrated in vacuo. The residue was- purified by flash column chromatography (silica, 14% ethyl acetate in hexane) to afford the titled compound (6.2 g, 58%), a colorless liquid.

(b) Step B, Scheme 2

(6-Hydroxyhexyl)-carbamic acid benzyl ester:

To a solution of diisobutylaluminum hydride (49 mL, 1.5 M in toluene) in THF (150 mL) cooled to −78° C. was added a solution of 6-benzyloxycarbonylamino-hexanoic acid methyl ester (10 g, 37 mmol) in THF (100 mL). The reaction mixture was stirred for 4 h and methanol (2.5 mL) was added carefully at −78 to −75° C. After 2 h, the mixture was poured to 250 mL of 1 N HCl solution cooled in ice-bath, extracted with ethyl acetate (300 mL), washed with brine (3×100 mL), dried over anhydrous magnesium sulfate, and concentrated in vacuo. The residue was purified by flash column chromatography (silica, 50% ethyl acetate in hexane) to yield the titled compound (7.1 g, 80%); white solid, mp 67–68° C.

(c) Step C, Scheme 2

(6-Oxy-hexyl)-carbamic acid benzyl ester:

To a suspension of pyridinum chlorochromate (9.2 g, 43 mmol) and celite (37 g) in methylene chloride (400 mL) was added (6-hydroxyhexyl)-carbamic acid benzyl ester (7.1 g, 24 mmol). The mixture was stirred for 3 h and dry ethyl ether (500 mL) was added to it. The mixture was stirred for additional 0.5 h, filtered through a pad of celite and concentrated in vacuo. The residue was purified by flash column chromatography (silica, 10–25% ethyl acetate in hexane) to yield the titled compound (4.8 g, 79%); colorless light oil.

(d) Step D, Scheme 2

(6-Amino-6-cyano-hexyl)-carbamic acid benzyl ester:

Ammonia was bubbled through a stirred solution of (6-oxy-hexyl}-carbamic acid benzyl ester (6.0 g, 24 mmol) in methanol (200 mL) for 2 h and TMSCN (2.9 g, 28 mmol) was added dropwise. The reaction mixture was stirred for 24 h. The solvent was evaporated in vacuo. The residue was purified by flash column chromatography (silica, 90–100% ethyl acetate in hexane) to yield the titled compound (4.3 g, 65%); light yellow oil.

(e) (Step A, Scheme 1)

(6-Benzenesulfonylamino-6-cyano-hexyl) -carbamic acid benzyl ester:

Using the general procedure described in step A of scheme 1, (6-amino-6-cyano-hexyl}-carbamic acid benzyl ester (2.8 g, 10 mmol) was sulfonylated with 2-nitrobenzenesulfonyl chloride (2.5 g, 11 mmol) at 0° C. to yield the titled compound (1.7 g, 36%); yellow oil.

(f) Step E, Scheme 2

7-Amino-2 -nitrobenzenesulfonylamino-heptanoic acid methyl ester:

Dry HCl gas was bubbled to a stirred solution of (6-benzenesulfonylamino-6-cyano-hexyl}-carbamic acid benzyl ester (0.58 g, 1.3 mmol) in dry methanol (50 mL) for 2 h. The reaction mixture was cooled and solvent was evaporated in vacuo. Water (40 mL) was added to the reaction mixture and neutralized with 1 N NaOH to pH 9–10, extracted with ethyl acetate (4×100 mL), washed with brine (3×100 mL), dried over anhydrous magnesium sulfate, and concentrated in vacuo. The residue was purified by preparative TLC (silica, 10% ammonia (2.0 M in methanol) in chloroform) to yield the titled compound (0.047 g, 10%); yellow thick oil.

(g) (Steps C, D, E, F, Scheme 1)

7-[(Naphthalen-2-ylmethyl)-amino]-2-(2-nitrobenzenesulfonylamino)-heptanoic acid methyl ester:

Using the general procedure described in Steps C, D, E, and F of Scheme 1, 7-amino-2-nitrobenzenesulfonylamino-heptanoic acid methyl ester (0.060 g, 0.17 mmol) was reductively aminated with 2-naphthaldehyde (0.026 g, 0.017 mmol) to afford the titled compound (0.050 g, 60%); yellow oil.

Synthesis of compounds according to Scheme 3

Other compounds of the present invention may be synthesized according to Scheme 3. After protection of $H_2N$—L—COOH with Boc anhydride in $CH_2Cl_2$, as shown in Scheme 3, Step A, the protected amine may be amidated with W-K''' as in Scheme 3, Step B, where K''' is an alkylamino ester, using EDC and DMAP in a suitable solvent such as $CH_2Cl_2$, to yield compounds of Formula 3-1, where K''' and the carboxylic acid carbonyl of $H_2N$—L—COOH together form K. The compounds of Formula 3-1 may be deprotected using well known methods as shown in Scheme 3, Step C, and further sulfonylated with a sulfonyl halide of Ar, as shown in Scheme 3, Step D, in a suitable solvent such as $CH_2Cl_2$ and a tertiary amine such as triethylamine, to form the compound of Formula 3-2. The compounds of Formula 3-2 may be reduced to yield the compounds of Formula 3-3, as shown in Scheme 3, Step E, using borane-tetrahydorfuran (THF) complex, in THF, at elevated temperature in an inert atmosphere.

A specific example of such a synthesis using Scheme 3 is provided below for Example 75 from Table 4:

trans-3-(4-Chloro-phenyl)-2- ({[4-(naphthalene-1-sulfonylamino)-methyl]-cyclohexanecarbonyl}-amino]-propionic acid methyl ester:

(a) Step A, Scheme 3 trans-4 (tert-Butoxycarbonylamino-methyl)-cyclohexanecarboxylic acid:

To a solution of trans-4 -(aminomethyl) cyclohexanecarboxylic acid (10 g, 57 mmol) in 1 N NaOH (110 mL) cooled to 0° C. was added a solution of di-tert-butyl dicarbonate (15 g, 69 mmol) in dioxane (50 mL). The reaction mixture was stirred at 0° C. for 12 h. The raction mixture was neutralized by 1 N HCl solution to pH 3, extracted with ethyl ether (2×300 mL), washed with brine (2×300 mL), dried over anhydrous magnesium sulfate, and concentrated in vacuo to afford the titled compound (16 g, 100%); white solid, mp 128–9° C.

(b) Step B, Scheme 3

-trans-2-{[4-(tert-Butoxycarbonylamino-methyl)-cyclohexanecarbonyl]-amino}3-(4-Chloro-phenyl)-propionic acid methyl ester:

Using the general procedure described for the preparation Step D, Scheme 1, trans-4-(tert-butoxycarbonylamino-methyl)-cyclohexanecarboxylic acid (1.1 g, 4.0 mmol) was acylated with D,L-4-chlorophenylalanine methyl ester hydrochloride (1.0 g, 4.0 mmol) to afford the titled compound (1.9 g, 99%); white solid, mp 178–9° C.

(c) Step C, Scheme 3 trans-2-[4-(Aminomethyl-cyclohexanecarbonyl)-amino]3-(4-chloro-phenyl)-propionic acid methyl ester hydrochloride:

Using the general procedure described in step b scheme 1, trans-2-{[4-(tert-butoxycarbonylamino-methyl)-cyclohexanecarbonyl]-amino}3-(4-chloro-phenyl)-propionic acid methyl ester (1.8 g, 4.3 mmol) was deprotected using HCl in ethyl acetate to afford the titled compound; light yellow solid mp 146–9° C.

(d) Step D, Scheme 3 trans-3-(4-Chloro-phenyl)-2-({[4-(naphthalene-1-sulfonylamino)-methyl]-cyclohexanecarbonyl}-amino]-propionic acid methyl ester:

Using the general procedure described in example A scheme 1, trans-2-[4-(aminomethyl-cyclohexanecarbonyl)-amino] 3-(4-Chloro-phenyl)-propionic acid methyl ester hydrochloride (0.35 g, 0.86 mmol) was sulfonylated with 1-naphthalenesulfonyl chloride (0.42 g, 91%) to afford the titled ompound; white solid, mp 84–6° C.

The compound of Example 77, Table 4, was synthesized from the above compound by borane-THF reduction as follows:

(e) Step E, Scheme 3

Naphthalene-1-sulfonic Acid trans-(4-{[2-(4-Chloro-phenyl)-1-hydroxymethyl-ethylamino]-methyl}-cyclohexylmetbyl)-amide:

Using the general procedure described in Step H, Scheme 1, trans-3-(4-chloro-phenyl)-2-({[4-(naphthalene-1-sulfonylamino)-methyl]-cyclohexanecarbonyl}-amino]-propionic acid methyl ester (0.30 g, 0.55 mmol) was reduced by borane:THF complex (1.0 M in THF) to afford the titled compound; colorless oil.

Other compounds of Formula 3-3 or Formula 3-4, as shown in Table 4, where for example, K is substituted with an alcohol or ester, may also be synthesized using the methods of Scheme 3.

TABLE 4

| No. | Ar | X | $R_1$ | L | K | W | mp | Analysis |
|---|---|---|---|---|---|---|---|---|
| 75 | naphthalen-1-yl | — | H | trans-cyclohexyl | $CO_2CH_3$ / CONHCHCH$_2$ | 4-Cl-phenyl | 84–6 | $C_{28}H_{31}N_2O_5SCl$ + 0.4 $CHCl_3$ |
| 76 | 2-methyl-nitrobenzene ($NO_2$) | — | H | trans-cyclohexyl | $CO_2CH_3$ / CONHCHCH$_2$ | 4-Cl-phenyl | Oil | $C_{24}H_{28}N_3O_7SCl$ + 0.15 $CHCl_3$ |
| 77 | naphthalen-1-yl | — | H | trans-cyclohexyl | $CH_2OH$ / $CH_2NHCHCH_2$ | 4-Cl-phenyl | 223–3 | $C_{27}H_{33}N_2O_3SCl$ + HCl |

TABLE 4-continued

| No. | Ar | X | $R_1$ | L | K | W | mp | Analysis |
|---|---|---|---|---|---|---|---|---|
| 78 | (2-naphthyl) | — | H | (cyclohexyl, trans with ethyl) | $\underset{CH_2NHCHCH_2}{CH_2OH}$ | (4-chlorophenyl, methyl-substituted) | 263–4 | $C_{27}H_{33}N_2O_3SCl$ + HCl |

Synthesis of compounds 89 and 90

The synthesis of compounds such as 89 and 90 may be accomplished by the method shown in Scheme 4, as described below:

Example 89

(a) 4-Oxo-1,2,3,4-tetrahydronaphthalene-1-carboxylic acid-(naphthalene-1-ylmethyl) -amide (Scheme 4, product 1)

A mixture of 1-naphthalenemethylamine (1.37 g, 7.2 mmol), 4-oxo-1,2,3,4-tetrahydronaphthalene-1-carboxylic acid (1.13 g, 7.2 mmol) ECD (2.87 g, 15 mmol), and DMAP (1.83 g, 15 mmol) in $CH_2Cl_2$ (20 mL) was stirred at room temperature. After 12 h, the reaction mixture was concentrated and the residue was purified by flash column chromatography (2–5% MeOH in $CH_3Cl$ to yield the product (2.29 g, 97% liht yellow solid, m.p. 155–156° C.).

(b) 4-Cyano-4-trimethylsilanyloxy-1,2,3,4-tetrahydronaphthalene-1-carboxylic acid-(naphthalen-1-ylmethyl)-amide (Scheme 4, product 2)

To a mixture of the product of step (a) (2.29 g, 6.95 mmol) and a catalytic amount of $ZnI_2$ in dry $CH_2Cl_2$ (50 mL) at 0° C. was added dropwise TMSCN (1.4 g, 1.87 mL, 14 mmol) under argon. The reaction mixture was warmed to room temperature and stirred for 24 h. After concentration of the reaction mixture, the residue was purified by flash column chromatography (2–5% MeOH in $CH_3Cl$ to yield the product (1.6 g, 54%, 95% after recovering the product from (a); light yellow solid, m.p. 55–56° C.).

(c) 1-Aminomethyl-4-{[(naphthalene-1-ylmethyl)-amino]-methyl}-1,2,3,4-tetrahydronaphthalen-1-ol (Scheme 4, product 3)

To a solution of the product of step (b) (1.4 g, 3.27 mmol) in THF (30 mL) was added dropwise 25 mL of $BH_3$-THF complex (1.0 M in THF) under argon. The reaction mixture was refluxed for 16 h. After cooling to 0° C., 6N HCl was added dropwise to the reaction mixture and the resultant mixture stirred for 24 h at room temperature. After cooling to 0° C., this mixture was neutralized by 1N NaOH to pH 7 to 8, extracted with ethyl acetate (100 mL), washed with water (60 mL×2), dried ($Na_2SO_4$), and concentrated. The residue was purified by flash column chromatography (2–5% MeOH in $CH_3Cl$ to yield the product (0.30 g, 27%, light yellow solid).

(d) N-(1-hydroxy-4-{[(naphthalen-1-ylmethyl)-amino]-methyl}-1,2,3,4-tetrahydronaphthalen-1-ylmethyl-2-nitro-benzenesulfonamide (Scheme 4, product 4)

To a mixture of the product of step (c) (0.30 g, 0.866 mmol) and Et3N (0.35 g, 3.46 mmol) in dry $CH_2Cl_2$ (15 mL) at 0° C. was added dropwise a solution of 2-nitrobenzenesulfonyl chloride (0.19 g, 0.866 mmol) in dry $CH_2Cl_2$ (10 mL). The reaction mixture was warmed to room temperature and stirred for 6 h. After concentration of the reaction mixture, the residue was purified by flash column chromatography (2–5% MeOH in $CH_3Cl$) to yield the product (0.43 g, 93%, light yellow solid.

Example 90

Scheme 4, product 5)

A mixture of the compound of Example 89 (0.35 g, 0.658 mmol) and TsOH (0.075 g, 0.395 mmol) in toluene was refluxed for 0.5 h. The reaction mixture was concentrated and purified by TLC chromatography (10% MeOH in $CH_3Cl$) to yield the product (0.217 g, 64%, light yellow solid, m.p. 53–54° C.).

Pharmacological Evaluation of Compounds at Cloned Human Neuropeptide Y-type Receptors.

The pharmacologic properties of the compounds of the present invention were evaluated at the cloned human neuropeptide Y-type receptors Y1, Y2, Y4, and Y5, or in in vivo studies in rats, using the protocols described below.

MATERIALS AND METHODS

Cell Culture

COS-7 cells were grown on 150 mm plates in D-MEM with supplements (Dulbecco's Modified Eagle Medium with 10% bovine calf serum, 4 mM glutamine, 100 units/ml penicillin/100 μg/ml streptomycin) at 37° C., 5% $CO_2$. Stock plates of COS-7 cells were trypsinized and split 1:6 every 3–4 days. Human embryonic kidney 293 cells were grown on 150 mm plates in D-MEM with supplements (minimal essential medium) with Hanks' salts and supplements (Dulbecco's Modified Eagle Medium with 10% bovine calf serum, 4 mM glutamine, 100 units/ml penicillin/100 μg/ml streptomycin) at 37° C., 5% $CO_2$. Stock plates of 293 cells were trypsinized and split 1:6 every 3–4 days. Mouse fibroblast LM(tk-) cells were grown on 150 mm plates in D-MEM with supplements (Dulbecco's Modified Eagle Medium with 10% bovine calf serum, 4 mM glutamine, 100 units/mL penicillin/100 μg/mL streptomycin) at 37° C., 5% $CO_2$. Stock plates of LM(tk-) cells were trypsinized and split 1:10 every 3–4 days.

LM(tk-) cells stably transfected with the human Y5 receptor were routinely converted from an adherent monolayer to a viable suspension. Adherent cells were harvested with trypsin at the point of confluence, resuspended in a minimal volume of complete DMEM for a cell count, and further diluted to a concentration of $10^6$ cells/ml in suspension media (10% bovine calf serum, 10% 10x Medium 199 (Gibco), 9 mM $NaHCO_3$, 25. mM glucose, 2 mM L-glutamine, 100 units/ml penicillin/100 μg/mi streptomycin, and 0.05% methyl cellulose). The cell suspension was maintained in a shaking incubator at 37° C., 5% $CO_2$ for 24 hours. Membranes harvested from cells grown in this manner may be stored as large, uniform batches in liquid nitrogen. Alternatively, cells may be returned to adherent cell culture in complete DMEM by distribution into 96-well microtiter plates coated with poly-D-lysine (0.01 mg/ml) followed by incubation at 37° C., 5% $CO_2$ for 24 hours. Cells prepared in this manner yielded a robust and reliable NPY-dependent response in cAMP radio-immunoassays as further described hereinbelow.

Mouse embryonic fibroblast NIH-3T3 cells were grown on 150 mm plates in Dulbecco's Modified Eagle Medium (DMEM) with supplements (10 bovine calf serum, 4 mM glutamine, 100 units/ml penicillin/100 µg/ml streptomycin) at 37° C., 5% $CO_2$. Stock plates of NIH-3T3 cells were trypsinized and split 1:15 every 3–4 days.

Sf9 and Sf21 cells were grown in monolayers on 150 mm tissue culture dishes in TMN-FH media supplemented with 10% fetal calf serum, at 27° C., no $CO_2$. High Five insect cells were grown on 150 mm tissue culture dishes in Ex-Cell 400™ medium supplemented with L-Glutamine, also at 27° C., no $CO_2$.

Transient Transfection

All receptor subtypes studied (human and rat Y1, human and rat Y2, human and rat Y4, human and rat Y5) were transiently transfected into COS-7 cells by the DEAE-dextran method, using 1 µg of DNA /$10^6$ cells (Cullen, 1987). The human Y1 receptor was prepared using known methods (Larhammar, et al., 1992).

Stable Transfection

Human Y1, human Y2, and rat Y5 receptors were co-transfected with a G-418 resistant gene into the human embryonic kidney 293 cell line by a calcium phosphate transfection method (Cullen, 1987). Stably transfected cells were selected with G-418. Human Y4 and human Y5 receptors were similarly transfected into mouse fibroblast LM(tk-) cells and NIH-3T3 cells.

Binding of the compounds of the present invention to the human Y1, Y2, Y4 and Y5 receptors was evaluated using stably transfected 293 or LM(tk-) cells as described above. Stably transfected cell lines which may be used for binding assays include, for example, for the human Y1 receptor, 293-hY1-5 (deposited Jun. 4, 1996, under ATCC Accession No. CRL-12121), for the human Y2 receptor, 293-hY2-10 (deposited Jan. 27, 1994, under ATCC Accession No. CRL-11537), for the human Y4 receptor, L-hY4-3 (deposited Jan. 11, 1995, under ATCC Accession No. CRL-11779), and for the human Y5 receptor, L-hY5-7 (deposited Nov. 15, 1995, under ATCC Accession No. CRL-11995).

Expression of other G-protein coupled receptors $\alpha_1$ Human Adrenergic Receptors:

To determine the binding of compounds to human $\alpha_1$ receptors, LM(tk-) cell lines stably transfected with the genes encoding the $\alpha_{1a}$, $\alpha_{1b}$, and $\alpha_{1d}$ receptors were used. The nomenclature describing the $\alpha_1$ receptors was changed recently, such that the receptor formerly designated $\alpha_{1a}$ is now designated $\alpha_{1d}$, and the receptor formerly designated $\alpha_{1c}$ is now designated $\alpha_{1a}$ (ref). The cell lines expressing these receptors were deposited with the ATCC before the nomenclature change and reflect the subtype desgnations formerly assigned to these receptors Thus, the cell line expressing the receptor described herein as the $\alpha_{1a}$ receptor was deposited with the ATCC on Sep. 25, 1992, under ATCC Accession No. CRL 11140 with the designation L-$\alpha_{1c}$. The cell line expressing receptor described herein as the $\alpha_{1d}$ receptor was deposited with the ATCC on Sep. 25, 1992, under ATCC Accession No. CRL 11138 with the designation L-$\alpha_{1A}$. The cell line expressing the $\alpha_{1b}$ receptor is designated L-$\alpha_{1B}$, and was deposited on Sep. 25, 1992, under ATCC Accession No. CRL 11139.

$\alpha_2$ Human Adrenergic Receptors:

To determine the binding of compounds to human $\alpha_2$ receptors, LM(tk-) cell lines stably transfected with the genes encoding the $\alpha_{2A}$, $\alpha_{2B}$, and $\alpha_2$C receptors were used. The cell line expressing the $\alpha_{2A}$ receptor is designated L-$\alpha_{2A}$, and was deposited on Nov. 6, 1992, under ATCC Accession No. CRL 11180. The cell line expressing the $\alpha_{2B}$ receptor is designated L-NGC-$\alpha_{2B}$, and was deposited on Oct. 25, 1989, under ATCC Accession No. CRL 10275. The cell line expressing the $\alpha_{2C}$ receptor is designated L and was deposited on Nov. 6, 1992, under ATCC Accession No. CRL-11181. Cell lysates were prepared as described below (see Radioligand Binding to Membrane Suspensions), and suspended in 25 mM glycylglycine buffer (pH 7.6 at room temperature). Equilibrium competition binding assay were performed using [$^3$H]rauwolscine (0.5 nM), and nonspecific binding was determined by incubation with 10 µM phentolamine. The bound radioligand was separated by filtration through GF/B filters using a cell harvester.

Human Histamine $H_1$ Receptor:

The coding sequence of the human histamine $H_1$ receptor, homologous to the bovine $H_1$ receptor, was obtained from a human hippocampal cDNA library, and was cloned into the eukaryotic expression vector pCEXV-3. The plasmid DNA for the $H_1$ receptor is designated pcEXV-H1, and was deposited on Nov. 6, 1992, under ATCC Accession No. 75346. This construct was transfected into COS-7 cells by the DEAE-dextran method. Cells were harvested after 72 hours and lysed by sonication in 5 mM Tris-HCl, 5 mM EDTA, pH 7.5. The cell lysates were centrifuged at 1000 rpm for 5 min at 4° C., and the supernatant was centrifuged at 30,000×g for 20 min. at 4° C. The pellet was suspended in 37.8 mM $NaHPO_4$, 12.2 mM $KH_2PO_4$, pH 7.5. The binding of the histamine $H_1$ antagonist [$^3$H]mepyramine (1 nM, specific activity: 24.8 Ci/mM) was done in a final volume of 0.25 mL and incubated at room temperature for 60 min. Nonspecific binding was determined in the presence of 10 AM mepyramine. The bound radioligand was separated by filtration through GF/B filters using a cell harvester.

Human Histamine $H_2$ Receptor:

The coding sequence of the human $H_2$ receptor was obtained from a human placenta genomic library, and cloned into the cloning site of PCEXV-3 eukaryotic expression vector. The plasmid DNA for the $H_2$ receptor is designated pcEXV-H2, and was deposited on Nov. 6, 1992 under ATCC Accession No. 75345. This construct was transfected into COS-7 cells by the DEAE-dextran method: Cells were harvested after 72 hours and lysed by sonication in 5 mM Tris-HCl, 5 mM EDTA, pH 7.5. The cell lysates were centrifuged at 1000 rpm for 5 min at 4° C., and the supernatant was centrifuged at 30,000×g for 20 min at 4° C. The pellet was suspended in 37.8 mM $NaHPO_4$, 12.2 mM $K2PO_4$, pH 7.5. The binding of the histamine $H_2$ antagonist [$^3$H]tiotidine (5 nM, specific activity: 70 Ci/mM) was done in a final volume of 0.25 ml and incubated at room temperature for 60 min. Nonspecific binding was determined in the presence of 10 µM histamine. The bound radioligand was separated by filtration through GF/B filters using a cell harvester.

Human Serotonin Receptors:

$5HT_{1D\alpha}$, $5HT_{1D\beta}$, $5HT_{1E}$, $5HT_{1F}$ Receptors: LM(tk-) clonal cell lines stably transfected with the genes encoding each of these 5HT receptor subtypes were prepared as described above. The cell line for the $5HT_{1D\alpha}$ receptor, designated as Ltk-8-30-84, was deposited on Apr. 17, 1990, and accorded ATCC Accession No. CRL 10421. The cell for the $5HT_{1D\beta}$ receptor, designated as Ltk-11, was deposited on Apr. 17, 1990, and accorded ATCC Accession No. CRL 10422. The cell line for the $5HT_{1E}$ receptor, designated 5 $HT_{1E}$-7, was deposited on Nov. 6, 1991, and accorded ATCC Accession No. CRL 10913. The cell line for the $5HT_{1F}$ receptor, designated L-5-$HT_{1F}$, was deposited on Dec. 27, 1991, and accorded ATCC Accession No. ATCC 10957. Membrane preparations comprising these receptors were prepared as described below, and suspended in 50 mM Tris-HCl buffer (pH 7.4 at 37° C.) containing 10 mM $MgCl_2$, 0.2 mM EDTA, 10 M pargyline, and 0.1% ascorbate. The binding of compounds was determined in competition binding assays by incubation for 30 minutes at 37° C. in the presence of 5 nM [$^3$H]serotonin. Nonspecific binding was determined in the presence of 10 μM serotonin. The bound radioligand was separated by filtration through GF/B filters using a cell harvester.

Human $5HT_2$ Receptor:

The coding sequence of the human $5HT_2$ receptor was obtained from a human brain cortex cDNA library, and cloned into the cloning site of pCEXV-3 eukaryotic expression vector. This construct was transfected into COS-7 cells by the DEAE-dextran method. Cells were harvested after 72 hours and lysed by sonication in 5 mM Tris-HCl, 5 mM EDTA, pH 7.5. This cell line was deposited with the ATCC on Oct. 31, 1989, designated as L-NGC-$5HT_2$, and was accorded ATCC Accession No. CRL 10287. The cell lysates were centrifuged at 1000 rpm for 5 minutes at 4° C., and the supernatant was centrifuged at 30,000×g for 20 minutes at 4° C. The pellet was suspended in 50 mM Tris-HCl buffer (pH 7.7 at room temperature) containing 10 mM $MgSO_4$, 0.5 mM EDTA, and 0.1% ascorbate. The potency of alpha-1 antagonists at $5HT_2$ receptors was determined in equilibrium competition binding assays using [3H]ketanserin (1 nM). Nonspecific binding was defined by the addition of 10 μM mianserin. The bound radioligand was separated by filtration through GF/B filters using a cell harvester.

Human 5-HT, Receptor:

A LM(tk-) clonal cell line stably transfected with the gene encoding the $5HT_7$ receptor subtype was prepared as described above. The cell line for the $5HT_7$ receptor, designated as L-$5HT_{4B}$, was deposited on Oct. 20, 1992, and accorded ATCC Accession No. CRL 11166.

Human Dopamine $D_3$ Receptor:

The binding of compounds to the human D3 receptor was determined using membrane preparations from COS-7 cells transfected with the gene encoding the human $D_3$ receptor. The human dopamine $D_3$ receptor was prepared according to known methods (Sokoloff, P. et al. Nature, 347, 146, 1990, deposited with the EMBL Genbank as X53944). Cells were harvested after 72 hours and lysed by sonication in 5 mM Tris-HCl, 5 mM EDTA, pH 7.5. The cell lysates were centrifuged at 1000 rpm for 5 minutes at 4° C., and the supernatant was centrifuged at 30,000×g for 20 minutes at 4° C. The pellet was suspended in 50 mM Tris-HCl (pH 7.4) containing 1 mM EDTA, 5 mM KCl, 1.5 mM $CaCl_2$, 4 mM $MgCl_2$, and 0.1% ascorbic acid. The cell lysates were incubated with [$^3$H]spiperone (2 nM), using 10 μM (+)Butaclamol to determine nonspecific binding.

Membrane Harvest

Membranes were harvested from COS-7 cells 48 hours after transient transfection. Adherent cells were washed twice in ice-cold phosphate buffered saline (138 mM NaCl, 8.1 mM $Na_2HPO_4$, 2.5 mM KCl, 1.2 mM $KH_2PO_4$, 0.9 mM $CaCl_2$, 0.5 mM $MgCl_2$, pH 7.4) and lysed by sonication in ice-cold sonication buffer (20 mM Tris-HCl, 5 mM EDTA, pH 7.7). Large particles and debris were cleared by low speed centrifugation (200×g, 5 min, 4° C.). Membranes were collected from the supernatant fraction by centrifugation (32,000×g, 18 min, 4° C.), washed with ice-cold hypotonic buffer, and collected again by centrifugation (32,000×g, 18 min, 4° C.). The final membrane pellet was resuspended by sonication into a small volume of ice-cold binding buffer (~1 ml for every 5 plates: 10 mM NaCl, 20 mM HEPES, 0.22 mM $KH_2PO_4$, 1.26 mM $CaCl_2$, 0.81 mM $MgSO_4$, pH 7.4). Protein concentration was measured by the Bradford method (Bradford, 1976) using Bio-Rad Reagent, with bovine serum albumin as a standard. Membranes were held on ice for up to one hour and used fresh, or flash-frozen and stored in liquid nitrogen.

Membranes were prepared similarly from 293, LM(tk-), and NIH-3T3 cells. To prepare membranes from baculovirus infected cells, $2\times10^7$ Sf21 cells were grown in 150 mm tissue culture dishes and infected with a high-titer stock of hY5BB3. Cells were incubated for 2–4 days at 27° C., no $CO_2$ before harvesting and membrane preparation as described above.

Membranes were prepared similarly from dissected rat hypothalamus. Frozen hypothalami were homogenized for 20 seconds in ice-cold sonication buffer with the narrow probe of a Virtishear homogenizer at 1000 rpm (Virtis, Gardiner, N.Y.). Large particles and debris were cleared by centrifugation (200×g, 5 min, 4° C.) and the supernatant fraction was reserved on ice. Membranes were further extracted from the pellet by repeating the homogenization and centrifugation procedure two more times. The supernatant fractions were pooled and subjected to high speed centrifugation (100,000×g, 20 min. 4° C.). The final membrane pellet was resuspended by gentle homogenization into a small volume of ice-cold binding buffer (1 mL/ gram wet weight tissue) and held on ice for up to one hour, or flash-frozen and stored in liquid nitrogen.

Radioligand Binding to Membrane Suspensions

Membrane suspensions were diluted in binding buffer supplemented with 0.1% bovine serum albumin to yield an optimal membrane protein concentration so that $^{125}$I-PYY (or alternative radioligand such as $^{125}$I-NPY, $^{125}$I-$PYY_{3.36}$, or $^{125}$I [Leu$^{31}$Pro$^{34}$]PYY) bound by membranes in the assay was less than 10% of $^{125}$I-PYY (or alternative radioligand) delivered to the sample (100,000 dpm/sample=0.08 nM for competition binding assays). $^{125}$I-PYY (or alternative radioligand) and peptide competitors were also diluted to desired concentrations in supplemented binding buffer. Individual samples were then prepared in 96-well polypropylene microtiter plates by mixing $^{125}$I-PYY (25 μL) (or alternative radioligand), competing peptides or supplemented binding buffer (25 μL), and finally, membrane suspensions (200 μl). Samples were incubated in a 30° C. water bath with constant shaking for 120 min. Incubations were terminated by filtration over Whatman GF/C filters (pre-coated with 1% polyethyleneimine and air-dried before use), followed by washing with 5 mL of ice-cold binding buffer. Filter-trapped membranes were impregnated with MultiLex solid scintillant (Wallac, Turku, Finland) and counted for $^{125}$I in a Wallac Beta-Plate Reader. Non-specific binding was defined by 300 nM human NPY for all receptors except the Y4 subtypes; 100 nM human PP was used for the human Y4 and 100 nM rat PP for the rat Y4. Specific binding in time course and competition studies was typically 80%; most nonspecific binding was associated with the filter. Binding data were analyzed using nonlinear regression and statistical techniques available in the GraphPAD Prism package (San Diego, Calif.).

Functional Assay: Radioimmunoassay of cAMP

Stably transfected cells were seeded into 96-well microtiter plates and cultured until confluent. To reduce the potential for receptor desensitization, the serum component of the media was reduced to 1.5% for 4 to 16 hours before the assay. Cells were washed in Hank's buffered saline, or HBS (150 mM NaCl, 20 mM HEPES, 1 mM $CaCl_2$, 5 mM KCl, 1 mM $MgCl_2$, and 10 mM glucose) supplemented with 0.1 bovine serum albumin plus 5 mM theophylline and pre-equilibrated in the same solution for 20 min at 37° C. in 5% $CO_2$. Cells were then incubated 5 min with 10 μM forskolin and various concentrations of receptor-selective ligands. The assay was terminated by the removal of HBS and acidification of the cells with 100 mM HCl. Intracellular cAMP was extracted and quantified with a modified version of a magnetic bead-based radioimmunoassay (Advanced Magnetics, Cambridge, Mass.). The final antigen/antibody complex was separated from free $^{125}$I-cAMP by vacuum filtration through a PVDF filter in a microtiter plate (Millipore, Bedford, Mass.). Filters were punched and counted for $^{125}$I in a Packard gamma counter. Binding data were analyzed using nonlinear regression and statistical techniques available in the GraphPAD Prism package (San Diego, Calif.).

Functional Assay: Intracellular calcium mobilization

The intracellular free calcium concentration was measured by microspectroflourometry using the fluorescent indicator dye Fura-2/AM (ref)- Stably transfected cells were seeded onto a 35 mm culture dish containing a glass coverslip insert. Cells were washed with HBS and loaded with 100 μl of Fura-2/AM (10 μM) for 20 to 40 min. After washing with HBS to remove the Fura-2/AM solution, cells were equilibrated in HBS for 10 to 20 min. Cells were then visualized under the 40x objective of a Leitz Fluovert FS microscope and fluorescence emission was determined at 510 nM with excitation wave lengths alternating between 340 nM and 380 nM. Raw fluorescence data were converted to calcium concentrations using standard calcium concentration curves and software analysis techniques.

In vivo STUDIES IN RATS

Food intake in satiated rats

For these determinations food intake maybe measured in normal satiated rats after intracerebroventricular application (i.c.v.) of NPY in the presence or absence of the test compound. Male Sprague Dawley rats ciba-Geigy AG, Sisseln, Switzerland weighing between 180 g and 220 g are used for all experiments. The rats are individually housed in stainless steel cages and maintained on an 11:13 h light-dark cycle (lights off at 18:00 h) at a controlled temperature of 21–23° C. at all times. Water and food (NAFAG lab chow pellets, NAFAG, Gossau, Switzerland) are available ad libidum.

Rats under pentobarbital anesthesia are stereotaxically implanted with a stainless steel guide cannula targeted at the right lateral ventricle. Stereotaxic coordinates, with the incisor bar set −2.0 mm below interaural line, are: −0.8 mm anterior and +1.3 mm lateral to bregma. The guide cannula is placed on the dura. Injection cannulas extend the guide cannulas −3.8 mm ventrally to the skull surface. Animals are allowed at least 4 days of recovery postoperatively before being used in the experiments. Cannula placement is checked postoperatively by testing all rats for their drinking response to a 50 ng intracerebroventricular (i.c.v.) injection of angiotensin II. Only rats which drink at least 2.5 ml of water within 30 min. after angiotensin II injection are used in the feeding studies.

All injections are made in the morning 2 hours after light onset. Peptides are injected in artificial cerebrospinal fluid (ACSF) in a volume of 5 μl. ACSF contains: NaCl 124 mM, KCl 3.75 mM, $CaCl_2$ 2.5 mM, $MgSO_4$ 2.0 mM, $KH_2PO_4$ 0.22 mM, $NaHCO_3$ 26 mM and glucose 10 mM. porcine-NPY is dissolved in artificial cerebrospinal fluid (ACS). For i.c.v. injection the test compounds are preferably dissolved in DMSO/water (10%, v/v). The vehicle used for intraperitoneal (i.p.), subcutaneous (s.c.) or oral (p.o.) delivery of compounds is preferably water, physiological saline or DMSO/water (10% v/v), or cremophor/water (20% v/v), respectively.

Animals which are treated with both test compounds and p-NPY are treated first with the test compound. Then, 10 min. after i.c.v. application of the test compound or vehicle (control), or 30–60 min after i.p., s.c. and p.o. application of the test compound or vehicle, 300 pmol of NPY is administered by intracerebroventricular (i.c.v.) application.

Food intake may be measured by placing preweighed pellets into the cages at the time of NPY injection. Pellets are removed from the cage subsequently at each selected time point and replaced with a new set of preweighed pellets. The food intake of animals treated with test compound may be calculated as a percentage of the food intake of control animals, i.e., animals treated with vehicle. Alternatively, food intake for a group of animals subjected to the same experimental condition may be expressed as the mean ±S.E.M. Statistical analysis is performed by analysis of variance using the Student-Newman-Keuls test.

Food intake in food-deprived rats

Food-deprivation experiments are conducted with male Sprague-Dawley rats weighing between 220 and 250 g. After receipt, the animals are individually housed for the duration of the study and allowed free access to normal food together with tap water. The animals are maintained in a room with a 12 h light/dark cycle (8:00 a.m. to 8:00 p.m. light) at 24° C. and monitored humidity. After placement into individual cages the rats undergo a 4 day equilibration period, during which they are habituated to their new environment and to eating a powdered or pellet diet (NAFAG, Gossau, Switzerland).

At the end of the equilibration period, food is removed from the animals for 24 hours starting at 8:00 a.m. At the end of the fasting period compound or vehicle may be administered to the animals orally or by injection intraperitoneally or intravenously. After 10–60 min. food is returned to the animals and their food intake monitored at various time periods during the following 24 hour period. The food intake of animals treated with test compound may be calculated as a percentage of the food intake of control animals (i.e., animals treated with vehicle). Alternatively, food intake for a group of animals subjected to the same experimental conditions may be expressed as the mean ±S.E.M.

Food intake in obese Zucker rats

The antiobesity efficacy of the compounds according to the present invention might also be manifested in Zucker obese rats, which are known in the as an animal model of obesity. These studies are conducted with male Zucker fatty rats (fa/fa Harlan CPB, Austerlitz NL) weighing between 480 g and 500 g. Animals are individually housed in metabolism cages for the duration of the study and allowed free access to normal powdered food and water. The animals are maintained in a room with a 12 h light/dark cycle (light from 8:00 A.M. to 8:00 P.M.) at 24° C. and monitored humidity. After placement into the metabolism cages the rats undergo a 6 day equilibration period, during which they are habituated to their new environment and to eating a powdered diet. At the end of the equilibration period, food intake during the light and dark phases is determined. After a 3 day control period, the animals are treated with test compounds or vehicle (preferablywater or physiological saline or DMSO/water (10%,v/v) or cremophor/water (20%,v/v). Food intake is then monitored over the following 3 day period to determine the effect of administration of test compound or vehicle alone. As in the studies described hereinabove, food intake in the presence of drug may be expressed as a percentage of the food intake of animals treated with vehicle.

Materials

Cell culture media and supplements were from Specialty Media (Lavallette, N.J.). Cell culture plates (150 mm and 96-well microtiter) were from Corning (Corning, N.Y.). Sf9, Sf21, and High Five insect cells, as well as the baculovirus transfer plasmid, pBlueBacIII™, were purchased from Invitrogen (San Diego, Calif.). TMN-FH insect medium complemented with 10% fetal calf serum, and the baculovirus DNA, BaculoGold™, was obtained from Pharmingen (San Diego, Calif.). Ex-Cell 400™ medium with L-Glutamine was purchased from JRH Scientific. Polypropylene 96-well microtiter plates were from Co-star (Cambridge, Mass.). All radioligands were from New England Nuclear (Boston, Mass.). Commercially available NPY and related peptide analogs were either from Bachem California (Torrance, Calif.) or Peninsula (Belmont, Calif.); [D-Trp$^{32}$]NPY and PP C-terminal fragments were synthesized by custom order from Chiron Mimotopes Peptide Systems (San Diego, Calif.). Bio-Rad Reagent was from Bio-Rad (Hercules, Calif.). Bovine serum albumin (ultra-fat free, A-7511) was from Sigma (St. Louis. Mo.). All other materials were reagent grade.

EXPERIMENTAL RESULTS

Applicants have synthesized and evaluated the binding and functional properties of several compounds at the cloned human Y1, human Y2, human Y4, and human Y5 receptors. As shown below in Table 5, applicants have discovered several compounds which not only bind selectively to the human Y5 receptor but also act as Y5 receptor antagonists, as measured by their ability to block NPY-induced inhibition of cAMP accumulation in forskolin-stimulated LM(tk-) cells stably transfected with the cloned human Y5 receptor.

Table 5:

Evaluation of human Y5 receptor antagonists

The ability of the compounds to antagonize the Y-type receptors is reported as the $K_b$. The $K_b$ is derived from the $EC_{50}$, or concentration of half-maximal effect, in the presence ($EC_{50}$) or absence ($EC_{50}'$) of compound, according to the equation: $K_b=[NPY]/((EC_{50}/EC_{50}')-1)$. Results shown are representative of at least three indepenent experiments.

N.D.=Not determined.

TABLE 5

| Example | Binding Affinity ($K_i$ (nM) vs. $^{125}$I-PYY) Human Receptor | | | | $K_b$ (nM) |
|---|---|---|---|---|---|
| | Y1 | Y2 | Y4 | Y5 | |
| 31 | 5550 | 1000 | 8020 | 14 | 6.0 |
| 32 | 3550 | 955 | 11700 | 11 | 23 |
| 36 | 16000 | 7760 | 20400 | 8.3 | 26 |
| 38 | 13000 | 1610 | 18500 | 9.8 | 16 |
| 40 | 17200 | 7570 | 27500 | 11 | 3.0 |
| 37 | 14500 | 617 | 21500 | 26 | 38 |
| 77 | 3240 | 851 | 13100 | 17 | 311 |
| 44 | 23700 | 58200 | 19300 | 14 | 50 |
| 45 | 48700 | 5280 | 63100 | 28 | 49 |

Several of the compounds were further tested using in vivo animal models of feeding behavior. Since NPY is the strongest known stimulant of feeding behavior, experiments were performed with several compounds to evaluate the effect of the compounds described above on NPY-induced feeding behavior in satiated rats.

First, 300 pmole of porcine NPY in vehicle (A.C.S.F.) was administered by intracerebroventricular (i.c.v.) injection, along with i.p. administration of compound vehicle (10% DMSO/water), and the food intake of NPY-stimulated animals was compared to food intake in animals treated with the vehicles. The 300 pmole injection of NPY was found to significantly induce food intake (p<0.05; Student-Newman-Keuls).

Using the 300 pmole dose of NPY found to be effective to stimulate feeding, other animals were treated with the compounds by intraperitoneal (i.p.) administration, followed 30–60 minutes later by i.c.v. NPY administration, and measurement of subsequent food intake. As shown in Table 6, NPY-induced food intake was significantly reduced in animals first treated with the compounds (p<0.05; Student-Newman-Keuls). These experiments demonstrate that NPY-induced food intake is significantly reduced by administration to animals of a compound which is a Y5-selective antagonist.

Table 6. NPY-induced cumulative food intake in rats treated with either the i.c.v. and i.p. vehicles (control), 300 pmole NPY alone (NPY), or in rats treated first with compound and then NPY (NPY+compound). Food intake was measured 4 hours after stimulation with NPY. Food intake is reported as the mean ±S.E.M. intake for a group of animals.

TABLE 6

| Example | 31 | 32 |
|---|---|---|
| Compound Dose (mg/kg i.p.) | 10 | 30 |
| control (vehicles only) | 2.4 ± 0.7 | 2.9 ± 0.8 |
| NPY | 5.8 ± 0.5 | 4.9 ± 0.4 |
| NPY + compound | 3.8 ± 0.4 | 1.5 ± 0.6 |

Since food deprivation induces an increase in the hypothalamic NPY levels, it has been postulated that food intake following a period of food deprivation is NPY-mediated. Therefore, the Y5 antagonists of Table 5 were administered co conscious rats following a 24 h food deprivation. Each of the human Y5 receptor antagonists shown in Table 5 was able to significantly reduce NPY-induced food intake in the animals, as shown below in Table 7. The food intake intake of animals treated with test compound is reported as a percentage of the food intake measured for control animals (treated with vehicle), i.e., 25% means the animals treated with the compound consumed only 25% as much food as the control animals. Measurements were performed two hours after administration of the test compound.

TABLE 7

Two-hour food intake of NPY-stimulated rats.
Food intake is expressed as the percentage of
intake compared to control rats.

| Example | Mean (%) |
|---|---|
| 31 | 27 |
| 32 | 36 |
| 36 | 35 |
| 38 | 80 |
| 40 | 55 |
| 37 | 58 |
| 77 | 32 |
| 44 | 73 |
| 45 | 84 |

These experiments indicate that the compounds of the present invention inhibit food intake in rats, especially when administered in a range of about 0.01 to about 100 mg/kg rat, by either oral, intraperitoneal or intravenous administration. The animals appeared normal during these experiments, and no ill effects on the animals were observed after the termination of the feeding experiments.

The binding properties of the compounds were also evaluated with respect to other cloned human G-protein coupled receptors. As shown in Table 8, below, the Y5-selective compounds described hereinabove exhibited lower affinity for receptors other than the Y-type receptors.

which are genetically obese (Sanacora et al., 1990) or made diabetic by treatment with streptozotocin (White et al., 1990). One potential explanation is that NPY, a potent stimulant of feeding behavior in normal rats, is disregulated in the overweight or diabetic animal so that food intake is increased, accompanied by obesity. The physiological stress of obesity increases the risk for health problems such as cardiovascular malfunction, osteoarthritis, and hyperinsulinemia, together with a worsened prognosis for adult-onset diabetes. A nonpeptide antagonist targeted to the Y5 receptor could therefore be effective as a way to control not only appetite and body weight but an entire range of obesity- and diabetes-related disorders (Dryden et al., 1994). There is also neurochemical evidence to suggest that NPY-mediated functions are disregulated in eating disorders such as bulimia and anorexia nervosa, so that they too could be responsive to treatment by a Y5-selective drug. It has been proposed, for example, that food intake in NPY-stimulated rats mimics the massive food consumption associated with binge eating in bulimia (Stanley, 1993). CSF levels of PYY but not NPY were elevated in bulimic patients who abstained from binging, and then diminished when binging was allowed (Berrettini et al., 1988). Conversely, NPY levels were elevated in underweight anorectic patients and then diminished as body weight was normalized (Kaye et al., 1990).

As described above, the human and rat in vitro expression models were used in combination to screen for compounds intended to modulate NPY-dependent feeding behavior. Using this approach, applicants have discovered several compounds which inhibit feeding behavior in animal models, which should lead to additional drug discoveries. The compounds according to the present invention inhibit food intake in Zucker obese rats in a range especially of about 0.01 to about 100 mg/kg after oral, intraperitoneal or intravenous administration.

The Y5 pharmacological profile further offers a new standard by which to review the molecular basis of all

TABLE 8

Cross-reactivity of compounds at other cloned human receptors

| Compound | Receptor (pKi) | | | | | | | | | | | | | | | |
|---|---|---|---|---|---|---|---|---|---|---|---|---|---|---|---|---|
| | $\alpha_{1d}$ | $\alpha_{1b}$ | $\alpha_{1a}$ | $\alpha_{2a}$ | $\alpha_{2b}$ | $\alpha_{2c}$ | H1 | H2 | D3 | $5HT_{1a}$ | $5HT_2$ | $5HT_7$ | $5HT_{1F}$ | $5HT_{1E}$ | $5HT_{1D\beta}$ | $5HT_{1D\alpha}$ |
| 31 | 6.68 | 7.17 | 7.08 | 6.52 | 6.51 | 7.07 | 6.33 | 5.92 | 6.61 | 5.88 | 6.74 | 6.50 | 5.30 | 5.30 | 5.30 | 5.32 |
| 32 | 6.90 | 7.35 | 7.47 | 6.74 | 6.58 | 7.07 | 7.04 | 6.29 | 6.69 | 5.54 | 6.55 | 6.42 | 5.30 | 5.30 | 5.30 | 6.04 |
| 36 | 7.01 | 7.22 | 7.72 | 7.31 | 6.96 | 7.39 | 6.73 | 5.85 | 6.35 | 6.73 | 5.93 | 6.37 | 5.30 | 5.30 | 5.37 | 5.94 |
| 38 | N.D. | N.D. | N.D. | N.D. | N.D. | N.D. | N.D. | N.D. | N.D. | N.D. | N.D. | N.D. | N.D. | N.D. | N.D. | N.D. |
| 40 | 6.80 | 6.98 | 7.34 | 7.05 | 6.43 | 7.15 | 6.22 | 5.72 | 6.29 | 6.56 | 5.99 | 6.39 | 5.30 | 5.30 | 5.41 | 5.98 |
| 37 | N.D. | N.D. | N.D. | N.D. | N.D. | N.D. | N.D. | N.D | N.D. | N.D. | N.D. | N.D. | N.D. | N.D. | N.D. | N.D. |
| 77 | 6.66 | 6.67 | 7.07 | 6.21 | 5.95 | 6.79 | 6.43 | 6.43 | 5.93 | 5.82 | 5.99 | 5.35 | 5.30 | 5.30 | 5.39 | 5.62 |
| 44 | N.D. | N.D. | N.D. | N.D. | N.D. | N.D. | N.D. | N.D. | N.D. | N.D. | N.D. | N.D. | N.D. | N.D. | N.D. | N.D. |
| 45 | N.D. | N.D. | N.D. | N.D. | N.D. | N.D. | N.D. | N.D. | N.D. | N.D. | N.D. | N.D. | N.D. | N.D. | N.D. | N.D. |

EXPERIMENTAL DISCUSSION

Y5 receptors are highly attractive targets for appetite and weight control based on several lines of research (Sahu and Kalra, 1993). NPY is the most potent stimulant of feeding behavior yet described (Clark et al., 1984; Levine and Morley, 1984; Stanley and Leibowitz, 1984). Direct injection of NPY into the hypothalamus of rats can increase food intake −10-fold over a 4-hour period (Stanley et al., 1992). NPY-stimulated rats display a preference for carbohydrates over protein and fat (Stanley et al., 1985). Interestingly, NPY and NPY mRNA are increased in food-deprived rats (Brady et al., 1990; O'Shea and Gundlach, 1991) and also in rats NPY-dependent processes. Such an exercise suggests that the Y5 receptor is likely to have a physiological significance beyond feeding behavior. It has been reported, for example, that a Y-type receptor can regulate luteinizing hormone releasing hormone (LHRH) release from the median eminence of steroid-primed rats in vitro with an atypical Y1 pharmacological profile. NPY, $NPY_{2-36}$, and LP-NPY were all effective at 1 uM but deletion of as few as four amino acids from the N-terminus of NPY destroyed biological activity. The Y5 may therefore represent a therapeutic target for sexual or reproductive disorders. It is worth while considering that the Y5 is so similar in pharmacological profile to the other Y-type receptors that it may have been overlooked among a mixed population of Y1, Y2 and Y4 receptors. Certain functions now associated with these subtypes could therefore be reassigned to Y5 as our pharmacological tools grow more sophisticated. By offering new insight into NPY receptor pharmacology, the Y5 thereby provides a greater clarity and focus in the field of drug design.

TABLE 9

Pathophysiological Conditions Associated With NPY
The following pathological conditions have been linked to either 1) application of exogenous NPY, or 2) changes in levels of endogenous NPY.

| | | |
|---|---|---|
| 1 | obesity | Sahu and Kalra, 1993 |
| 2 | eating disorders (anorexia and bulimia nervosa) | Stanley, 1993 |
| 3 | sexual/reproductive function | Clark, 1994 |
| 4 | depression | Heilig and Weiderlov, 1990 |
| 5 | anxiety | Wahlestedt et al., 1993 |
| 6 | cocaine addiction | Wahlestedt et al., 1991 |
| 7 | gastric ulcer | Penner et al., 1993 |
| 8 | memory loss | Morley and Flood, 1990 |
| 9 | pain | Hua et al., 1991 |
| 10 | epileptic seizure | Rizzi et al., 1993 |
| 11 | hypertension | Zukowska-Grojec et al., 1993 |
| 12 | subarachnoid hemorrhage | Abel et al., 1988 |
| 13 | shock | Hauser et al., 1993 |
| 14 | circadian rhythm | Albers and Ferris, 1984 |
| 15 | nasal congestion | Lacroix et al., 1988 |
| 16 | diarrhea | Cox and Cuthbert, 1990 |
| 17 | neurogenic voiding dysfunction | Zoubek et al., 1993 |

A successful strategy for the design of a Y5-receptor based drug or for any drug targeted to single G protein-coupled receptor subtype involves the screening of candidate compounds 1) in radioligand binding assays so as to detect affinity for cross-reactive G protein-coupled receptors, and 2) in physiological assays so as to detect undesirable side effects. In the specific process of screening for a Y5-selective drug, the receptor subtypes most likely to cross-react and therefore most important for radioligand binding screens include the other "Y-type" receptors, Y1, Y2, Y3, and Y4. Cross-reactivity between the Y5 and any of the other subtypes could result in potential complications as suggested by the pathophysiological indications listed in Table 9. In designing a Y5 antagonist for obesity and appetite control, for example, it is important not to design a Y1 antagonist resulting in hypertension or increased anxiety, a Y2 antagonist resulting in memory loss, or a Y4 antagonist resulting in increased appetite.

TABLE 10

Y-Type Receptor Indications

| Y-type Receptor Indications | Receptor Subtype | Drug Activity | Reference |
|---|---|---|---|
| obesity, appetite disorder | a typical Y1 | antagonist | Sahu and Kalra, 1993 |
| adult onset diabetes | a typical Y1 | antagonist | Sahu and Kalra, 1993 |

TABLE 10-continued

Y-Type Receptor Indications

| Y-type Receptor Indications | Receptor Subtype | Drug Activity | Reference |
|---|---|---|---|
| bulimia nervosa | a typical Y1 | antagonist | Stanley, 1993 |
| pheochromocytoma-induced hypertension | Y1 | antagonist | Grouzman et al., 1989 |
| subarachnoid hemorrhage | Y1 | antagonist | Abel et al., 1988 |
| neurogenic vascular hypertrophy | Y1 | antagonist | Zukowska-Grojec et al., 1993 |
| epileptic seizure | Y2 | antagonist | Rizzi et al., 1993 |
| hypertension central, peripheral regulation | peripheral Y1 central Y3 central Y2 | antagonist agonist antagonist | Grundemar and Hakanson, 1993 Barraco et al., 1991 |
| obesity, appetite disorder | Y4 or PP | agonist | Malaisse-Lagae et al., 1977 |
| anorexia nervosa | a typical Y1 | agonist | Berrettini et al., 1988 |
| anxiety | Y1 | agonist | Wahlestedt et al., 1993 |
| cocaine addiction | Y1 | agonist | Wahlestedt et al., 1991 |
| stress-induced gastric ulcer | Y1 Y4 or PP | agonist agonist | Penner et al., 1993 |
| memory loss | Y2 | agonist | Morley and Flood, 1990 |
| pain | Y2 | agonist | Hua et al., 1991 |
| shock | Y1 | agonist | Hauser et al., 1993 |
| sleep disturbances, jet lag | Y2 | not clear | Albers and Ferris, 1984 |
| nasal decongestion | Y1 Y2 | agonist agonist | Lacroix et al., 1988 |
| diarrhea | Y2 | agonist | Cox and Cuthbert, 1990 |

The Y5 receptor represents an enormous opportunity for the development of novel and selective drug therapies, particularly those targeted to appetite and weight control, but also for memory loss, depression, anxiety, gastric ulcer, epileptic seizure, pain, hypertension, subarachnoid hemorrhage, sleeping disturbances, nasal congestion, neurogenic voiding dysfuncion, and diarrhea.

In particular, the discovery of Y5-slective antagonists which inhibit food intake in rats provides a method of modifying feeding behavior in a wide variety of vertebrate animals.

REFERENCES

Abel, P. W., Han, C., Noe, B. D., and McDonald, J. K. (1988). Neuropeptide Y: vasoconstrictor effects and possible role in cerebral vasospasm after experimental subarachnoid hemorrhage. *Brain Res.* 463:250–258.

Albers, H. E., and Ferris, C. F. (1984). Neuropeptide Y: Role in light-dark cycle entrainment of hamster circadian rhythms. *Neurosci. Lett.* 50:163–168.

Aruffo, A. and Seed, B. (1987). Molecular cloning of a CD28 cDNA by a high efficiency COS cell expression system. *PNAS,* 84, 8573–8577.

Balasubramaniam, A., Sheriff, S., Johnson, M. E., Prabhakaran, M., Huang, Y., Fischer, J. E., and Chance, W. T. (1994). [D-Trp$^{32}$]Neuropeptide Y: A competitive antagonist of NPY in rat hypothalamus. *J. Med. Chem.* 37:311–815.

Benson, G. Anthony, and Spillane, William J. (1980). Sulfamic Acid and Its N-Substituted Derivatives. *Chem.Rev.* 80:151–186.

Berrettini, W. H., Kaye, W. H., Gwirtsman, H., and Allbright, A. (1988). Cerebrospinal fluid peptide YY immunoreactivity in eating disorders. *Neuropsychobiol* 19:121–124.

Bradford, M. M. (1976). A rapid and sensitive method for the quantitation of microgram quantities of protein utilizing the principle of protein-dye binding. *Anal. Biochem.* 72:248–254.

Brady, L. S., Smith, M. A., Gold, P. W., and Herkenham, M. (1990). Altered expression of hypothalamic neuropeptide Y mRNAs in food-restricted and food-deprived rats. *Neuroendocrinology* 52:441–447.

Chakraborty, T. K., Reddy, G. V., and Hussain, K. Azhar. (1991). Diastereoselective Strecker Synthesis using α-Phenylglycinol as Chiral Auxiliary. *Tetrahedron Letters.* 32:7597–7600.

Chance, W. T., Sheriff, S., Foley-Nelson, T., Fischer, J. E., and Balasubramaniam, A. (1989). Pertuss toxin inhibits neuropeptide Y-induced feeding in rats. *Peptides* 10, 1283–1286.

Clark, J. T. (1994). Aging-induced decrements in neuropeptide Y: The retention of ejaculatory behavior is associated with site-selective differences. *Neurobiology of Aging* 15:191–196.

Clark, J. T., Kalra, P. S., Crowley, W. R., and Kalra, S. P. (1984). Neuropeptide Y and human pancreatic polypeptide stimulate feeding behavior in rats. *Endocrinology* 115:427–429.

Cox, H., and Cuthbert, A. W. (1990). The effects of neuropeptide Y and its fragments upon basal and electrically stimulated ion secretion in rat jejunum mucosa. *Br. J. Pharmac.* 101:247–252.

Cullen, B. (1987). Use of eurkaryotic expression technology in the functional analysis of cloned genes. *Methods Enzymol.* 152:685–704.

Dryden, S., Frankish, H., Wang, Q., and Williams, G. (1994). Neuropeptide Y and energy balance: one way ahead for the treatment of obesity? *Eur. J. Clin. Invest.* 24:293–308.

Dumont, Y., J. -C. Martel, A. Fournier, S. St-Pierre, and R. Quirion. (1992). Neuropeptide Y and neuropeptide Y receptor subtypes in brain and peripheral tissues. *Progress in Neurobiology* 38:125–167.

Dumont, Y., Fournier, A.,. St-Pierre, S., Quiron, R. (1995). Characterization of Neuropeptide Y Binding Sites in Rat Brain Membrane Preparations Using [$^{125}$I] [Leu$^{31}$,Pro$^{34}$] Peptide YY and [$^{125}$]Peptide YY$_{3-36}$ as Selective Y$_1$ and Y$_2$ Radioligands. *J. Pharm. Exper. Ther.* 272:(2) 673–680.

Eva, C., Oberto, A., Sprengel, R. and E. Genazzani. (1992). The murine NPY-1 receptor gene: structure and delineation of tissue specific expression. *FEBS lett.* 314:285–288.

Eva, C., Keinanen, K., Monyer, H., Seeburg, P., and Sprengel, R. (1990). Molecular cloning of a novel G proteincoupled receptor that may belong to the neuropeptide receptor family. *FEBS Lett.* 271, 80–84.

Fuhlendorff, J., U. Gether, L. Aakerlund, N. Langeland-Johansen, H. Thogersen, S. G. Melberg, U. B. Olsen, O. Thastrup, and T. W. Schwartz. (1990). [Leu$^{31}$,Pro$^{34}$] Neuropeptide Y: A specific Y1 receptor agonist. *Proc. Natl. Acad. Sci. USA* 87:182–186.

Gerald, C., Adham, A., Kao, H T, Olsen, M. A., Laz, T. M., Vaysse, P., Hartig, P. R., Branchek, T. A. and R. L. Weinshank. The 5-HT$_4$ receptor: molecular cloning and pharmacological characterization of two splice variants (submitted for publication).

Grouzman, E., Comoy, E., and Bohuon, C. (1989). Plasma neuropeptide Y concentrations in patients with neuroendocrine tumors. *J. Clin. Endoc. Metab.* 68:808–813.

Grundemar, L. and R l Hakanson (1994). Neuropeptide Y effector systems: perspectives for drug development. *Trends. Pharmacol.* 15:153–159.

Grundemar, L., J. L. Krstenansky, and R. Hakanson. (1992). Activation of neuropeptide Y1 and neuropeptide Y2 receptors by substituted and truncated neuropeptide Y analogs: identification of signal epitopes. *Eur. J. Pharmacol.* 232:271–278.

Gubler, U abd B. J. Hoffman. (1983). A simple and very efficient method for generating cDNA libraries. *Gene.* 25, 263–269

Hau, X. -Y., Boublik, J. H., Spicer, M. A., Rivier, J. E., Brown, M. R., and Yaksh, T. L. (1991). The antinociceptive effects of spinally administered neuropeptide Y in the rat: Systematic studies on structure-activity relationship. *JPET* 258:243–253.

Hauser, G. J., Myers, A. K., Dayao, E. K., and Zukowska-Grojec, Z. (1993). Neuropeptide Y infusion improves hemodynamics and survival in rat endotoxic shock. *Am. J. Physiol.* 265:H1416–H1423.

Heilig, M., and Widerlov, E. (1990). Neuropeptide Y: an overview of central distribution, functional aspects, and possible involvement in neuropsychiatric illnesses. *Acta Psychiatr. Scand.* 82:95–114.

Herzog, H., Y. J. Hort, H. J. Ball, G. Hayes, J. Shine, and L. Selbie. (1992). Cloned human neuropeptide Y receptor couples to two different second messenger systems. *Proc. Natl. Acad. Sci. USA* 89:5794–5798.

Herzog, H., Y. J. Hort, H. J. Ball, G. Hayes, J. Shine, and L. Selbie. (1992). Cloned human neuropeptide Y receptor couples to two different second messenger systems. *Proc. Natl. Acad. Sci. USA* 89, 5794–5798.

Horstman, D. A., Brandon, S., Wilson A. L., Guyer, C. A., Cragoe, E. J., Jr., Limbird, L. E. (1990). An Aspartate Conserved Among G-protein Receptors Confers Allosteric Regulation of Alpha2-Adrenergic Receptors by Sodium. *J. Biol. Chem.* 265:(35) 21590–21595.

Kalra, S. P., Fuentes, M., Fournier, A., Parker, S. L., and Crowley, W. R. (1992). Involvement of the Y-1 receptor subtype in the regulation of luteinizing hormone secretion by neuropeptide Y in rats. *Endocrinology* 130:3323–3330.

Kalra, S. P., Dube, M. G., Fournier, A., and Kalra, P. S. (1991). Structure-function analysis of stimulation of food intake by neuropeptide Y: Effects of receptor agonists. *Physiology & Behavior* 50:5–9.

Kaye, W. H., Berrettini, W., Gwirtsman, H., and George, D. T. (1990). Altered cerebrospinal fluid neuropeptide Y and peptide YY immunoreactivity in anorexia and bulimia nervosa. *Arch. Gen. Psychiat.* 47:548–556.

Kieffer, B., Befort, K., Gaveriaux-Ruff, C. and Hirth, C. G. (1992). The δ-opioid receptor: Isolation of a cDNA by expression cloning and pharmacological characterization. *Proc. natl. Acad. Sci. USA* 89, 12048–12052.

Kingston, R. E. (1987) in Ausubel, F. M.,Brent, R., Kingston, R. E., Moore, D. D., Seidman, J. G., Smith, J. A. & Struhl, K. (Eds), *Current Protocols in Molecular Biology*, John Wiley and Sons, N.Y., Vol. 1, pp. 4.2.3–4.2.4.

Kloek, J. A. and Leschinsky, K. L. (1976). An Improved Synthesis of Sulfamoyl Chlorides. *J. Org. Chem.* 41.

Kluxen, F. W., Bruns, C. and Lubbert H. (1992). Expression cloning of a rat brain somatostatin receptor cDNA. *Proc. Natl. Acad. Sci. USA* 89, 4618–4622.

Kornfeld, R. and Kornfeld, S. (1985). Assembly of asparagine linked oligosaccharides. *Annu. Rev. Biochem.* 54, 631–664.

Kozak, M. (1989). The scanning model for translation: an update. *J. Cell Biol.* 108, 229–241.

Kozak, M. (1991). Structural features in eukaryotic mRNAs that modulate the initiation of translation. *J. Biol. Chem.* 266, 19867–19870.

Krapcho, A. Paul and Kuell, Christopher S. (1990).Monoprotected Diamines, N-tert-Butoxycarbonyl-α,ω-Alkanediamines from α,ω-Alkanediamines. *Synthetic Communications.* 20:2559–2564.

Krause, J., C. Eva, P. H. Seeburg, and R. Sprengel. (1991). Neuropeptide $Y_1$ subtype pharmacology of a recombinantly expressed neuropeptide receptor. *Mol. Pharmacol.* 41:817–821.

Lacroix, J. S., Stjarne, P., Angard, A., and Lundberg, M. (1988). Sympathetic vascular control of the pig nasal mucosa: reserpine-resistant, non-adrenergic nervous responses in relation to neuropeptide Y and ATP. *Acta Physiol. Scand.* 133:183–197.

Landschultz, W. H., Johnson, P. F. and S. L. McKnight. (1988). The leucine zipper: a hypothetical structure common to a new class of DNA binding proteins. *Science* 240, 1759–1764.

Larhammar, D., A .G. Blomqvist, F. Yee, E. Jazin, H. Yoo, and C. Wahlestedt. (1992). Cloning and functional expression of a human neuropeptide Y/peptide YY receptor of the Y1 type. *J. Biol. Chem.* 267:10935–10938.

Levine, A. S., and Morley, J. E. (1984). Neuropeptide Y: A potent inducer of consummatory behavior in rats. *Peptides* 5:1025–1029.

Maggio, R., Vogel Z. and J. Wess. (1993). Coexpression studies with mutant muscarinic/adrenergic receptors provide evidence for intermolecular "cross-talk" between G-protein-linked receptors. *Proc. Natl. Acad. Sci. USA* 90:3103–3107.

Malaisse-Lagai, F., Carpentier, J.- L., Patel, Y. C., Malaisse, W. J., and Orci, L. (1977). Pancreatic polypeptide: A possible role in the regulation of food intake in the mouse. Hypothesis. *Experientia* 33:915–917.

McCormick, M. (1987). Sib Selection. *Methods in Enzymology*, 151:445–449.

Miller, J. and Germain, R. N. (1986). Efficient cell surface expression of class II MHC molecules in the absence of associated invariant chain. *J. Exp. Med.* 164:1478–1489.

Michel, M. C. (1991). Receptors for neuropeptide Y: multiple subtypes and multiple second messengers. *Trends Pharmacol.:* 12:389–394.

Morley, J. E., and Flood, J. F. (1991). Neuropeptide Y and memory processing. *An. N.Y. Acad. Sci.* 611:226–231.

Okayama, H. and P. Berg (1983). A cDNA cloning vector that permits expression of cDNA inserts in mammalian cells. *Mol. Cell. Biol.* 3:280–289.

Shea, R. D., and Gundlach, A. L. (1991). Preproneuropeptide Y messenger ribonucleic acid in the hypothalamic arcuate nucleus of the rat is increased in food deprivation or dehydration. *J. Neuroendocrinol.* 3:11–14.

O'Shea, E. K., Rutkowski, R. and P. S. Kim. (1989). Evidence that the leucine zipper is a coiled coil. *Science* 243:538–542.

Penner, S. B., Smyth, D. D., and Glavin, G. B. (1993). Effects of neuropeptide Y and [Leu$^{31}$,Pro$^{34}$]Neuropeptide Y on experimental gastric lesion formation and gastric secretion in the rat. JPET. 266:339–343.

Probst, W. C., Snyder, L. A., Schuster, D. I., Brosius, J and Sealfon, S. C. (1992). Sequence alignment of the G-protein coupled receptor superfamily. *DNA and Cell Bio.* 11, 1–20.

Sahu, A., and Kalra, S. P. (1993). Neuropeptidergic regulation of feeding behavior (neuropeptide Y). *Trends Endocrinol. Metab.* 4:217–224.

Sato, M., Kawashima, Y., Goto, J., Yamane, Y., Chiba, Y., Jinno, S., Satake, M., Iwata, C. (1995). Synthesis and evaluation of novel fluorinated sulotroban-related sulfonamide derivatives as thromboxane $A_2$ receptor antagonists. *EurJ Med Chem.* 30:403–414.

Still, W. Clark, Kahn, Michael and Mitra, Abhijit. (1978). Rapid Chromatographic Technique for Preparative Separations with Moderate Resolution. *J.Org.Chem.* 43:2923.

Robert, J. J., Orosco, M., Rouch, C., Jacquot, C., Cohen, Y. (1989) Unexpected Responses of the Obese "Cafeteria" Rat to the Peptide FMRF-Amide. *Pharm. Bioch. Behavior* 34:341–344.

Rizzi, M., Samini, R., Sperk, G., and Vezzani, A. (1993). Electrical kindling of the hippocampus is associated with functional activation of neuropeptide Y-containing neurons. *Eur. J. Neuroscience* 5:1534–1538.

Sanacora, G., Kershaw, M., Finkelstein, J. A., and White, J. D. Increased hypothalamic content of preproneuropeptide Y messenger ribonucleic acid in genetically obese Zucker rats and its regulation by food deprivation. *Endocrinology* 127:730–737 (1990).

Schwartz, T. W., J. Fuhlendorff, L. L. Kjems, M. S. Kristensen, M. Vervelde, M. O'Hare, J. L. Krstenansky, and B. Bjornholm. (1990). Signal epitopes in the three-dimensional structure of neuropeptide Y. *Ann. N.Y. Acad. Sci.* 611:35–47.

Stanley, B. G., Magdalin, W., Seirafi, A., Nguyen, M. M., and Leibowitz, S. F. (1992). Evidence for neuropeptide Y mediation of eating produced by food deprivation and for a variant of the Y1 receptor mediating this peptide's effect. *Peptides* 13:581–587.

Stanley, B. G., and Leibowitz, S. F. (1984). Neuropeptide Y: Stimulation of feeding and drinking by injection into the paraventricular nucleus. *Life Sci.* 35:2635–2642.

Stanley, B. G. Neuropeptide Y in multiple hypothalamic sites controls eating behavior, endocrine, and autonomic systems for body energy balance. In: *The Biology of Neuropeptide Y and Related Peptides*, pp. 457–509. Eds. W. F. Colmers and C. Wahlestedt. Humana Press, Totowa, N.J. (1993).

Stanley, B. G., Daniel, D. R., Chin, A. S., and Leibowitz, S. F. (1985). Paraventricular nucleus injections of peptide YY and neuropeptide Y preferentially enhance carbohydrate ingestion. *Peptides* 6:1205–1211.

Wahlestedt, C., L. Edvinsson, E. Ekblad, and R. Hakanson. Effects of neuropeptide Y at sympathetic neuroeffector junctions: Existence of $Y_1$ and $Y_2$ receptors. In: *Neuronal messengers in vascular function*, Fernstrom Symp. No 10., pp. 231–242. Eds A. Nobin and C. H. Owman. Elsevier: Amsterdam (1987).

Wahlestedt, C., Karoum, F., Jaskiw, G., Wyatt, R. J., Larhammar, D., Ekman, R., and Reis, D. J. (1991). Cocaine-induced reduction of brain neuropeptide Y synthesis dependent on medial prefrontal cortex. *Proc. Natl. Acad. Sci.* 88:2978–2082.

Wahlestedt, C., Regunathan, S., and D. J. Reis (1991). Identification of cultured cells selectively expressing Y1-, Y2-, or Y3-type receptors for neuropeptide Y/peptide YY. *Life Sciences SO: PL*-7 - PL-12.

Wahlestedt, C., Pich, E. M., Koob, G. F., Yee, F., and Heilig, M. (1993). Modulation of anxiety and neuropeptide Y-Y1 receptors by antisense oligodeoxynucleotides. *Science* 259:528–531.

Wahlestedt, C., and D. J. Reis. (1993). Neuropeptide Y-Related Peptides and Their Receptors—Are the Receptors Potential Therapeutic Targets? *Ann. Rev. Pharmacol. Tox.* 32:309–352

Warden, D. and H. V. Thorne. (1968). Infectivity of polyoma virus DNA for mouse embryo cells in presence of diethylaminoethyl-dextran. *J. Gen. Virol.,* 3, 371.

Wells, J. A. (1994). Structural and functional basis for hormone binding and receptor oligomerization. *Current Opinion in Cell Biology* 6:163–173

White, J. D., Olchovsky, D., Kershaw, M., and Berelowitz, M. (1990). Increased hypothalamic content of preproneuropeptide-Y messenger ribonucleic acid in streptozotocin-diabetic rats. *Endocrinology* 126:765–772.

Zoubek, J., Somogyi, G. T., and De Groat, W. C. (1993). A comparison of inhibitory effects of neuropeptide Y on rat urinary bladder, urethra, and vas deferens. Am. J. Physiol. 265:R536–R543.

Zukowska-Grojec, Z., Haass, M., and Bayorh, M. (1986). Neuropeptide Y and peptide YY mediate non-adrenergic vasoconstriction and modulate sympathetic responses in rats.*Reg. Pept.* 15:99–110.

Zukowska-Grojec, Z., Bergeson, S., Kuch-Wocial, A., and Colton, C. (1993). Mitogenic effect of neuropeptide Y in rat vascular smooth muscle cells. Neuropeptide Y Conference Abstracts, (Cambridge) C10.

What is claimed is:

1. A compound having the structure:

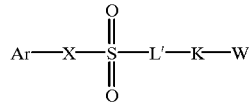

wherein Ar is

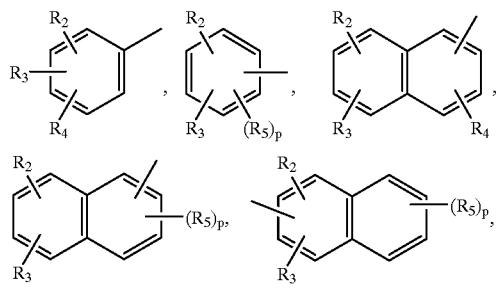

wherein p is an integer from 0 to 2;
wherein X is a single bond;
wherein each $R_2$ is independently H; F; Cl; Br; I; $NO_2$; OH; $C_1$–$C_4$ alkyl; $C_2$–$C_4$ alkenyl; $C_1$–$C_4$ alkoxy; $C_1$–$C_4$ hydroxyalkyl; $C_1$–$C_4$ methoxyalkyl; $C_1$–$C_4$ monohaloalkyl; $C_1$–$C_4$ polyhaloalkyl; $N(R_5)_2$; $NHCOR_5$; $N(COR_5)_2$; $NHCO_2R_5$; $NHCONHR_5$; $NHSO_2R_5$; $N(SO_2R_5)_2$; $CO_2R_5$; $CON(R_5)_2$; $SO_2N(R_5)_2$; phenoxy; phenyl; or naphthyl; and wherein the phenoxy, phenyl, or naphthyl is substituted with H, F, Cl, Br, I, $CF_3$, $C_1$–$C_4$ alkyl, $C_1$–$C_4$ alkoxy, $C_1$–$C_4$ alkylthio, or $NO_2$;
wherein each $R_3$ is independently H; F; Cl; Br; I; $NO_2$; OH; $C_1$–$C_4$ alkyl; $C_2$–$C_4$ alkenyl; $C_1$–$C_4$ alkoxy; $C_1$–$C_4$ hydroxyalkyl; $C_1$–$C_4$ methoxyalkyl; $C_1$–$C_4$ monohaloalkyl; $C_1$–$C_4$ polyhaloalkyl; $N(R_5)_2$; $NHCOR_5$; $N(COR_5)_2$; $NHCO_2R_5$; $NHCONHR_5$; $NHSO_2R_5$; $N(SO_2R_5)_2$; $CO_2R_5$; $CON(R_5)_2$; or $SO_2N(R_5)_2$; or $R_2$ and $R_3$ present on adjacent carbon atoms can constitute $C_5$–$C_7$ cycloalkyl;
wherein each $R_4$ is independently H; F; Cl; Br; I; $NO_2$; OH; $C_1$–$C_4$ alkyl; $C_1$–$C_4$ alkoxy; $C_1$–$C_4$ hydroxyalkyl; $C_1$–$C_4$ methoxyalkyl; $C_1$–$C_4$ monohaloalkyl; $C_1$–$C_4$ polyhaloalkyl; $N(R_5)_2$; $NHCOR_5$; N $(COR_5)_2$; $NHCO_2R_5$; $NHCONHR_5$; $NHSO_2R_5$; $N(SO_2R_5)_2$; $CO_2R_5$; $CON(R_5)_2$; or $SO_2N(R_5)_2$;
wherein each $R_5$ is independently H; $C_1$–$C_3$ alkyl; $C_1$–$C_3$ monohaloalkyl; or $C_1$–$C_3$ polyhaloalkyl;
wherein L' is —$NR_1$—L—;
wherein L is

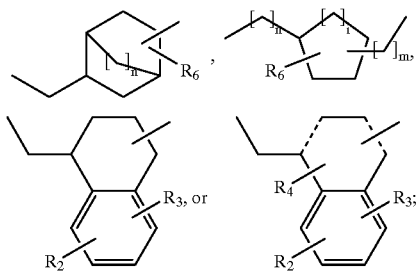

wherein $R_1$ is H; or $C_1$–$C_3$ straight chained alkyl;
wherein one dashed line is a double bond and the other dashed line is a single bond;
wherein each R6 is independently H; CN; $OR_5$; $C_1$–$C_5$ alkyl; $CH_2OR_5$; $CON(R_5)_2$; $CO_2R_5$; phenyl; or naphthyl; wherein the phenyl, or naphthyl is substituted with H, F, Cl, Br, I, $CF_3$, $C_1$–$C_4$ alkyl, $C_1$–$C_4$ alkoxy, $C_1$–$C_4$ alkylthio, or $NO_2$;

wherein i is an integer from 1 to 4; wherein n is an integer from 0 to 3; wherein m is an integer from 0 to 3;

wherein K is —$CH_2$—$NR_{10}$—$CHR_7$—$(CH_2)_1$—;

wherein j is an integer from 0 to 3;

wherein $R_7$ is H; $C_1$–$C_6$ alkyl; $CH_2OR_5$; $(CH_2)_p NHCO_2R_5$; $(CH_2)_p NHSO_2R_5$; $CH_2N(R_{11})_2$; phenyl; or naphthyl;

wherein W is

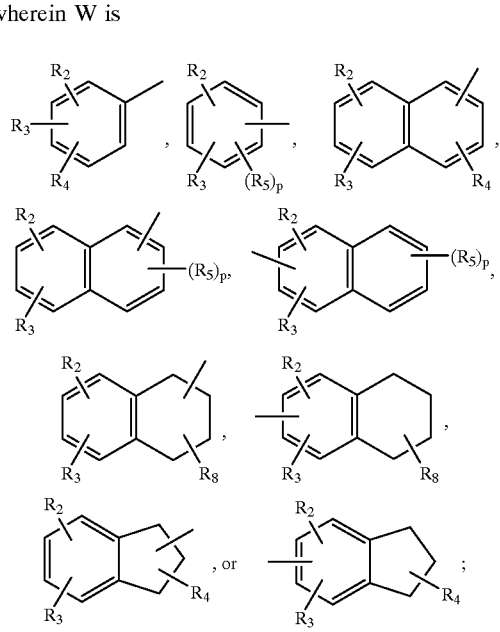

wherein $R_8$ is independently H; F; Cl; Br; I; $NO_2$; OH; =O; $C_1$–$C_4$ alkyl; $C_1$–$C_4$ alkoxy; $C_1$–$C_4$ hydroxyalkyl; $C_1$–$C_4$ methoxyalkyl; $C_1$–$C_4$ monohaloalkyl; $C_1$–$C_4$ polyhaloalkyl; $N(R_5)_2$; $NHCOR_5$; $N(COR_5)_2$; $NHCO_2R_5$; $NHCONHR_5$; $NHSO_2R_5$; $N(SO_2R_5)_2$; $CO_2R_5$; $CON(R_5)_2$; or $SO_2N(R_5)_2$;

wherein $R_{10}$ is H; or $C_1$–$C_6$ alkyl;

wherein $R_{11}$ is H; $COR_5$; $COR_5$; $SO_2R_5$; or $SO_2R_{12}$; and wherein $R_{12}$ is phenoxy; phenyl, or naphthyl; wherein the phenoxy, phenyl, or naphthyl is substituted with H, F, Cl, Br, I, $CF_3$, $C_1$–$C_4$ alkyl, $C_1$–$C_4$ alkoxy, $C_1$–$C_4$ alkylthio, $NO_2$, or phenyl;

or a pharmaceutically acceptable salt thereof.

2. An (+) enantiomer of the compound of claim 1.
3. An (−) enantiomer of the compound of claim 1.
4. A compound of claim 1, wherein $R_1$ is H; wherein L is

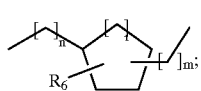

and wherein W is

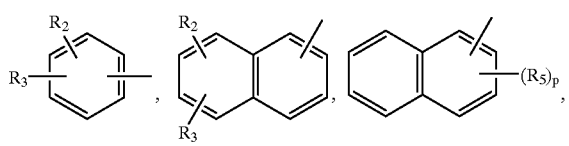

5. A compound of claim 4, wherein Ar is:

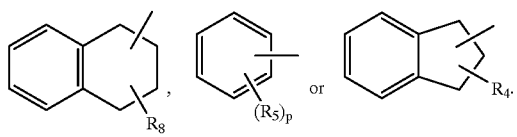

wherein each of $R_2$, $R_3$ and $R_4$ is independently H; F, Cl, Br or I; $NO_2$; OH; $C_1$–$C_4$ alkoxy; $C_1$–$C_4$ hydroxyalkyl; $C_1$–$C_4$ monohaloalkyl; $C_1$–$C_4$ polyhaloalkyl; or $N(R_5)_2$;

wherein each $R_5$ is independently $C_1$–$C_3$ alkyl;

wherein L is

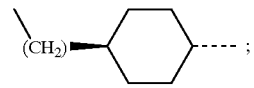

wherein $R_7$ is H; $CH_2OH$; or $CH_2OR_5$;

and wherein W is

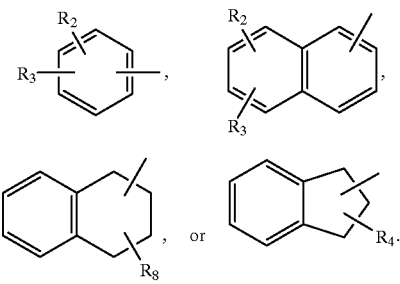

6. The compound of claim 1, wherein the compound is selected from the group consisting of:

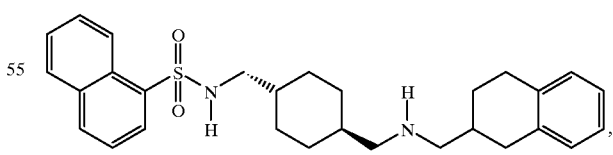

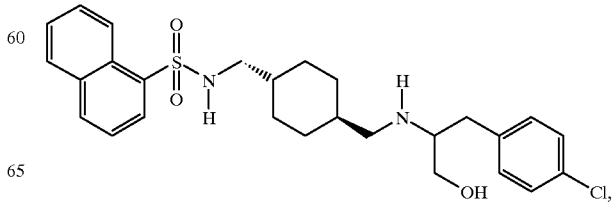

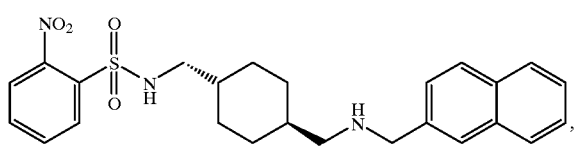

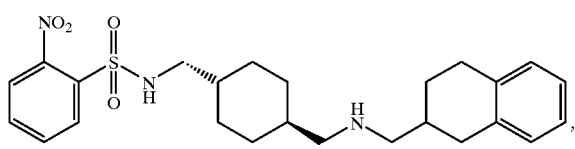

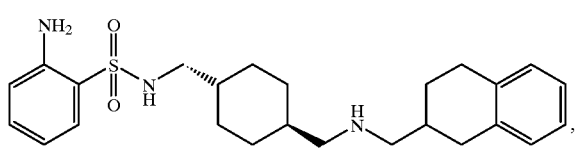

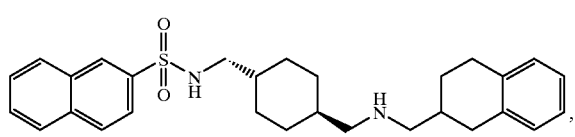

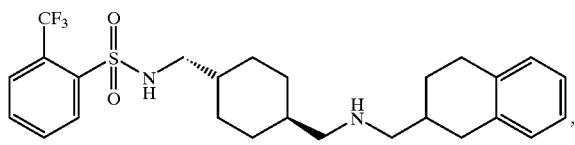

7. A method of modifying feeding behavior of a subject in need thereof which comprises administering to the subject an effective amount of the compound of claim 1 to decrease the consumption of food by the subject so as to thereby modify the feeding behavior of the subject.

8. A method of treating a feeding disorder in a subject in need thereof which comprises administering to the subject an effective amount of the compound of claim 1 to decrease the consumption of food by the subject.

9. The method of claim 7 or 8, wherein the feeding disorder is bulimia, obesity or bulimia nervosa.

10. The method of claim 9, wherein the subject is a vertebrate, a mammal, a human or a canine.

11. The method of claim 7 or 8, wherein the compound is administered in combination with food.

* * * * *